US008957059B2

(12) United States Patent
Carruthers et al.

(10) Patent No.: US 8,957,059 B2
(45) Date of Patent: Feb. 17, 2015

(54) MODULATORS OF SEROTONIN RECEPTORS

(71) Applicant: Janssen Pharmaceutica NV, Beerse (BE)

(72) Inventors: Nicholas I. Carruthers, Poway, CA (US); Jill A. Jablonowski, San Diego, CA (US); Brock T. Shireman, Poway, CA (US); Vi T. Tran, New York, NY (US)

(73) Assignee: Janssen Pharmaceutica NV, Beerse (BG)

( * ) Notice: Subject to any disclaimer, the term of this patent is extended or adjusted under 35 U.S.C. 154(b) by 0 days.

(21) Appl. No.: 14/051,027

(22) Filed: Oct. 10, 2013

(65) Prior Publication Data

US 2014/0038934 A1 Feb. 6, 2014

Related U.S. Application Data

(62) Division of application No. 13/126,213, filed as application No. PCT/US2009/062623 on Oct. 29, 2009, now Pat. No. 8,575,364.

(60) Provisional application No. 61/109,899, filed on Oct. 30, 2008.

(51) Int. Cl.
*C07D 205/04* (2006.01)
*A61K 31/397* (2006.01)
*C07D 211/46* (2006.01)
*C07D 207/06* (2006.01)
*C07D 207/12* (2006.01)
*C07D 211/48* (2006.01)
*C07D 207/08* (2006.01)

(52) U.S. Cl.
CPC ............ *C07D 211/46* (2013.01); *A61K 31/397* (2013.01); *C07D 205/04* (2013.01); *C07D 207/06* (2013.01); *C07D 207/12* (2013.01); *C07D 211/48* (2013.01); *C07D 207/08* (2013.01)
USPC ...................... 514/210.01; 548/952

(58) Field of Classification Search
CPC ............................ C07D 205/04; A61K 31/397
USPC ...................... 514/210.01; 548/952
See application file for complete search history.

(56) References Cited

U.S. PATENT DOCUMENTS

| 3,577,415 | A | 5/1971 | Cale et al. |
| 4,146,630 | A | 3/1979 | Kampe et al. |
| 5,130,309 | A | 7/1992 | Shanklin et al. |
| 8,642,583 | B2 | 2/2014 | Carruthers et al. |

FOREIGN PATENT DOCUMENTS

| DE | 1 964 510 A1 | 7/1970 |
| DE | 27 37 630 A1 | 3/1979 |
| DE | 27 37 630 C2 | 3/1979 |
| EP | 0 600 717 A1 | 11/1993 |
| EP | 0 863 136 A1 | 2/1997 |
| JP | 03 264 583 | 11/1991 |
| WO | WO 99 23073 A1 | 5/1999 |
| WO | WO 02 18333 A1 | 3/2002 |
| WO | WO 2004 113297 A2 | 12/2004 |
| WO | WO 2005 047246 A1 | 5/2005 |
| WO | WO 2006 025517 A1 | 3/2006 |
| WO | WO 2007 038459 A2 | 4/2007 |
| WO | WO 2007 072150 A2 | 6/2007 |
| WO | WO 2007 116230 A1 | 10/2007 |
| WO | WO 2008 009495 A1 | 1/2008 |
| WO | WO 2008 023258 A1 | 2/2008 |
| WO | WO 2008 023720 A1 | 2/2008 |
| WO | WO 2008 077265 A1 | 7/2008 |

OTHER PUBLICATIONS

U.S. Appl. No. 61/109,903, Oct. 30, 2008, Carruthers et al.
Bagshawe et al. "Antibody-Directed Enzyme Prodrug Therapy: A Review" Drug Dev Res 1995 vol. 34 pp. 220-230.
Berge et al. "Pharmaceutical Salts". J. Pharm Sci 1977 vol. 66 pp. 1-19.
Bertolini et al."A New Rational Hypothesis for the Pharmacophore of the Active Metabolite of Leflunomide, A Potent Immunosuppressive Drug" J Med Chem 1997 vol. 40 pp. 2011-2016.
Bodor et al. "Novel Approaches to the Design of Safer Drugs: Soft Drugs and Site-Specific Chemical Delivery Systems" Adv Drug Res 1984 vol. 13 pp. 224-331.
Bundgaard et al Design of Prodrugs H Bundgaard Ed. Elsevier 1985.
Chappie et al "Discovery of a Series of 6,7-Dimethoxy-4-Pyrrolidylquinazoline PDE10A Inhibitors" Journal of Medicinal Chemistry 2007 vol. 50(2) pp. 182-185.
Fleisher et al "Improved Review Oral Drug Delivery: Solubility Limitations of Prodrugs Overcome by the Use" Adv Drug Delivery Rev 1996 vol. 19 pp. 115-130.
Greene et al Protecting Groups in Organic Synthesis $3^{rd}$. Ed. T.W. Greene and P.G. Wuts John Wiley and Sons 1999.
Hoyer et al "Molecular, Pharmacological and Functional Diversity of 5-HT Receptors" Pharmacol Biochem Behav 2002 vol. 71 pp. 533-554.
Larsen et al Design and Application of Prodrugs, Drug Design and Development Krogsgaard-Larsen et al Harwood Academic Publishers 1991.
Paulekuhn et al "Trends in Active Pharmaceutical Ingredient Salt Selction Based on Analysis of the Orange Book Database" J Med Chem 2007 vol. 50 pp. 6665-6672.
Robinson et al "Discovery of the Hemifumarate and (A-L-alanyloxy)Methyl Ether As Prodrugs of an Antirheumatic Oxindloe: Prodrugs for the Enolic OH Group" J Med Chem 1996 Vlume 39 pp. 10-18.
Roth et al "The Multiplicity of Serotonin Receptors: Useselly Diverse Moledcules or an Embarassment of Riches?" The Neuroscientist 2000 vol. 6(4) pp. 252-262.

(Continued)

*Primary Examiner* — Robert Havlin
(74) *Attorney, Agent, or Firm* — Michael J. Atkins

(57) ABSTRACT

Certain biphenyl compounds are serotonin modulators useful in the treatment of serotonin-mediated diseases.

10 Claims, No Drawings

(56) References Cited

OTHER PUBLICATIONS

Shan et al "Prodrug Strategies Based on Intramolecular Cyclizaton Reactions" J Pharm Sci 1997 vol. 86(7) pp. 765-767.

Stahl et al Essential Psychopharmacology 2000 2nd Ed Cambridge Univ Press Cambridge UK 2000.

Stahl and Wermuth EDS Handbook of Pharmaceutical Salts, Propeties, Selection, and Use Wiley-VCH and VHCA Zurich 2002.

Harrak et al. The First Synthesis of Spiro (1,4-Benzodioxin-2,4'-Piperidines) and Spiro (1,4-Benzodioxin-2,3'-Pyrrolidines) Synlett 2003 vol. 6 pp. 813-816.

Nahm et al "N-Methoxy-Methylamides As Effective Acylating Agents" Tetrahderon Letters 1981 vol. 22(39) pp. 3815-3818.

Shimizu et al "Industrial Synthesis of Maxacalcitol, The Antihyperparathyroidism and Antipsoriatic Vitamin D3 Analogue Exbiting Low Calcemic Activity" Organic Process Research and Development 2005 vol. 9 pp. 278-287.

MODULATORS OF SEROTONIN RECEPTORS

CROSS REFERENCE TO RELATED APPLICATION

This application claims the benefit of U.S. provisional patent application Ser. No. 61/109,899, filed Oct. 30, 2008.

FIELD OF THE INVENTION

There is provided by the present invention compounds that are serotonin receptor modulators. More particularly, there is provided by the present invention biphenyl compounds that are serotonin receptor modulators useful for the treatment of disease states mediated by serotonin receptor activity.

BACKGROUND OF THE INVENTION

Serotonin (5-hydroxytryptamine, 5-HT) is a major neurotransmitter eliciting effects via a multiplicity of receptors. To date, at least fifteen different 5-HT receptors have been identified, largely as the result of cDNA cloning. These receptors have been grouped into seven families (5-HT$_1$ through 5-HT$_7$) (Hoyer, D. et al. *Pharmacol. Biochem. Behav.* 2002, 71, 533-554).

Fourteen of the fifteen cloned 5-HT receptors are expressed in the brain. 5-HT is implicated in many disease states, particularly conditions of the central nervous system including; depression, anxiety, schizophrenia, eating disorders, obsessive compulsive disorder, learning and memory dysfunction, migraine, chronic pain, sensory perception, motor activity, temperature regulation, nociception, sexual behavior, hormone secretion, and cognition.

The identification of multiple 5-HT receptors has provided the opportunity to characterize existing therapeutic agents thought to act via the serotonergic system. Consequently, this has led to the realization that many drugs have non-selective properties (Roth, B. L. et al. *Neuroscientist* 2000, 6(4), 252-262). For example, the antipsychotic drugs, clozapine, chlorpromazine, haloperidol and olanzapine exhibit affinities for multiple serotonin receptors in addition to other families of receptors. Similar behavior has been noted for antidepressants including imipramine, nortriptaline, fluoxetine and sertraline. Similarly, the anti-migraine agent sumatriptan exhibits high affinity for several serotonin receptors. While the lack of selectivity often contributes to a favorable therapeutic outcome, it can also cause undesirable and dose-limiting side effects (Stahl, S. M. *Essential Psychopharmacology*, 2$^{nd}$ ed., Cambridge University Press, Cambridge, U.K., 2000). For example, the inhibition of serotonin and norepinephrine uptake together with 5-HT$_2$ receptor blockade is responsible for the therapeutic effects of the tricyclic antidepressants. In contrast, their blockade of histamine H$_1$, muscarinic and alpha-adrenergic receptors can lead to sedation, blurred vision and orthostatic hypertension respectively. Likewise, the atypical antipsychotics, including olanzapine and clozapine, are considered to have positive therapeutic effects attributable to their actions at 5-HT$_2$, D$_2$ and 5-HT$_7$ receptors. Conversely, their side effect liability is due to their affinities for a range of dopaminergic, serotonergic and adrenergic receptors.

Elucidating selective ligands has the potential to ameliorate untoward pharmacologies and provide novel efficacious therapies. More importantly, the ability to obtain compounds which portray receptor selectivity provides the prospect to target distinct therapeutic mechanisms and improve clinical responses with a single drug. Consequently, there remains a need for potent serotonin receptor modulators with desirable pharmaceutical properties.

SUMMARY OF THE INVENTION

Certain biphenyl derivatives have now been found to have 5HT$_7$ modulating activity. In particular, the invention is directed to the general and preferred embodiments defined, respectively, and by the independent and dependent claims appended hereto, which are incorporated by reference herein.

Thus, in one general aspect, the invention relates to compounds of Formulae (I) and (II):

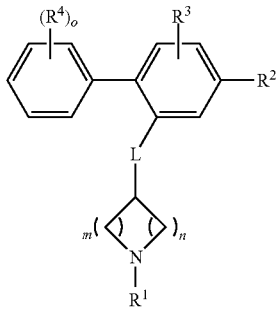

(I)

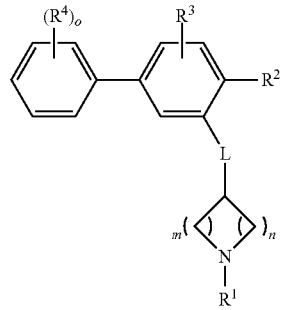

(II)

wherein
R$^1$ is —H, —C$_{1-4}$alkyl, or —C$_{3-6}$cycloalkyl;
m is 1 or 2,
n is 1 or 2, with the proviso that if m is 2, then n is not 1;
L is absent or O;
R$^2$ is —H, halo, —CN, —CF$_3$, —OC$_{0-4}$alkylCF$_3$, —OC$_{1-4}$alkyl, —C$_{3-6}$cycloalkoxy, —OCH$_2$C$_{3-6}$cycloalkyl, or —C(O)N(R$_a$)$_2$;
  each R$_a$ is individually —H or —C$_{1-4}$alkyl;
R$^3$ is —H or —C$_{1-4}$alkyl;
o is 0, 1, or 2; and
each R$^4$ substituent is independently —H, halo, —OCF$_3$, —CF$_3$, —CN, —C$_{1-4}$alkyl, or —OC$_{1-4}$alkyl.

The invention also relates to stereoisomeric forms, hydrates, solvates, pharmaceutically acceptable salts, pharmaceutically acceptable prodrugs, and pharmaceutically active metabolites of compounds of Formulae (I) or (II). In certain preferred embodiments, the compound of Formulae (I) or (II) is a compound selected from those species described or exemplified in the detailed description below.

In a further general aspect, the invention relates to pharmaceutical compositions each comprising: (a) an effective amount of an agent selected from compounds of Formulae (I) or (II) and stereoisomeric forms, hydrates, solvates, pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition (collectively, "indications") mediated by 5HT$_7$ activity, comprising administering to the subject in need of such treatment an effective amount of a compound of Formulae (I) or (II), or a stereoisomeric form, hydrate, solvate, pharmaceutically acceptable salt, pharmaceutically acceptable prodrug, or pharmaceutically active metabolite of such compound. In certain preferred embodiments of the inventive method, the disease, disorder, or medical condition is selected from: cognitive disorders, sleep disorders, psychiatric disorders, and other disorders.

Preferred embodiments, features, and advantages of the invention will be apparent from the following detailed description and through practice of the invention.

DETAILED DESCRIPTION OF THE INVENTION AND ITS PREFERRED EMBODIMENTS

The invention may be more fully appreciated by reference to the following detailed description, including the following glossary of terms and the concluding examples. For the sake of brevity, the disclosures of the publications, including patents, cited in this specification are herein incorporated by reference.

The terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which may also be structurally depicted by a bond, "I"), ethyl (Et), n-propyl (Pr), isopropyl (iPr), butyl (nBu), isobutyl (iBu), sec-butyl (sBu), tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities (depicted without their bonds of attachment):

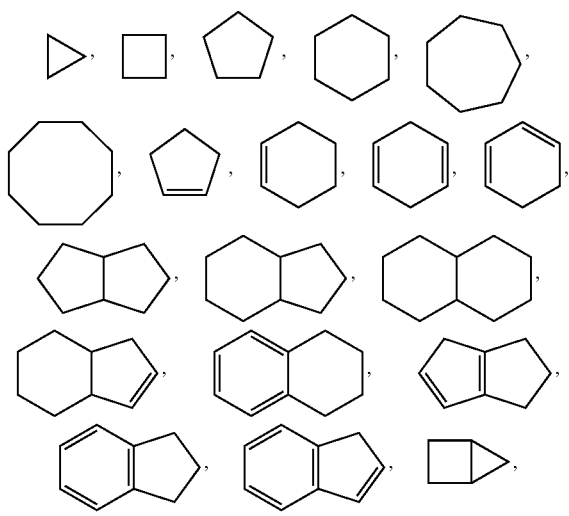

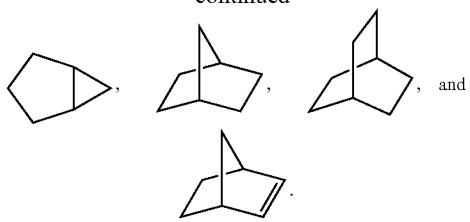

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative examples (depicted without their bonds of attachment) include:

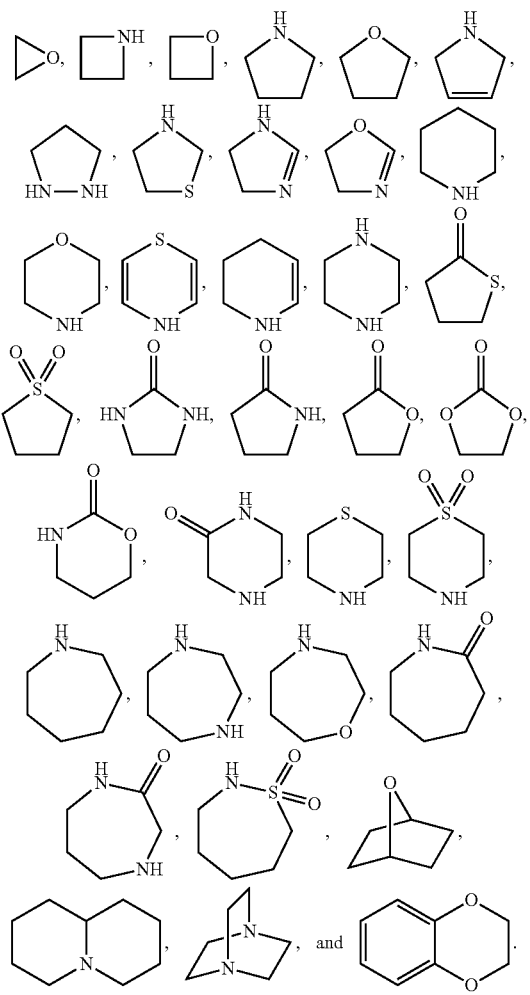

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities (depicted without their bonds of attachment):

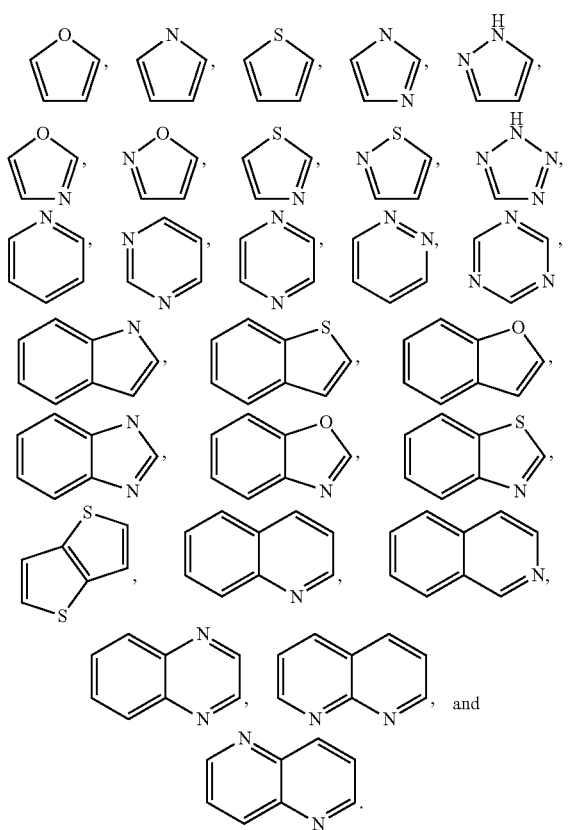

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formulae as well as certain variations or forms. In particular, compounds of any formula given herein may have asymmetric centers and therefore exist in different enantiomeric forms. It is understood that some compounds referred to herein are chiral and/or have geometric isomeric centers, for example E- and Z-isomers. All optical isomers and stereoisomers of the compounds of any general structural formula, and mixtures thereof, are considered within the scope of the formulae. Thus, any general formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any general formula given herein is intended to embrace hydrates, solvates, and polymorphs of such compounds, and mixtures thereof. Furthermore, certain compounds referred to herein can exist in solvated as well as unsolvated forms. It is understood that this invention encompasses all such solvated and unsolvated forms that possess the activity that characterizes the compounds of this invention.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any general formula given herein is also intended to represent unlabeled forms as well as isotopically labeled forms of the compounds. Isotopically labeled compounds have structures of the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^2H$ or $^3H$), detection or imaging techniques (such as positron emission tomography (PET) or single-photon emission computed tomography (SPECT)) including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to a formula given herein, the selection of a particular moiety from a list of possible species for a specified variable is not intended to define the moiety for the variable appearing elsewhere. In other words, where a variable appears more than once in a formula, the choice of the species from a specified list is independent of the choice of the species for the same variable elsewhere in the formula unless otherwise indicated.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, A, $X^4$, $X^5$, $X^6$, $X^7$, $R^a$, $R^b$, $R^c$, $R^d$, $R^e$, $R^f$, $R^g$, $R^h$, $R^i$, $R^j$, $R^k$, $R^l$, $R^m$, and $R^o$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, A, $X^4$, $X^5$, $X^6$, $X^7$, $R^a$, $R^b$, $R^c$, $R^d$, $R^e$, $R^f$, $R^g$, $R^h$, $R^i$, $R^j$, $R^k$, $R^l$, $R^m$, and $R^o$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The compounds of Formulae (I) and (II) and their pharmaceutically acceptable salts, pharmaceutically acceptable prodrugs, and pharmaceutically active metabolites of the present invention are useful as serotonin receptor modulators in the methods of the invention.

A "pharmaceutically acceptable salt" is intended to mean a salt of a free acid or base of a compound represented by Formulae (I) or (II), that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formulae (I) or (II) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formulae (I) or (II) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formulae (I) or (II) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formulae (I) or (II), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formulae (I) or (II). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formulae (I) or (II). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formulae (I) or (II) as amides or alkyl esters. Representative pharmaceutically acceptable amides of the invention include those derived from ammonia, primary $C_{1-6}$ alkyl amines and secondary di($C_{1-6}$alkyl)amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl) amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med. Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formulae (I) or (II), which may also be used in the methods of the invention. A "pharmaceutically active metabolite" means a pharmacologically active product of metabolism in the body of a compound of Formulae (I) or (II) or salt thereof. Prodrugs and active metabolites of a compound may be determined using routine techniques known or available in the art. See, e.g., Bertolini, et al., *J Med. Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formulae (I) or (II) and their pharmaceutically acceptable salts, pharmaceutically acceptable prodrugs, and pharmaceutically active metabolites of the present invention are useful as modulators of the seratonin receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize or down-regulate seratonin receptor expression or activity, and "activators" are compounds that increase, activate, facilitate, sensitize, or up-regulate seratonin receptor expression or activity. Many of the compounds of the present invention are 5-$HT_7$ modulators that act as 5-$HT_7$ agonists. As such, the compounds are useful in the treatment of 5-$HT_7$-mediated disease in which an increase, induction, activation or up-regulation of serotonin receptor expression or activity is required.

The term "treat" or "treating" as used herein is intended to refer to administration of an active agent or composition of the invention to a subject for the purpose of effecting a therapeutic or prophylactic benefit through modulation of serotonin receptor activity. Treating includes reversing, ameliorating, alleviating, inhibiting the progress of, lessening the severity of, or preventing a disease, disorder, or condition, or one or more symptoms of such disease, disorder or condition mediated through modulation of serotonin receptor activity. The term "subject" refers to a mammalian patient in need of such treatment, such as a human.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician.

The invention may be particularly useful in the treatment or prevention of diseases, disorders, or conditions mediated by serotonin receptor activity, such as: central nervous system disorders such as sleep disorders (including insomnia), depression/anxiety, generalized anxiety disorder, schizophrenia, bipolar disorders, cognitive disorders, mild cognitive impairment, Alzheimer's disease, Parkinson's disease, psychotic disorders, phobic disorders, obsessive-compulsive disorder, mood disorders, post-traumatic stress and other stress-related disorders, migraine, pain, eating disorders, obesity, sexual dysfunction, metabolic disturbances, hormonal imbalance, hot flashes associated with menopause, alcohol abuse, drug abuse, and addictive disorders including drug addiction and alcohol addiction. Further diseases associated with serotonin receptor activity for which the compounds may be useful for treating are nausea, inflammation, centrally mediated hypertension, sleep/wake disturbances, jetlag, and circadian rhythm abnormalities. The compounds may also be used in the treatment and prevention of hypotension, peripheral vascular disorders, cardiovascular shock, renal disorders, gastric motility, diarrhea, spastic colon, irritable bowel disorders, ischemias, septic shock, urinary incontinence and other disorders related to the gastrointestinal and vascular systems. In addition, compounds of the present invention may be used in methods for treating or preventing a range of ocular disorders including glaucoma, optic neuritis, diabetic retinopathy, retinal edema, and age-related macular degeneration. Symptoms or disease states are intended to be included within the scope of "medical conditions, disorders, or diseases."

The compounds of the present invention are $5\text{-}HT_7$ modulators, many of which are $5\text{-}HT_7$ agonists. As such, the compounds are useful in the treatment of $5\text{-}HT_7$ mediated disease states. Where the compounds possess substantial $5\text{-}HT_7$ modulating activity, they may be particularly useful in methods for treating depression/anxiety, sleep/wake disturbances, sleep disorders, jet lag, migraine, urinary incontinence, gastric motility, and irritable bowel disorders, hypertension, analgesic, and irritable bowel syndrome.

Particularly, as serotonin receptor modulators, the compounds of the present invention are useful in the treatment or prevention of depression, anxiety, sleep disorders, and circadian rhythm abnormalities.

The compounds of the invention are used, alone or in combination with one or more other active ingredients, to formulate pharmaceutical compositions of the invention. In addition, the compounds of the invention may be used in combination with additional active ingredients in the treatment of the above conditions. In an exemplary embodiment, additional active ingredients are those that are known or discovered to be effective in the treatment of conditions, disorders, or diseases mediated by serotonin receptors or that are active against another target associated with the particular condition, disorder, or disease. Suitable examples include: $H_1$ receptor antagonists, $H_2$ receptor antagonists, $H_3$ receptor antagonists, topiramate (TOPAMAX™), and neurotransmitter modulators such as norepinephrine reuptake inhibitors (NRIs), selective serotonin reuptake inhibitors (SSRIs), noradrenergic reuptake inhibitors, non-selective serotonin re-uptake inhibitors (NSSRIs), acetylcholinesterase inhibitors (such as tetrahydroaminoacridine, Donepezil (ARICEPT™), Rivastigmine, or Galantamine (REMINYL™)), modafinil, antipsychotics, sedatives, monoamine oxidase inhibitors (MAOs), and tricyclic antidepressants (TCAs). The combination may serve to increase efficacy (e.g., by including in the combination a compound potentiating the potency or effectiveness of a compound according to the invention), decrease one or more side effects, or decrease the required dose of the compound according to the invention. In preferred embodiments, the combination method employs doses containing additional active ingredients in the range of about 20 to 300 mg per dose.

A pharmaceutical composition of the invention comprises: (a) an effective amount of a compound of Formulae (I) and (II), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. It is anticipated that the compounds of the invention can be administered by oral or parenteral routes, including intravenous, intramuscular, intraperitoneal, subcutaneous, rectal and topical administration, and inhalation. For oral administration, the compounds of the invention will generally be provided in the form of tablets or capsules or as an aqueous solution or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate and lactose. Cornstarch and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Effective doses of the compounds of the present invention may be ascertained by conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.01 to 1000 mg per day, more usually from 1 to 500 mg per day, and most usually from 10 to 200 mg per day. Expressed as dosage per unit body weight, a typical dose will be expected to be between 0.0001 mg/kg and 15 mg/kg, especially between 0.01 mg/kg and 7 mg/kg, and most especially between 0.15 mg/kg and 2.5 mg/kg.

The invention includes also pharmaceutically acceptable salts of the compounds represented by Formulae (I) or (II), preferably of those described below. Pharmaceutically acceptable salts of the specific compounds exemplified herein are especially preferred.

In certain embodiments of compounds of the invention, chemical entities are of the formula (I). In further embodiments of the invention, chemical entities are of the formula (II).

In certain preferred embodiments of compounds of Formulae (I) or (II), m has the value of 1 or 2 and n has the value of 1 or 2; however, if m is 2 then n is not 1. In preferred embodiments, m is 1 and n is 1. In further preferred embodiments, m is 1 and n is 2. In further preferred embodiments, m is 2 and n is 2. In certain embodiments, compounds are of Formula (II) and m and n are each 1.

In certain embodiments of compounds of Formulae (I) or (II), L is either absent or is an —O—. In certain embodiments of the invention, L is absent. In further embodiments, L is —O—.

In certain embodiments of compounds of Formulae (I) or (II), $R^1$ is —H, —$C_{1-4}$alkyl, or $C_{3-6}$cycloalkyl. In preferred embodiments, $R^1$ is hydrogen, methyl, isopropyl, or cyclobutyl. In further preferred embodiments, $R^1$ is Hydrogen.

In certain embodiments of compounds of Formulae (I) or (II), $R^2$ is selected from —H, halo, —CN, —$OCF_3$, —$OCH_2CF_3$, —$OC_{1-4}$alkyl, —$C_{3-6}$cycloalkoxy, —$OCH_2C_{3-6}$cycloalkyl, —$C(O)N(R_a)_2$, or —$C(O)R_b$ wherein each $R_a$ is individually —H or —$C_{1-4}$alkyl and $R_b$ is —$C_{1-4}$alkyl, —$C_{3-6}$cycloalkyl, or —$CH_2C_{3-6}$cycloalkyl. In further embodiments, the $R^2$ substituent is selected from —H, —Cl, —$OCH_3$, —$OCH_2CH_3$, —CN, —$OCF_3$, cyclobutoxy, cyclopropylmethoxy, isopropoxy, or —$C(O)N(CH_2CH_3)$.

In certain preferred embodiments of compounds of Formulae (I) or (II), $R^3$ is —H or —$C_{1-4}$alkyl. In further preferred embodiments, $R^3$ is —H, or —$CH_3$.

In certain preferred embodiments of compounds of Formulae (I) or (II), o is 0, 1, or 2. In various preferred embodiments, o is 1. In further preferred embodiments, o is 2.

In certain preferred embodiments of compounds of Formulae (I) or (II), each $R^4$ is independently selected from —H, halo, —$C_{1-4}$alkyl, —$C_{1-4}$alkoxy, —$OCF_3$, —$CF_3$, or —CN. In further embodiments, each $R^4$ is independently selected from hydrogen, chloro, fluoro, —$CH_3$, —$CF_3$, —$OCF_3$, —$OCH_3$, and —CN.

Preferred compounds, which are biphenyls, are selected from the group consisting of:

| Ex | Chemical Name |
|---|---|
| 1 | 3-(2-Benzyloxy-5-bromo-phenoxy)-azetidine; |
| 2 | 3-(4'-Fluoro-4-methoxy-2'-methyl-biphenyl-3-yloxy)-azetidine; |
| 3 | 3'-(Azetidin-3-yloxy)-4'-methoxy-biphenyl-2-carbonitrile trifluoroacetate; |
| 4 | 3-(4-Methoxy-2',3'-dimethyl-biphenyl-3-yloxy)-azetidine; |
| 5 | 3-(3'-Fluoro-4-methoxy-2'-methyl-biphenyl-3-yloxy)-azetidine; |
| 6 | 3-(4-Methoxy-2',6'-dimethyl-biphenyl-3-yloxy)-azetidine trifluoroacetate; |
| 7 | 3-(4-Methoxy-2'-trifluoromethoxy-biphenyl-3-yloxy)-azetidine; |
| 8 | 3-(4-Methoxy-2'-methyl-biphenyl-3-yloxy)-azetidine trifluoroacetate; |
| 9 | 3-(4,2'-Dimethoxy-biphenyl-3-yloxy)-azetidine; |
| 10 | 3-(2'-Chloro-4-methoxy-6'-trifluoromethyl-biphenyl-3-yloxy)-azetidine trifluoroacetate; |
| 11 | 3-(4-Methoxy-4'-methyl-biphenyl-3-yloxy)-azetidine; |
| 12 | 3-(4'-Fluoro-4-methoxy-3'-methyl-biphenyl-3-yloxy)-azetidine; |
| 13 | 3-(4-Methoxy-3'-methyl-biphenyl-3-yloxy)-azetidine; |
| 14 | 3-(4-Methoxy-3',4'-dimethyl-biphenyl-3-yloxy)-azetidine; |
| 15 | 3-(4-Methoxy-biphenyl-3-yloxy)-azetidine; |
| 16 | 3-(4-Methoxy-2',5'-dimethyl-biphenyl-3-yloxy)-azetidine; |
| 17 | 3-(2'-Chloro-4-methoxy-biphenyl-3-yloxy)-azetidine; |
| 18 | 3-(2'-Chloro-4-methoxy-biphenyl-3-yloxy)-1-isopropyl-azetidine trifluoroacetate; |
| 19 | 3-(2'-Chloro-4-methoxy-biphenyl-3-yloxy)-1-cyclobutyl-azetidine trifluoroacetate; |
| 20 | 3-(2'-Trifluoromethyl-biphenyl-3-yloxy)-azetidine; |
| 21 | 3-(2'-Chloro-biphenyl-3-yloxy)-azetidine; |
| 22 | 3-(3'-Methyl-biphenyl-3-yloxy)-azetidine; |
| 23 | 3-(2'-Methyl-biphenyl-3-yloxy)-azetidine; |
| 24 | 3-(4,2'-Dichloro-biphenyl-3-yloxy)-azetidine trifluoroacetate; |
| 25 | 3-(4-Chloro-2'-trifluoromethyl-biphenyl-3-yloxy)-azetidine trifluoroacetate; |
| 26 | 3-(4-Chloro-2'-methyl-biphenyl-3-yloxy)-azetidine trifluoroacetate; |
| 27 | 3-(4-Chloro-3'-methyl-biphenyl-3-yloxy)-azetidine trifluoroacetate; |
| 28 | 3-(Azetidin-3-yloxy)-2'-trifluoromethyl-biphenyl-4-carbonitrile; |
| 29 | 3-(Azetidin-3-yloxy)-biphenyl-4-carbonitrile; |
| 30 | 3-(Azetidin-3-yloxy)-2'-methyl-biphenyl-4-carbonitrile; |
| 31 | 5-(Azetidin-3-yloxy)-2-methyl-biphenyl-4-carbonitrile; |
| 32 | 3-(4-Ethoxy-2'-methyl-biphenyl-3-yloxy)-azetidine hydrochloride; |
| 33 | 3-[2'-Methyl-4-(2,2,2-trifluoro-ethoxy)-biphenyl-3-yloxy]-azetidine; |
| 34 | 3-(4-Cyclobutoxy-2'-methyl-biphenyl-3-yloxy)-azetidine; |
| 35 | 3-(4-Cyclopropylmethoxy-2'-methyl-biphenyl-3-yloxy)-azetidine; |
| 36 | 3-(4-lsopropoxy-2'-methyl-biphenyl-3-yloxy)-azetidine; |
| 37 | 3-(Azetidin-3-yloxy)-2'-trifluoromethyl-biphenyl-4-carboxylic acid diethylamide; |
| 38 | 3-(4-Chloro-3'-methyl-biphenyl-2-yloxy)-azetidine; |
| 39 | 3-(4-Chloro-2'-methyl-biphenyl-2-yloxy)-azetidine; |
| 40 | 3-(4-Chloro-3'-trifluoromethyl-biphenyl-2-yloxy)-azetidine; |
| 41 | 3-(4-Chloro-4'-fluoro-3'-methyl-biphenyl-2-yloxy)-azetidine; |
| 42 | 3-(4-Chloro-3',4'-dimethyl-biphenyl-2-yloxy)-azetidine; |
| 43 | (±)-3-(4-Methoxy-2'-methyl-biphenyl-3-yl)-pyrrolidine; |
| 44 | (±)-3-(3'-Fluoro-4-methoxy-2'-methyl-biphenyl-3-yl)-pyrrolidine; |
| 45 | (±)-3-(2',3'-Difluoro-4-methoxy-biphenyl-3-yl)-pyrrolidine; |
| 46 | (±)-3-(4-Methoxy-3'-trifluoromethyl-biphenyl-3-yl)-pyrrolidine; |
| 47 | (±)-3-(4-Methoxy-2'-trifluoromethyl-biphenyl-3-yl)-pyrrolidine; |
| 48 | (±)-3-(4-Methoxy-2'-trifluoromethoxy-biphenyl-3-yl)-pyrrolidine; |
| 49 | (±)-3-(4-Methoxy-biphenyl-3-yl)-pyrrolidine; |
| 50 | (±)-3-(4-Methoxy-biphenyl-3-yl)-1-methyl-pyrrolidine; |
| 51 | (±)-3-Biphenyl-2-yl-pyrrolidine; |
| 52 | (±)-3-(3'-Methyl-biphenyl-2-yl)-pyrrolidine; |
| 53 | (±)-3-(4'-Methyl-biphenyl-2-yl)-pyrrolidine; |

| Ex | Chemical Name |
|---|---|
| 54 | 3-(4'-Chloro-biphenyl-2-yl)-pyrrolidine; |
| 55 | (±)-3-(3',4'-Dimethyl-biphenyl-2-yl)-pyrrolidine; |
| 56 | (±)-3-(3',4'-Dimethyl-biphenyl-2-yl)-1-methyl-pyrrolidine; |
| 57 | (±)-3-(2'-Methyl-biphenyl-2-yl)-pyrrolidine; |
| 58 | (±)-1-Methyl-3-(2'-methyl-biphenyl-2-yl)-pyrrolidine; |
| 59 | (±)-3-(2'-Methoxy-biphenyl-2-yl)-pyrrolidine; |
| 60 | (±)-1-Methyl-3-(4'-methyl-biphenyl-2-yl)-pyrrolidine; |
| 61 | (±)-1-Methyl-3-(3'-methyl-biphenyl-2-yl)-pyrrolidine; |
| 62 | (±)-3-(2'-Methoxy-5'-methyl-biphenyl-2-yl)-pyrrolidine; |
| 63 | (±)-3-(2'-Methoxy-5'-methyl-biphenyl-2-yl)-1-methyl-pyrrolidine; |
| 64 | (±)-3-(2'-Methoxy-biphenyl-2-yl)-1-methyl-pyrrolidine; |
| 65 | (±)-3-(4,3'-Dichloro-biphenyl-2-yl)-pyrrolidine; |
| 66 | (±)-3-(4-Chloro-4'-fluoro-3'-methyl-biphenyl-2-yl)-pyrrolidine; |
| 67 | (±)-3-(4-Chloro-3',4'-dimethyl-biphenyl-2-yl)-pyrrolidine; |
| 68 | 4-(4-Methoxy-biphenyl-3-yloxy)-piperidine; and |
| 69 | 4-(4-Methoxy-2'-trifluoromethyl-biphenyl-3-yloxy)-piperidine | and stereoisomeric forms, hydrates, solvates, pharmaceutically acceptable salts, prodrugs, and active metabolites thereof.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables in the formulas depicted in the schemes below are as defined above in reference to Formulae (I) and (II). Reactions may be performed between the melting point and the reflux temperature of the solvent, and preferably between 0° C. and the reflux temperature of the solvent.

List of abbreviations: Ac=Acetyl, AIBN=azobisisobutyronitrile, Boc=tert-Butylcarbamoyl, m-CPBA=meta-chloroperoxybenzoic acid, DCE=dichloroethane, DEAD=diethyldiazodicarboxylate, DIBAL-H=diisobutyl aluminum hydride, DIEA=N,N-Diisopropylethylamine, DMA=N,N-Dimethylacetamide, DME=Ethylene glycol dimethyl ether, DMF=dimethylformamide, DMSO=Dimethyl sulfoxide, Et$_3$N=triethylamine, Et$_2$O=diethyl ether, EtOAc=Ethyl acetate, MeCN=acetonitrile, MeOH=methanol, MsCl=Methanesulfonyl chloride, TFA=trifluoroacetic acid, TFAA=trifluoroacetic acid anhydride, THF=tetrahydrofuran, TLC=thin layer chromatography, Q-Phos=1,2,3,4,5-pentaphenyl-1'-(di-tert-butylphosphino)ferrocene.

The biphenyl compounds of formulas (I) and (II) may be prepared by a number of reaction schemes. Preparation of compounds of formula (I) is described in Schemes A and H. Preparation of compounds of formula (II) is described in Schemes B, C, D, E, F, and G. Persons skilled in the art may recognize that certain compounds are more advantageously produced by one scheme as compared to the other.

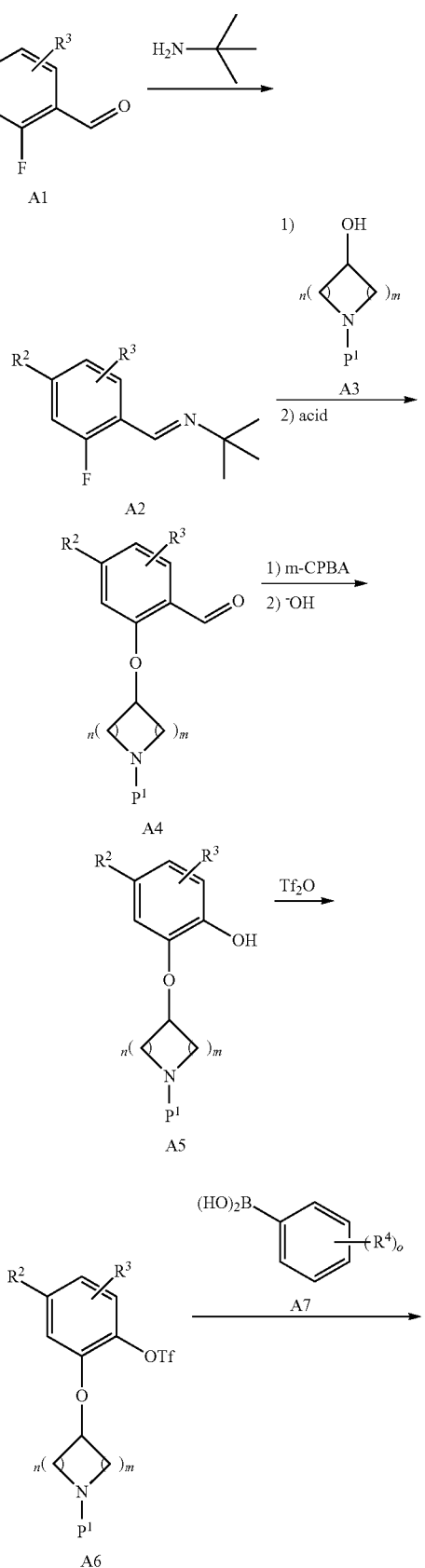

Scheme A

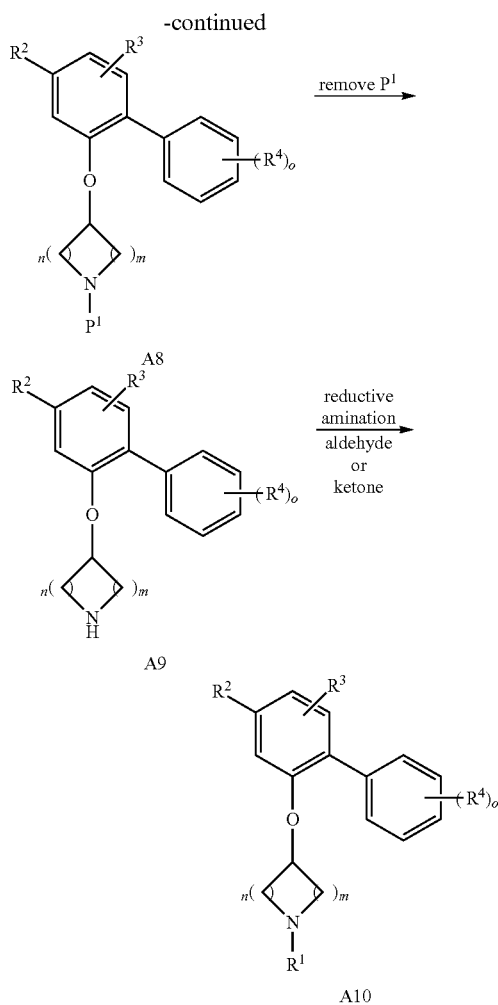

A8

A9

A10

Intermediates of formula A10 were prepared according to Scheme A. Compounds of formula A1 were treated with tert-butylamine in the presence of a dehydrating agent such as $SiO_2$, $CuSO_4$, $Ti(OiPr)_4$, $MgSO_4$ or molecular sieves in a suitable solvent such as THF, $CH_2Cl_2$, benzene, toluene, MeOH or EtOH. In preferred embodiments, $MgSO_4$ in $CH_2Cl_2$ was used to give compounds of formula A2. Compounds of formula A4 were obtained from compounds of formula A2 using compounds of formula A3 in a suitable solvent such as DMF, DMSO, NMP or THF in the presence of a base such as NaH, KOtBu or $Cs_2CO_3$, preferably NaH in DMF. Compounds of formula A5 were obtained from compounds of formula A4 upon basic hydrolysis of the compound obtained from the treatment of compounds of formula A5 with an oxidant such as m-chloroperoxybenzoic acid (m-CPBA) in $CH_2Cl_2$. The hydrolysis is performed using a base such as NaOH or KOH in a solvent such as MeOH, EtOH or $H_2O$. One skilled in the art will recognize that compounds of formula A5 can be converted into precursors for transition-metal catalyzed cross-coupling reactions, such as Stille, Suzuki, Negishi, Sonagashira or other such coupling reactions known to one skilled in the art. For example, treatment of compounds of the formula A5 with a triflating agent such as trifluoromethanesulfonic anhydride ($Tf_2O$) or N-phenyltrifluoromethanesulfonamide in DCE, $CH_2Cl_2$, THF or the like in the presence of a base such as pyridine, triethylamine or diisopropylethylamine provides compounds of the formula A6. Treatment of compounds of formula A6 with organoboron compounds A7 in the presence of a catalyst such as $PdCl_2(dppf)$, $PdCl_2(dppe)$ $Pd_2(dba)_3$, $Pd(dba)_2$, $PdCl_2(PPh_3)_2$, $Pd(PPh_3)_4$ in a solvent such as $PhCH_3$, 1,4-dioxane, THF, DMA, DMF or DME in the presence of a base such as $Na_2CO_3$, $K_2CO_3$, $Cs_2CO_3$, CsF, KF, $K_3PO_4$, KOAc or the like and a ligand typically used in such reactions such as Q-Phos, dppf, dppe or $PPh_3$ and the like affords compounds of formula A8 at temperatures ranging from rt to 160° C. using conventional or microwave heating.

The amine in compounds of formula A8 may be protected, as indicated by $P^1$, as an alkyl or benzyl amine, amide, carbamate or other groups such as described in "Protecting Groups in Organic Synthesis", $3^{rd}$ ed.; T. W. Greene and P. G. Wuts, John Wiley and Sons, 1999. Preferably, $P^1$ is —$C_{1-6}$Alkyl, —$COOC_{1-6}$Alkyl, —(C═O)$C_{1-6}$Alkyl, benzyl substituted or unsubstituted with —$OC_{1-6}$Alkyl or $C_{1-6}$Alkyl, or benzhydryl substituted or unsubstituted with —$OC_{1-6}$Alkyl or $C_{1-6}$Alkyl). A further preferred protecting group is t-butyl carbamate (Boc) or trifluoroacetamide. This protecting group ($P^1$) on the nitrogen may be removed using generally accepted methods or may be converted directly into compounds of the formula A10. More specifically a group such as a Boc group may be removed with an acid such as trifluoroacetic acid or hydrochloric acid and the like in a solvent such as $CH_2Cl_2$, EtOAc, THF, 1,4-dioxane, MeOH or EtOH. A group such as trifluoroacetamide was removed using a base such as $NH_3$, $NH_4OH$ or $K_2CO_3$ in an alcoholic solvent such as MeOH or EtOH and the like.

It will be generally recognized that compounds of the formula A9 represent a subset of compounds of formula A10 where $R^1$ is equal to H. Compounds of formula A9 or A10 may be converted to their corresponding salts using methods generally accepted to those skilled in the art.

Compounds such as A10 were prepared from compounds of the formula A9 using methods such as reductive amination or alkylation. Thus treatment of A9 with a compound of formula an aldehyde or ketone in the presence of a reductant such as $NaBH_4$, $NaBH_3CN$, $NaBH(OAc)_3$ or hydrogen gas in the presence of a catalyst in a solvent such as $CH_2Cl_2$, THF, DCE, MeOH, EtOH or similar afforded compounds of formula A10. One skilled in the art will recognize that the addition of acid to decrease the pH of the reaction mixture to less than pH 7 may be required. Examples of acids may include AcOH, $Ti(O-iPr)_4$, trifluoroacetic acid or hydrochloric acid and the like. One skilled in the art will also recognize that compounds of formula A10 may be obtained from A9 upon treatment with an alkyl chloride, bromide, iodide, mesylate or tosylate and the like in a solvent such as DMF, DMA, THF or EtOH in the presence of bases such as $NaHCO_3$, $Na_2CO_3$, $K_2CO_3$ or $Cs_2CO_3$.

Scheme B

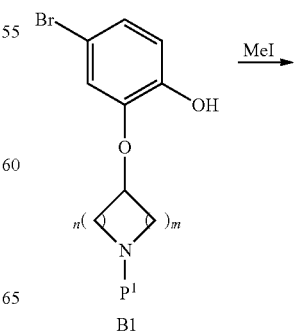

B1

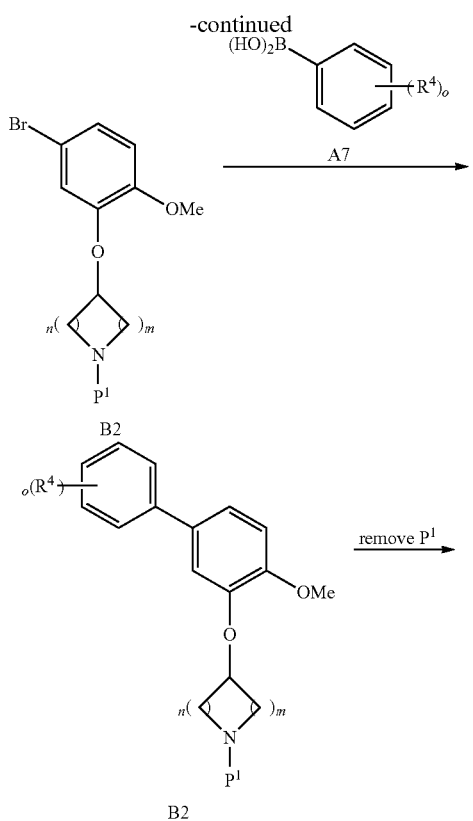

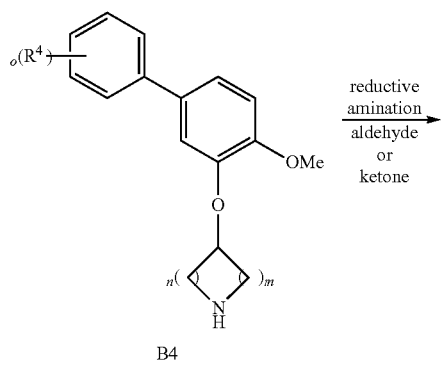

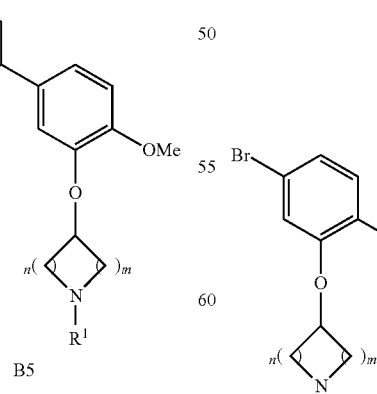

of the formula B2 were obtained from compounds of the formula B1 upon treatment with methyl iodide in a solvent such as DMF, DMA, THF or EtOH in the presence of bases such as NaHCO$_3$, Na$_2$CO$_3$, K$_2$CO$_3$ or Cs$_2$CO$_3$. One skilled in the art will recognize that compounds of formula B2 can be utilized for transition-metal catalyzed cross-coupling reactions as previously described. Treatment of compounds of formula B2 with organoboron compounds A7 in the presence of a catalyst such as PdCl$_2$(dppf), PdCl$_2$(dppe) Pd$_2$(dba)$_3$, Pd(dba)$_2$, PdCl$_2$(PPh$_3$)$_2$, Pd(PPh$_3$)$_4$ in a solvent such as PhCH$_3$, 1,4-dioxane, THF, DMA, DMF or DME in the presence of a base such as Na$_2$CO$_3$, K$_2$CO$_3$, Cs$_2$CO$_3$, CsF, KF, K$_3$PO$_4$, KOAc or the like and a ligand typically used in such reactions such as Q-Phos, dppf, dppe or PPh$_3$ and the like affords compounds of formula B3 at temperatures ranging from rt to 160° C. using conventional or microwave heating.

The amine in compounds of formula B3 may be protected with a protecting group, as indicated by P$^1$, with previously described protecting groups. A preferred protecting group is t-butyl carbamate (Boc) or trifluoroacetamide. The protecting group (P$^1$) on the nitrogen may be removed as previously described or may be converted directly into compounds of the formula B5. It will be generally recognized that compounds of the formula B4 represent a subset of compounds of formula B5 where R$^1$ is equal to H. Compounds of formula B4 or B5 may be converted to their corresponding salts using methods generally accepted to those skilled in the art.

Compounds such as B5 may be prepared from compounds of the formula B4 using methods such as reductive amination or alkylation. Thus treatment of B4 with a compound containing a carbonyl, such as an aldehyde or ketone, in the presence of a reductant such as NaBH$_4$, NaBH$_3$CN, NaBH(OAc)$_3$ or, hydrogen gas and presence of a catalyst, in a solvent such as CH$_2$Cl$_2$, THF, DCE, MeOH, EtOH or similar affords compounds of formula B5. One skilled in the art will recognize that the addition of acid to decrease the pH of the reaction mixture to less than pH 7 may be required. One skilled in the art will also recognize that compounds of formula B5 may be obtained from B4 upon treatment with an alkyl chloride, bromide, iodide, mesylate or tosylate and the like in a solvent such as DMF, DMA, THF or EtOH in the presence of bases such as NaHCO$_3$, Na$_2$CO$_3$, K$_2$CO$_3$ or Cs$_2$CO$_3$.

Scheme C

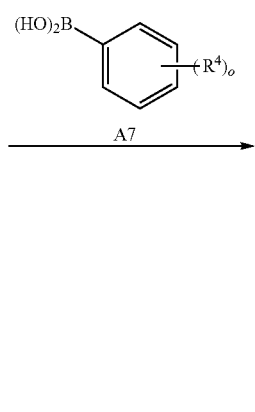

Intermediates of formula B5 were prepared according to Scheme B. Compounds of the formula B1 were prepared similar to compounds of formula A5 (Scheme 1). Compounds

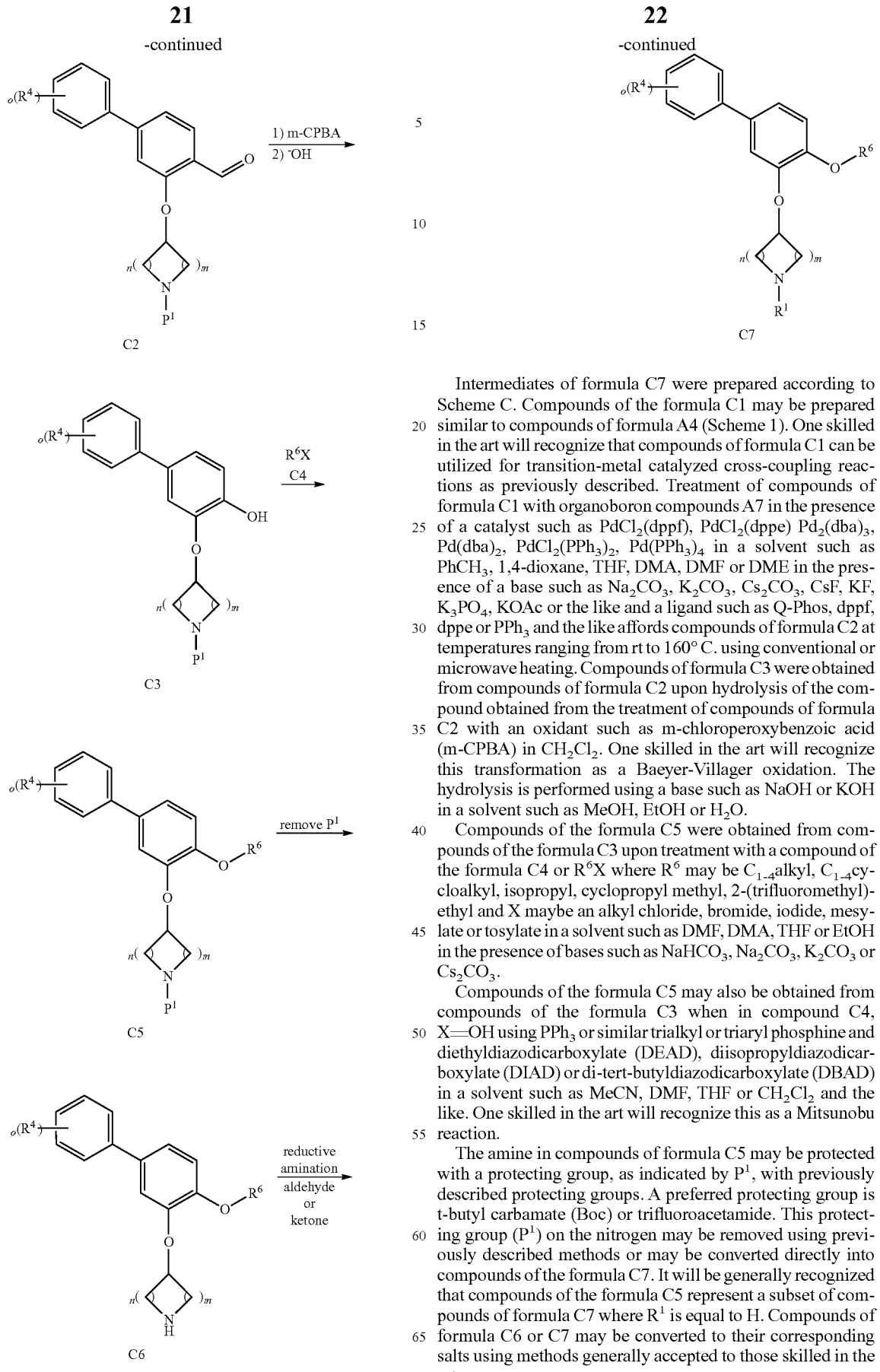

Intermediates of formula C7 were prepared according to Scheme C. Compounds of the formula C1 may be prepared similar to compounds of formula A4 (Scheme 1). One skilled in the art will recognize that compounds of formula C1 can be utilized for transition-metal catalyzed cross-coupling reactions as previously described. Treatment of compounds of formula C1 with organoboron compounds A7 in the presence of a catalyst such as $PdCl_2(dppf)$, $PdCl_2(dppe)$ $Pd_2(dba)_3$, $Pd(dba)_2$, $PdCl_2(PPh_3)_2$, $Pd(PPh_3)_4$ in a solvent such as $PhCH_3$, 1,4-dioxane, THF, DMA, DMF or DME in the presence of a base such as $Na_2CO_3$, $K_2CO_3$, $Cs_2CO_3$, CsF, KF, $K_3PO_4$, KOAc or the like and a ligand such as Q-Phos, dppf, dppe or $PPh_3$ and the like affords compounds of formula C2 at temperatures ranging from rt to 160° C. using conventional or microwave heating. Compounds of formula C3 were obtained from compounds of formula C2 upon hydrolysis of the compound obtained from the treatment of compounds of formula C2 with an oxidant such as m-chloroperoxybenzoic acid (m-CPBA) in $CH_2Cl_2$. One skilled in the art will recognize this transformation as a Baeyer-Villager oxidation. The hydrolysis is performed using a base such as NaOH or KOH in a solvent such as MeOH, EtOH or $H_2O$.

Compounds of the formula C5 were obtained from compounds of the formula C3 upon treatment with a compound of the formula C4 or $R^6X$ where $R^6$ may be $C_{1-4}$alkyl, $C_{1-4}$cycloalkyl, isopropyl, cyclopropyl methyl, 2-(trifluoromethyl)-ethyl and X maybe an alkyl chloride, bromide, iodide, mesylate or tosylate in a solvent such as DMF, DMA, THF or EtOH in the presence of bases such as $NaHCO_3$, $Na_2CO_3$, $K_2CO_3$ or $Cs_2CO_3$.

Compounds of the formula C5 may also be obtained from compounds of the formula C3 when in compound C4, X=OH using $PPh_3$ or similar trialkyl or triaryl phosphine and diethyldiazodicarboxylate (DEAD), diisopropyldiazodicarboxylate (DIAD) or di-tert-butyldiazodicarboxylate (DBAD) in a solvent such as MeCN, DMF, THF or $CH_2Cl_2$ and the like. One skilled in the art will recognize this as a Mitsunobu reaction.

The amine in compounds of formula C5 may be protected with a protecting group, as indicated by $P^1$, with previously described protecting groups. A preferred protecting group is t-butyl carbamate (Boc) or trifluoroacetamide. This protecting group ($P^1$) on the nitrogen may be removed using previously described methods or may be converted directly into compounds of the formula C7. It will be generally recognized that compounds of the formula C5 represent a subset of compounds of formula C7 where $R^1$ is equal to H. Compounds of formula C6 or C7 may be converted to their corresponding salts using methods generally accepted to those skilled in the art.

Compounds such as C7 were prepared from compounds of the formula C6 using methods such as reductive amination or alkylation. Thus treatment of C6 with a compound containing a carbonyl, such as an aldehyde or ketone, in the presence of a reductant such as NaBH$_4$, NaBH$_3$CN, NaBH(OAc)$_3$ or hydrogen gas in the presence of a catalyst in a solvent such as CH$_2$Cl$_2$, THF, DCE, MeOH, EtOH or similar affords compounds of formula C7. One skilled in the art will recognize that the addition of acid to decrease the pH of the reaction mixture to less than pH 7 may be required. One skilled in the art will also recognize that compounds of formula C7 may be obtained from C6 upon treatment with an alkyl chloride, bromide, iodide, mesylate or tosylate and the like in a solvent such as DMF, DMA, THF or EtOH in the presence of bases such as NaHCO$_3$, Na$_2$CO$_3$, K$_2$CO$_3$ or Cs$_2$CO$_3$.

Scheme D

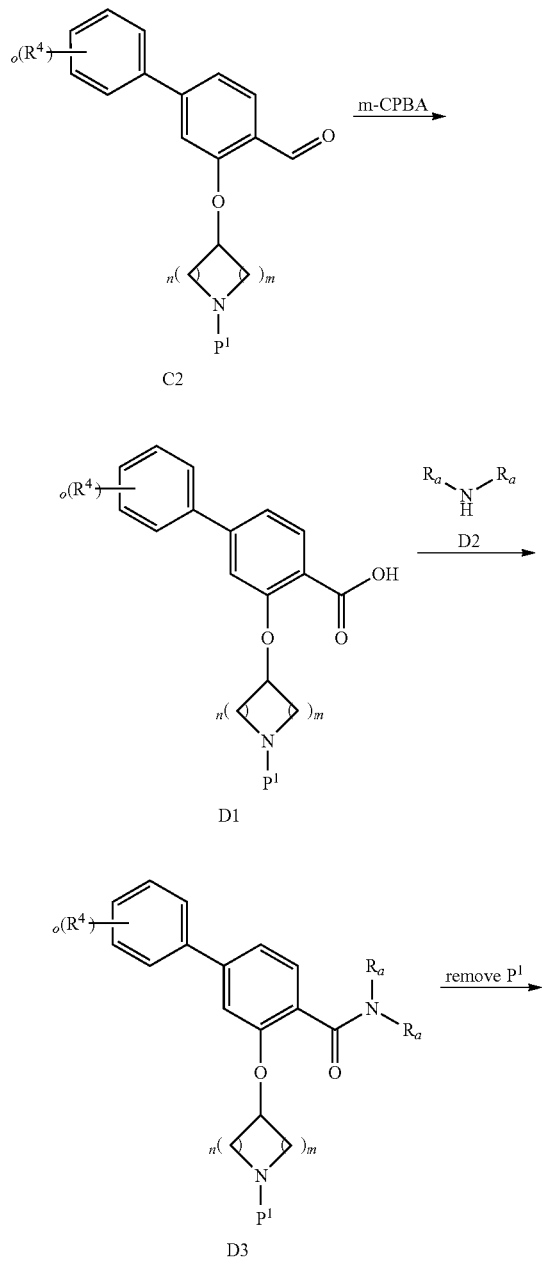

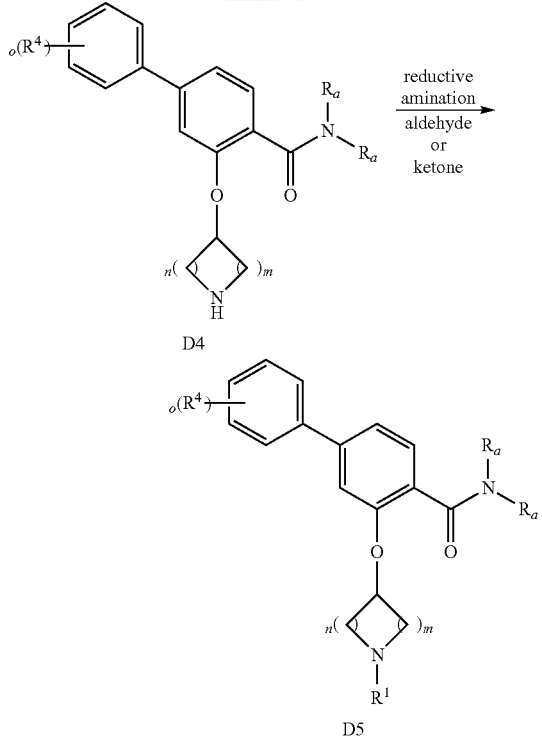

Intermediates of formula D5 were prepared according to Scheme D. Compounds of the formula C2 were prepared similar to compounds of formula A4 (Scheme 1). Compounds of formula D1 were obtained from compounds of formula C2 by treatment with an oxidant such as m-chloroperoxybenzoic acid (m-CPBA) in CH$_2$Cl$_2$. One skilled in the art will recognize that compounds of formula D1 may be converted to compounds of formula D3 using amines D2 in the presence of a amide coupling reagent such as EDC.HCl, HATU, PyBOP or the like and a base such as pyridine, triethylamine or diisopropylethylamine or the like in a suitable solvent such as DMF, CH$_2$Cl$_2$, THF or MeCN or the like.

The amine in compounds of formula D3 may be protected as indicated by P$^1$, with previously described protecting groups. A preferred protecting group is t-butyl carbamate (Boc) or trifluoroacetamide. This protecting group (P$^1$) on the nitrogen may be removed as previously described or may be converted directly into compounds of the formula D5. It will be generally recognized that compounds of the formula D4 represent a subset of compounds of formula D5 where R$^1$ is equal to H. Compounds of formula D4 or D5 may be converted to their corresponding salts using methods generally accepted to those skilled in the art.

Compounds such as D5 were prepared from compounds of the formula D4 using methods such as reductive amination or alkylation. Thus treatment of D4 with a compound containing a carbonyl, such as an aldehyde or ketone, in the presence of a reductant such as NaBH$_4$, NaBH$_3$CN, NaBH(OAc)$_3$ or hydrogen gas in the presence of a catalyst in a solvent such as CH$_2$Cl$_2$, THF, DCE, MeOH, EtOH or similar affords compounds of formula D5. One skilled in the art will recognize that the addition of acid to decrease the pH of the reaction mixture to less than pH 7 may be required. One skilled in the art will also recognize that compounds of formula D5 may be obtained from D4 upon treatment with an alkyl chloride, bromide, iodide, mesylate or tosylate and the like in a solvent such as DMF, DMA, THF or EtOH in the presence of bases such as NaHCO$_3$, Na$_2$CO$_3$, K$_2$CO$_3$ or Cs$_2$CO$_3$ and the like.

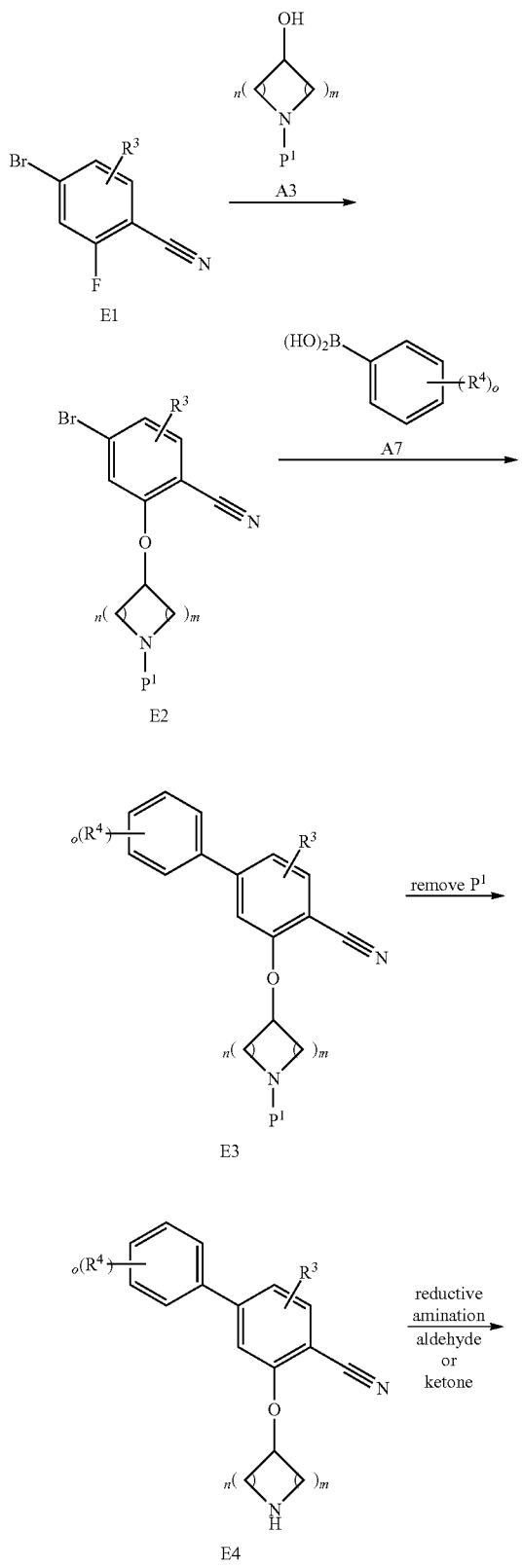

Scheme E

Intermediates of formula E5 were prepared according to Scheme E. Compounds of formula E3 were synthesized from compounds of formula E1. Compounds of formula E2 may be obtained from compounds of formula E1 using a compound of formula A3 in a suitable solvent such as DMF, DMSO, NMP or THF in the presence of a base such as NaH, KOtBu or Cs$_2$CO$_3$, preferably NaH in DMF. One skilled in the art will recognize that compounds of formula E2 can be utilized for transition-metal catalyzed cross-coupling reactions as previously described. Treatment of compounds of formula E2 with organoboron compounds A7 in the presence of a catalyst such as PdCl$_2$(dppf), PdCl$_2$(dppe) Pd$_2$(dba)$_3$, Pd(dba)$_2$, PdCl$_2$(PPh$_3$)$_2$, Pd(PPh$_3$)$_4$ in a solvent such as PhCH$_3$, 1,4-dioxane, THF, DMA, DMF or DME in the presence of a base such as Na$_2$CO$_3$, K$_2$CO$_3$, Cs$_2$CO$_3$, CsF, KF, K$_3$PO$_4$, KOAc or the like and a ligand such as Q-Phos, dppf, dppe or PPh$_3$ and the like affords compounds of formula E3 at temperatures ranging from rt to 160° C. using conventional or microwave heating.

Referring to Scheme 5, compounds of formula E4 were prepared from compounds of formula E3. The amine in compounds of formula E3 may be protected with a protecting group, as indicated by P$^1$, with previously described protecting groups. A preferred protecting group is t-butyl carbamate (Boc) or trifluoroacetamide. This protecting group (P$^1$) on the nitrogen may be removed using previously described methods or may be converted directly into compounds of the formula E5. It will be generally recognized that compounds of the formula E4 represent a subset of compounds of formula E5 where R$^1$ is equal to H. Compounds of formula E4 or E5 may be converted to their corresponding salts using methods generally accepted to those skilled in the art.

Compounds such as E5 were prepared from compounds of the formula E4 using methods such as reductive amination or alkylation. Thus treatment of E4 with a compound containing a carbonyl, such as an aldehyde or ketone, in the presence of a reductant such as NaBH$_4$, NaBH$_3$CN, NaBH(OAc)$_3$ or hydrogen gas in the presence of a catalyst in a solvent such as CH$_2$Cl$_2$, THF, DCE, MeOH, EtOH or similar affords compounds of formula E5. One skilled in the art will recognize that the addition of acid to decrease the pH of the reaction mixture to less than pH 7 may be required. One skilled in the art will also recognize that compounds of formula E5 may be obtained from E4 upon treatment with an alkyl chloride, bromide, iodide, mesylate or tosylate and the like in a solvent such as DMF, DMA, THF or EtOH in the presence of bases such as NaHCO$_3$, Na$_2$CO$_3$, K$_2$CO$_3$ or Cs$_2$CO$_3$ and the like.

Scheme F

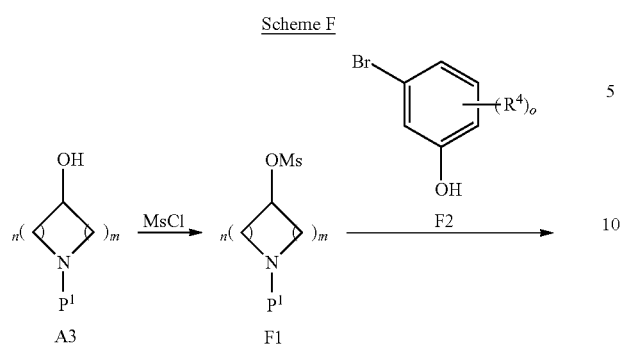

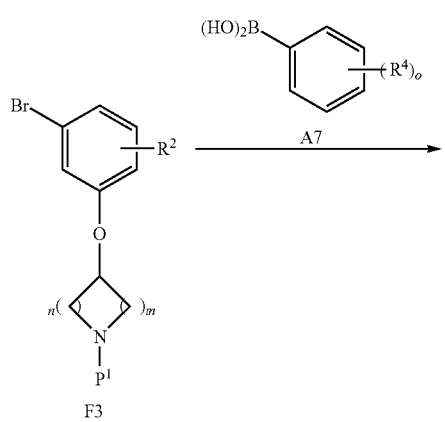

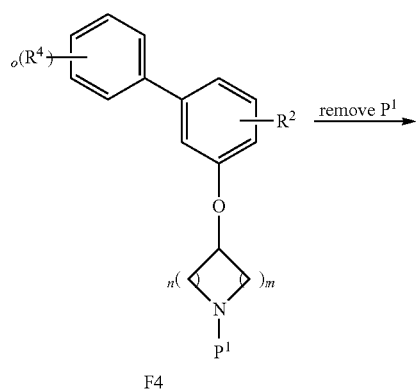

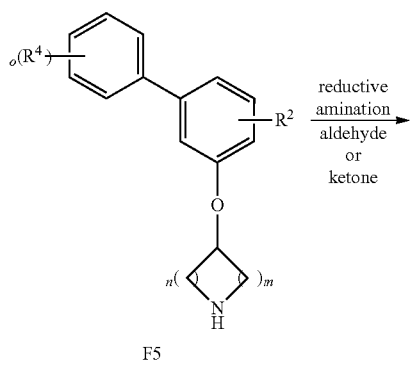

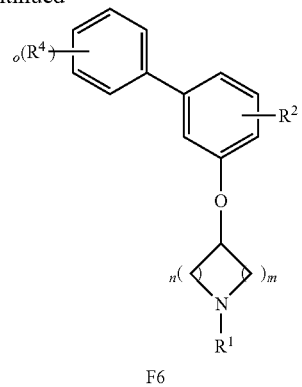

Intermediates of formula F6 were prepared according to Scheme F. Compounds of formula F4 were synthesized from compounds of formula A3. Treatment of a compound of formula A3 with methanesulfonyl chloride in the presence of a base such as pyridine, triethylamine or diisopropylamine in a solvent such as $CH_2Cl_2$, THF or DCE yields compounds of formula F1. Treatment of a compound of formula F1 with a nucleophile such as a compound of formula F2 in the presence of base such as pyridine, triethylamine, diisopropylamine, $K_2CO_3$, $Cs_2CO_3$ or $Na_2CO_3$ in a suitable solvent such as THF, $CH_2Cl_2$, DMF, MeCN, 1,4-dioxane or the like at a temperature ranging from rt to 100° C. provides compounds of the formula F3.

One skilled in the art will recognize that compounds of formula F3 can be utilized for transition-metal catalyzed cross-coupling reactions as previously described. Treatment of compounds of formula F3 with organoboron compounds A7 in the presence of a catalyst such as $PdCl_2(dppf)$, $PdCl_2(dppe)$ $Pd_2(dba)_3$, $Pd(dba)_2$, $PdCl_2(PPh_3)_2$, $Pd(PPh_3)_4$ in a solvent such as $PhCH_3$, 1,4-dioxane, THF, DMA, DMF or DME in the presence of a base such as $Na_2CO_3$, $K_2CO_3$, $Cs_2CO_3$, CsF, KF, $K_3PO_4$, KOAc or the like and a ligand such as Q-Phos, dppf, dppe or $PPh_3$ and the like affords compounds of formula F4 at temperatures ranging from rt to 160° C. using conventional or microwave heating.

The amine in compounds of formula F4 may be protected with a protecting group, as indicated by $P^1$, with previously described protecting groups. A preferred protecting group is t-butyl carbamate (Boc) or trifluoroacetamide. This protecting group ($P^1$) on the nitrogen may be removed as previously described or may be converted directly into compounds of the formula F6. It will be generally recognized that compounds of the formula F5 represent a subset of compounds of formula F6 where $R^1$ is equal to H. Compounds of formula F5 or F6 may be converted to their corresponding salts using methods generally accepted to those skilled in the art.

Compounds such as F6 were prepared from compounds of the formula F5 using methods such as reductive amination or alkylation using methods described previously. One skilled in the art will recognize that the addition of acid to decrease the pH of the reaction mixture to less than pH 7 may be required. One skilled in the art will also recognize that compounds of formula F6 may be obtained from F5 upon treatment with an alkyl chloride, bromide, iodide, mesylate or tosylate and the like in a solvent such as DMF, DMA, THF or EtOH in the presence of bases such as $NaHCO_3$, $Na_2CO_3$, $K_2CO_3$ or $Cs_2CO_3$ and the like.

Scheme G

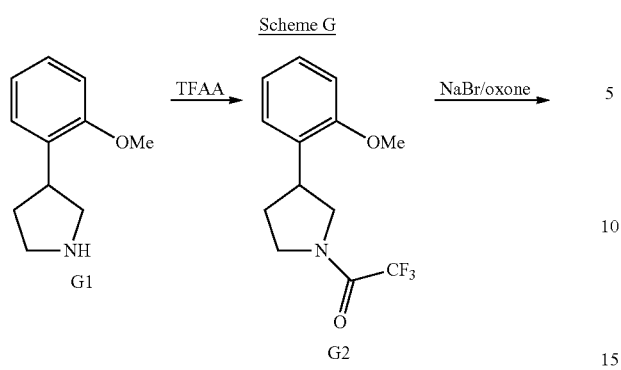

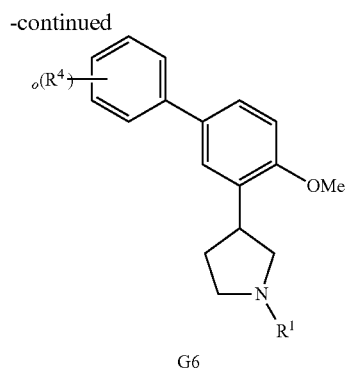

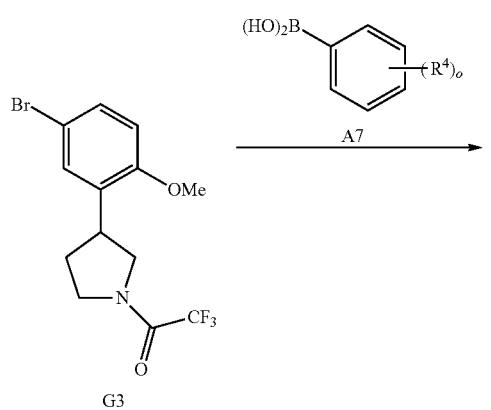

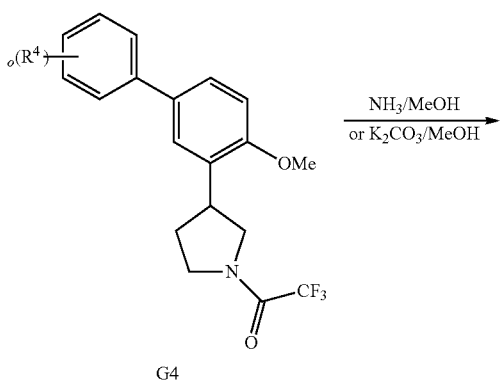

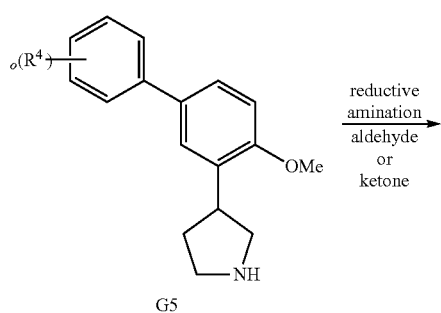

Intermediates of formula G6 were prepared according to Scheme G. Compounds of formula G4 were prepared from compounds of formula G1. Treatment of a compound of formula G1 with trifluoroacetic anhydride in the presence of a base such as pyridine, triethylamine or diisopropylethylamine or the like in a solvent such as $CH_2Cl_2$, THF, DMF, MeOH, EtOH or the like yields compounds of formula G2. Treatment of compounds of the formula G2 with an electrophilic bromine source such as $Br_2$, NBS, NaBr/oxone or the like in a solvent such as MeOH, $CH_2Cl_2$, EtOH, DMF, acetone, $H_2O$ and the like or mixtures there of produces compounds of formula G3.

One skilled in the art will recognize that compounds of formula G3 can be utilized for transition-metal catalyzed cross-coupling reactions as previously described. Treatment of compounds of formula G3 with organoboron compounds A7 in the presence of a catalyst such as $PdCl_2(dppf)$, $PdCl_2(dppe)$ $Pd_2(dba)_3$, $Pd(dba)_2$, $PdCl_2(PPh_3)_2$, $Pd(PPh_3)_4$ in a solvent such as $PhCH_3$, 1,4-dioxane, THF, DMA, DMF or DME in the presence of a base such as $Na_2CO_3$, $K_2CO_3$, $Cs_2CO_3$, CsF, KF, $K_3PO_4$, KOAc or the like and a ligand such as Q-Phos, dppf, dppe or $PPh_3$ and the like affords compounds of formula G4 at temperatures ranging from rt to 160° C. using conventional or microwave heating.

The amine in compounds of formula G4 may be protected with trifluoroacetamide (as depicted). It will be generally recognized that compounds of the formula G5 represent a subset of compounds of formula G6 where $R^1$ is equal to H. Compounds of formula G5 or G6 may be converted to their corresponding salts using methods generally accepted to those skilled in the art.

Compounds such as G6 were prepared from compounds of the formula G5 using methods such as reductive amination or alkylation. Thus treatment of G5 with a compound containing a carbonyl, such as an aldehyde or ketone, in the presence of a reductant such as $NaBH_4$, $NaBH_3CN$, $NaBH(OAc)_3$ or hydrogen gas in the presence of a catalyst in a solvent such as $CH_2Cl_2$, THF, DCE, MeOH, EtOH or similar affords compounds of formula G6. One skilled in the art will recognize that the addition of acid to decrease the pH of the reaction mixture to less than pH 7 may be required. One skilled in the art will also recognize that compounds of formula G6 may be obtained from G5 upon treatment with an alkyl chloride, bromide, iodide, mesylate or tosylate and the like in a solvent such as DMF, DMA, THF or EtOH in the presence of bases such as $NaHCO_3$, $Na_2CO_3$, $K_2CO_3$ or $Cs_2CO_3$ and the like.

Scheme H

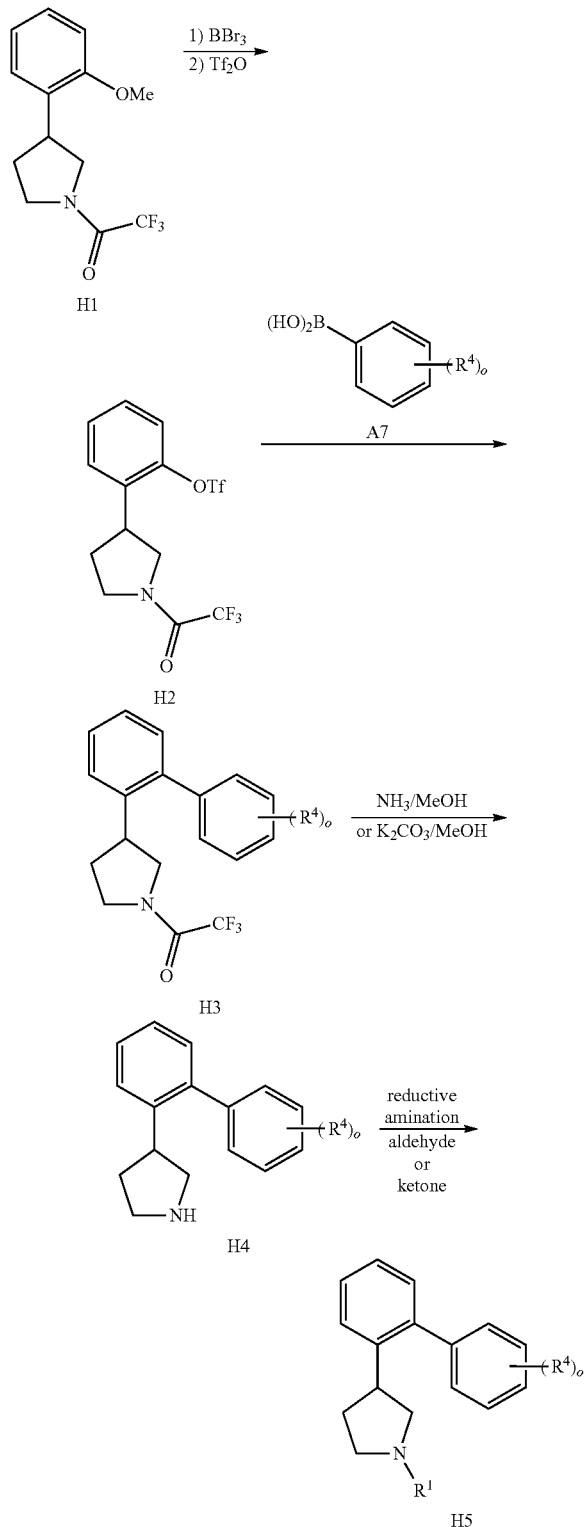

Intermediates of formula H5 were prepared according to Scheme H. Compounds of formula H3 were prepared from compounds of the formula H1. One skilled in the art will recognize treatment of compounds of the formula H1 with a demethylating agent such as LiI in collidine, HBr in AcOH, or preferably $BBr_3$ in $CH_2Cl_2$ would give compounds that can be converted into precursors for transition-metal catalyzed cross-coupling reactions. For example, treatment of compounds of the formula H1 with a triflating agent such as trifluoromethanesulfonic anhydride ($Tf_2O$) or N-phenyltrifluoromethanesulfonamide in DCE, $CH_2Cl_2$, THF or the like in the presence of a base such as pyridine, triethylamine or diisopropylethylamine provides compounds of the formula H2. Treatment of compounds of formula H2 with organoboron compounds A7 in the presence of a catalyst such as $PdCl_2(dppf)$, $PdCl_2(dppe)$ $Pd_2(dba)_3$, $Pd(dba)_2$, $PdCl_2(PPh_3)_2$, $Pd(PPh_3)_4$ in a solvent such as $PhCH_3$, 1,4-dioxane, THF, DMA, DMF or DME in the presence of a base such as $Na_2CO_3$, $K_2CO_3$, $Cs_2CO_3$, CsF, KF, $K_3PO_4$, KOAc or the like and a ligand such as Q-Phos, dppf, dppe or $PPh_3$ and the like affords compounds of formula H3 at temperatures ranging from rt to 160° C. using conventional or microwave heating.

The amine in compounds of formula H3 may be protected with trifluoroacetamide (as depicted). It will be generally recognized that compounds of the formula H4 represent a subset of compounds of formula H5 where $R_2$ is equal to H. Compounds of formula H4 or H5 may be converted to their corresponding salts using methods generally accepted to those skilled in the art.

Compounds such as H5 were prepared from compounds of the formula H4 using methods such as reductive amination or alkylation, as previously described. One skilled in the art will recognize that the addition of acid to decrease the pH of the reaction mixture to less than pH 7 may be required. One skilled in the art will also recognize that compounds of formula H5 may be obtained from H4 upon treatment with an alkyl chloride, bromide, iodide, mesylate or tosylate and the like in a solvent such as DMF, DMA, THF or EtOH in the presence of bases such as $NaHCO_3$, $Na_2CO_3$, $K_2CO_3$ or $Cs_2CO_3$ and the like.

EXAMPLES

Chemistry

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention.

Thin-layer chromatography (TLC) was performed using Merck silica gel 60 $F_{254}$ 2.5 cm×7.5 cm 250 μm or 5.0 cm×10.0 cm 250 μm pre-coated silica gel plates. Preparative thin-layer chromatography (PTLC) was performed using EM Science silica gel 60 $F_{254}$ 20 cm×20 cm 0.5 mm pre-coated plates with a 20 cm×4 cm concentrating zone.

Normal-phase flash column chromatography (FCC) was performed on silica gel ($SiO_2$) eluting with 2 M $NH_3$ in $MeOH/CH_2Cl_2$ or EtOAc in hexanes, unless otherwise noted.

Preparative reversed-phase HPLC(RP HPLC) was performed on a Hewlett Packard HPLC Series 1100, with a Phenomenex Luna C18 (5 μm, 4.6×150 mm) column. Detection was done at λ=230, 254 and 280 nm. The gradient was 10 to 99% acetonitrile/$H_2O$ (0.05% trifluoroacetic acid) over 5.0 min with a flow rate of 1 mL/min. Alternatively, HPLC was performed on a Dionex APS2000 LC/MS with a Phenomenex Gemini C18 (5 μm, 30×100 mm) column, and a gradient of 5 to 100% acetonitrile/$H_2O$ (20 mM $NH_4OH$) over 16.3 min, and a flow rate of 30 mL/min. Preparative RP HPLC was also performed on an Agilent 1100 preparative system with a Waters X-Bridge C18 (5 µm, 30×100 mm) column, and a gradient of 5 to 99% acetonitrile/H$_2$O (20 mM NH$_4$OH) over 17 min, and a flow rate of 80 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference or relative to residual protic solvent (multiplicity, coupling constant J in Hz, integration).

Chemical names were generated using ChemDraw Version 6.0.2 (CambridgeSoft, Cambridge, Mass.).

General Procedure 1 (Removal of Boc Groups):

Boc groups were removed using TFA/CH$_2$Cl$_2$ (1:1) or 4M HCl in dioxane/EtOAc (1:1). The compounds were then neutralized and extracted. Alternatively, compounds were characterized as the hydrochloride or trifluoroacetate salt where indicated.

General Procedure 2 (Removal of Trifluoroacetamide Groups):

Trifluoroacetamide groups were removed using K$_2$CO$_3$ (1 eq.) in MeOH (0.2 M) or 5M NH$_4$OH in MeOH. After 15 h, H$_2$O was added and the mixture extracted with EtOAc. The combined organics were dried. Silica gel chromatography (1-7% 2M NH$_3$/MeOH in CH$_2$Cl$_2$) then provided the deprotected amines.

General Procedure 3 (NH to NMe):

To amine in MeOH (0.1 M) was added excess 37 wt % [H$_2$CO]$_n$ in H$_2$O and NaBHOAc$_3$ (1.2 eq.). After 18 h, 5% Na$_2$CO$_3$ (aq.) was added and the mixture extracted with CH$_2$Cl$_2$. The combined organics were dried and purified to yield the corresponding methylated analogs.

Example 1

3-(4-Methoxy-2'-trifluoromethyl-biphenyl-3-yloxy)-azetidine

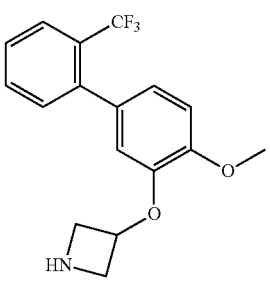

Step A: Preparation of (4-Bromo-2-fluoro-benzylidene)-tert-butyl-amine

To a CH$_2$Cl$_2$ (900 mL) solution of 4-bromo-2-fluoro-benzaldehyde (50.0 g, 246 mmol) was added tert-butylamine (42.3 mL, 29.3 g, 400 mmol) and MgSO$_4$ (60.0 g, 499 mmol). After 48 h the solution was filtered and concentrated to give 62.0 g (98% yield) of 4-Bromo-2-fluoro-benzylidene)-tert-butyl-amine as a yellow liquid. $^1$H NMR (400 MHz, CDCl$_3$): 8.48 (s, 1H), 7.89 (t, J=8.1 Hz, 1H), 7.32-7.25 (m, 2H), 1.29 (s, 9H).

Step B: Preparation of 3-(5-Bromo-2-formyl-phenoxy)-azetidine-1-carboxylic acid tert-butyl ester To a 0° C. DMF (720 mL) solution of the title compound of Step A (37.2 g, 144 mmol) and 3-hydroxy-azetidine-1-carboxylic acid tert-butyl ester (25.0 g, 144 mmol) was added NaH (60 wt % in mineral oil, 7.50 g, 188 mmol) portionwise over 2 h. The reaction was then allowed to warm to rt. After 18 h, H$_2$O was added and the reaction mixture extracted with EtOAc (2×). The combined organic layers were washed with brine and concentrated to give a yellow liquid that was treated with THF (360 mL), H$_2$O (360 mL) and AcOH (25 mL). After 5 h, this solution was made basic with 5% Na$_2$CO$_3$ (aq.) and extracted with EtOAc (2×). The combined organic layers were washed with brine and dried. The resulting solid was then triturated with 20% EtOAc in hexanes to give 41.9 g (81.5%) of the title compound as a white solid. $^1$H NMR (400 MHz, CDCl$_3$): 10.43 (s, 1H), 7.74 (d, J=8.3 Hz, 1H), 7.26-7.23 (m, 1H), 6.77 (d, J=1.6 Hz, 1H), 5.01-4.95 (m, 1H), 4.39 (ddd, J=9.9, 6.3, 0.8 Hz, 2H), 4.08 (dd, J=6.4, 0.8 Hz, 2H), 1.46 (s, 9H).

Step C: Preparation of 3-(5-Bromo-2-hydroxy-phenoxy)-azetidine-1-carboxylic acid tert-butyl ester To a CH$_2$Cl$_2$ (280 mL) solution of the title compound of Step B (24.7 g, 69.4 mmol) was added m-CPBA (77 wt %, 23.3 g, 104 mmol). After 15 h, 10% Na$_2$S$_2$O$_5$ was added and the solution allowed to stir until the aqueous was KI paper negative and extracted with CH$_2$Cl$_2$ (2×). The combined organic layers were washed with saturated NaHCO$_3$ (aq.), concentrated and treated with MeOH (220 mL) and 1N NaOH (220 mL). After 15 h, the reaction was partially concentrated to remove the MeOH and acidified with 1M KHSO$_4$ (220 mL) then extracted with CH$_2$Cl$_2$ (2×). The combined organic layers were washed with brine and dried to give a brown solid that was triturated with EtOAc/hexanes giving 17.6 g (74% yield) of the title compound as a white solid. $^1$H NMR (500 MHz, CDCl$_3$): 7.03 (dd, J=8.5, 2.1 Hz), 1H), 6.84 (d, J=8.5 Hz, 1H), 6.64 (d, J=2.2 Hz, 1H), 4.93-4.89 (m, 1H), 4.34 (dd, J=10.1, 6.8 Hz, 1H), 4.03 (dd, J=9.9, 3.7 Hz, 1H), 1.46 (s, 9H).

Step D: Preparation of 3-(5-Bromo-2-methoxy-phenoxy)-azetidine-1-carboxylic acid tert-butyl ester To the title compound of Step C (2.60 g, 7.54 mmol) and Cs$_2$CO$_3$ (2.70 g, 8.30 mmol) in DMF (75 mL) was added iodomethane (2.14 g, 0.94 mL, 15.09 mmol). After determined complete by TLC, saturated NaHCO$_3$ (aq.) was added and the mixture was extracted with CH$_2$Cl$_2$ (2×). The combined organic layers were dried. Silica gel chromatography (10-50% EtOAc in hexanes) gave 2.66 g (98%) of the title compound. MS (ESI): mass calcd. for C$_{15}$H$_{20}$BrNO$_4$, 357.06. m/z found, 304.1 [M−56]$^+$, 382.1 [M+Na]$^+$. $^1$H NMR (CDCl$_3$): 7.08 (dd, J=8.6, 2.3 Hz, 1H), 6.77 (d, J=8.6 Hz, 1H), 6.67 (d, J=2.2 Hz, 1H), 4.86 (tt, J=6.5, 4.3 Hz, 1H), 4.29 (ddd, J=9.7, 6.5, 0.8 Hz, 2H), 4.08 (dd, J=10.1, 4.2 Hz, 2H), 3.85 (s, 3H), 1.44 (s, 9H).

Step E: Preparation of 3-(4-Methoxy-2'-trifluoromethyl-biphenyl-3-yloxy)-azetidine-1-carboxylic acid tert-butyl ester To title compound of Step D (0.106 g, 0.296 mmol), 2-trifluoromethylphenylboronic acid (0.084 g, 0.444 mmol), K$_3$PO$_4$ (0.189 g, 0.888 mmol), Pd(dba)$_2$ (0.007 g, 0.012 mmol) and QPhos (0.004 g, 0.006 mmol) was added PhCH$_3$ (3 mL) and the reaction was heated to 80° C. for 18 h. The reaction was cooled to rt, diluted with EtOAc, filtered through a small silica plug and concentrated. Silica gel chromatography (0-30% EtOAc in hexanes) gave 0.062 g (49%) of the title compound. MS (ESI): mass calcd. for $C_{22}H_{24}F_3NO_4$, 423.17. m/z found, 368.1 [M-56]$^+$, 446.2 [M+Na]$^+$. $^1$H NMR (CDCl$_3$): 7.73 (d, J=7.8 Hz, 1H), 7.55 (t, J=7.3 Hz, 1H), 7.46 (t, J=7.6 Hz, 1H), 7.32 (d, J=7.6 Hz, 1H), 6.93 (s, 2H), 6.56 (s, 1H), 4.92-4.83 (m, 1H), 4.26 (dd, J=10.5, 6.5 Hz, 2H), 4.10 (dd, J=10.5, 4.3 Hz, 2H), 3.93 (s, 3H), 1.43 (s, 9H).

Step F: Preparation of 3-(4-Methoxy-2'-trifluoromethyl-biphenyl-3-yloxy)-azetidine To title compound of Step E (0.062 g, 0.146 mmol) in EtOAc (2 mL) was added 4M HCl in dioxane (2 mL). After 18 h, the reaction was neutralized with saturated NaHCO$_3$ (aq.) and extracted with CH$_2$Cl$_2$ (2×). The combined organics were dried and concentrated. Silica gel chromatography (10-80% 2M NH$_3$/MeOH in CH$_2$Cl$_2$) gave 0.029 g (61%) of the title compound. MS (ESI): mass calcd. for $C_{17}H_{16}F_3NO_2$, 323.11. m/z found, 324.2 [M+H]$^+$. $^1$H NMR (CDCl$_3$): 7.73 (d, J=7.8 Hz, 1H), 7.54 (t, J=7.3 Hz, 1H), 7.45 (t, J=7.6 Hz, 1H), 7.32 (d, J=7.6 Hz, 1H), 6.90 (td, J=8.2, 5.1 Hz, 2H), 6.59 (s, 1H), 5.02-4.97 (m, 1H), 3.92 (s, 3H), 3.96-3.85 (m, 7H).

Unless otherwise specified the compounds in Examples 2-17 were prepared similar to Example 1 using the appropriately substituted arylboronic acid.

Example 2

3-(4'-Fluoro-4-methoxy-2'-methyl-biphenyl-3-yloxy)-azetidine

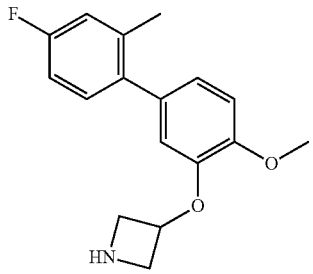 [SMILES: COc1ccc(-c2ccc(F)cc2C)cc1OC1CNC1]

MS (ESI): mass calcd. for $C_{17}H_{18}FNO_2$, 287.1. m/z found, 288.2 [M+H]$^+$. $^1$H NMR (CDCl$_3$): 7.14 (dd, J=8.4, 6.0 Hz, 1H), 6.99-6.88 (m, 3H), 6.84 (dd, J=8.2, 2.0 Hz, 1H), 6.52 (d, J=2.0 Hz, 1H), 5.03-4.98 (m, 1H), 3.95-3.86 (m, 7H), 2.24 (s, 3H).

Example 3

3'-(Azetidin-3-yloxy)-4'-methoxy-biphenyl-2-carbonitrile trifluoroacetate

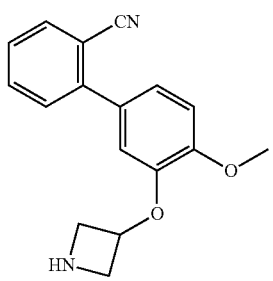 [SMILES: COc1ccc(-c2ccccc2C#N)cc1OC1CNC1]

MS (ESI): mass calcd. for $C_{17}H_{16}N_2O_2$, 280.1. m/z found, 281.2 [M+H]$^+$. $^1$H NMR (CDCl$_3$): 7.73 (dd, J=7.7, 0.8 Hz, 1H), 7.63 (dt, J=7.8, 1.1 Hz, 1H), 7.47 (d, J=7.8 Hz, 1H), 7.23 (dd, J=8.4, 2.0 Hz, 1H), 7.42 (dt, J=7.7, 0.8 Hz, 1H), 7.02 (d, J=8.4 Hz, 1H), 6.95 (d, J=1.9 Hz, 1H), 5.16 (s, 1H), 4.46 (s, 2H), 4.35 (s, 2H), 3.91 (s, 3H).

Example 4

3-(4-Methoxy-2',3'-dimethyl-biphenyl-3-yloxy)-azetidine

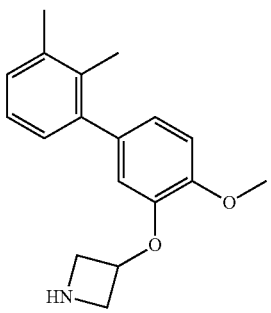 [SMILES: COc1ccc(-c2cccc(C)c2C)cc1OC1CNC1]

MS (ESI): mass calcd. for $C_{18}H_{21}NO_2$, 283.2. m/z found, 284.2 [M+H]$^+$. $^1$H NMR (CDCl$_3$): 7.17-7.10 (m, 2H), 7.06 (dd, J=7.0, 2.1 Hz, 1H), 6.93 (d, J=8.2 Hz, 1H), 6.87 (dd, J=8.2, 2.0 Hz, 1H), 6.56 (d, J=2.0 Hz, 1H), 5.02-4.96 (m, 1H), 3.92-3.88 (m, 7H), 2.34 (s, 3H), 2.16 (s, 3H).

Example 5

3-(3'-Fluoro-4-methoxy-2'-methyl-biphenyl-3-yloxy)-azetidine

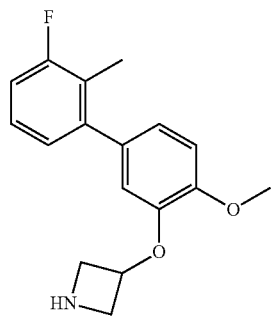 [SMILES: COc1ccc(-c2cccc(F)c2C)cc1OC1CNC1]

MS (ESI): mass calcd. for $C_{17}H_{18}FNO_2$, 287.1. m/z found, 288.2 [M+H]$^+$. $^1$H NMR (CDCl$_3$): 7.20-7.15 (m, 1H), 7.00 (t, J=8.1 Hz, 2H), 6.94 (d, J=8.2 Hz, 1H), 6.87 (dd, J=8.2, 2.0 Hz, 1H), 6.54 (d, J=2.0 Hz, 1H), 5.03-4.99 (m, 1H), 3.92-3.91 (m, 7H), 2.17 (d, J=2.5 Hz, 3H).

Example 6

3-(4-Methoxy-2',6'-dimethyl-biphenyl-3-yloxy)-azetidine trifluoroacetate

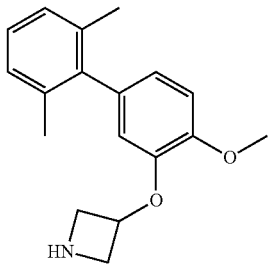 [SMILES: COc1ccc(-c2c(C)cccc2C)cc1OC1CNC1]

MS (ESI): mass calcd. for $C_{18}H_{21}NO_2$, 283.2. m/z found, 284.2 [M+H]$^+$. $^1$H NMR (CDCl$_3$): 7.15 (dd, J=8.3, 6.6 Hz, 1H), 7.09 (d, J=7.6 Hz, 2H), 6.97 (d, J=8.3 Hz, 1H), 6.81 (dd, J=8.2, 1.9 Hz, 1H), 6.51 (d, J=1.9 Hz, 1H), 5.08-5.03 (m, 1H), 4.35-4.30 (m, 4H), 3.88 (s, 3H), 2.01 (s, 6H).

Example 7

3-(4-Methoxy-2'-trifluoromethoxy-biphenyl-3-yloxy)-azetidine

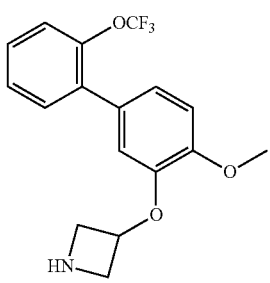 [SMILES: COc1ccc(-c2ccccc2OC(F)(F)F)cc1OC1CNC1]

MS (ESI): mass calcd. for $C_{17}H_{16}F_3NO_3$, 339.1. m/z found, 340.2 [M+H]$^+$. $^1$H NMR (CDCl$_3$): 7.42-7.29 (m, 4H), 7.14 (dd, J=8.4, 2.1 Hz, 1H), 6.97 (d, J=8.4 Hz, 1H), 6.85 (d, J=2.1 Hz, 1H), 5.14-5.09 (m, 1H), 4.39-4.29 (m, 4H), 3.89 (s, 3H).

Example 8

3-(4-Methoxy-2'-methyl-biphenyl-3-yloxy)-azetidine trifluoroacetate

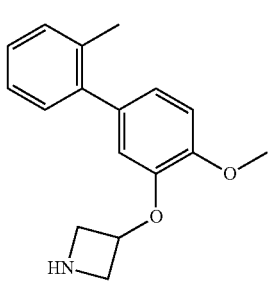 [SMILES: COc1ccc(-c2ccccc2C)cc1OC1CNC1]

MS (ESI): mass calcd. for $C_{17}H_{19}NO_2$, 269.1. m/z found, 270.2 [M+H]$^+$. $^1$H NMR (CDCl$_3$): 7.26-7.19 (m, 3H), 7.16 (d, J=6.6 Hz, 1H), 6.99 (dd, J=8.3, 2.0 Hz, 1H), 6.94 (d, J=8.3 Hz, 1H), 6.69 (d, J=2.0 Hz, 1H), 5.11-5.05 (m, 1H), 4.49-4.34 (m, 4H), 3.88 (s, 3H), 2.24 (s, 3H).

Example 9

3-(4,2'-Dimethoxy-biphenyl-3-yloxy)-azetidine

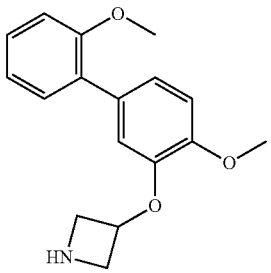 [SMILES: COc1ccc(-c2ccccc2OC)cc1OC1CNC1]

MS (ESI): mass calcd. for $C_{17}H_{19}NO_3$, 285.1. m/z found, 286.2 [M+H]$^+$. $^1$H NMR (CDCl$_3$): 7.34-7.27 (m, 2H), 7.10 (dd, J=8.3, 2.1 Hz, 1H), 7.01 (dt, J=7.5, 1.0 Hz, 1H), 6.97 (d, J=8.5 Hz, 1H), 6.94 (d, J=8.4 Hz, 1H), 6.88 (d, J=2.0 Hz, 1H), 5.06-5.00 (m, 1H), 3.93-3.90 (m, 7H), 3.81 (s, 3H).

Example 10

3-(2'-Chloro-4-methoxy-6'-trifluoromethyl-biphenyl-3-yloxy)-azetidine trifluoroacetate

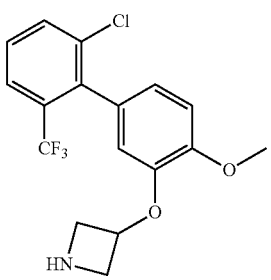 [SMILES: COc1ccc(-c2c(Cl)cccc2C(F)(F)F)cc1OC1CNC1]

MS (ESI): mass calcd. for $C_{17}H_{15}ClF_3NO_2$, 357.1. m/z found, 358.1 [M+H]$^+$. $^1$H NMR (CDCl$_3$): 7.72 (s, 1H), 7.55 (dd, J=8.0, 1.2 Hz, 1H), 7.41 (d, J=8.0 Hz, 1H), 7.11 (dd, J=8.4, 2.0 Hz, 1H), 6.99 (d, J=8.4 Hz, 1H), 6.85 (d, J=2.0 Hz, 1H), 5.10 (s, 1H), 4.39-4.33 (m, 4H), 3.90 (s, 3H).

Example 11

3-(4-Methoxy-4'-methyl-biphenyl-3-yloxy)-azetidine

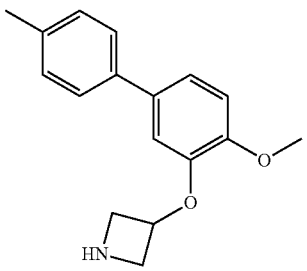

MS (ESI): mass calcd. for $C_{17}H_{19}NO_2$, 269.1. m/z found, 270.2 [M+H]$^+$. $^1$H NMR (CDCl$_3$): 7.38 (d, J=8.1 Hz, 2H), 7.23 (dd, J=11.6, 5.0 Hz, 3H), 6.95 (dd, J=5.2, 3.2 Hz, 2H), 5.14-5.09 (m, 1H), 4.39-4.30 (m, 4H), 3.87 (s, 3H), 2.38 (s, 3H).

Example 12

3-(4'-Fluoro-4-methoxy-3'-methyl-biphenyl-3-yloxy)-azetidine

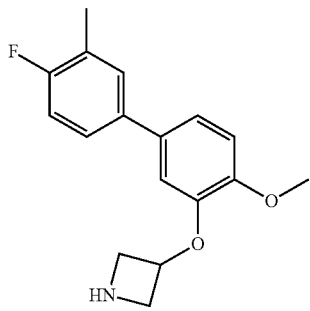 [SMILES: COc1ccc(-c2ccc(F)c(C)c2)cc1OC1CNC1]

MS (ESI): mass calcd. for $C_{17}H_{18}FNO_2$, 287.1. m/z found, 288.2 [M+H]$^+$. $^1$H NMR (CDCl$_3$): 7.33-7.22 (m, 2H), 7.09 (dd, J=8.3, 2.1 Hz, 1H), 7.07-7.01 (m, 1H), 6.94 (d, J=8.4 Hz, 1H), 6.77 (d, J=2.1 Hz, 1H), 5.11-5.06 (m, 1H), 3.94-3.90 (m, 7H), 2.33 (d, J=1.8 Hz, 3H).

Example 13

3-(4-Methoxy-3'-methyl-biphenyl-3-yloxy)-azetidine

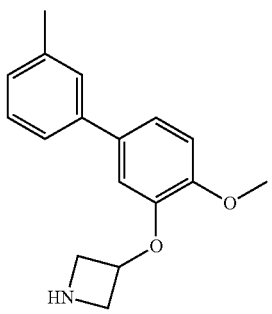 [SMILES: COc1ccc(-c2cccc(C)c2)cc1OC1CNC1]

MS (ESI): mass calcd. for $C_{17}H_{19}NO_2$, 269.1. m/z found, 270.2 [M+H]$^+$. $^1$H NMR (CDCl$_3$): 7.35-7.21 (m, 4H), 7.14 (d, J=6.6 Hz, 1H), 6.97 (s, 1H), 6.96 (d, J=6.6 Hz, 1H), 5.20-5.06 (m, 1H), 4.40-4.35 (m, 4H), 3.87 (s, 3H), 2.41 (s, 3H).

Example 14

3-(4-Methoxy-3',4'-dimethyl-biphenyl-3-yloxy)-azetidine

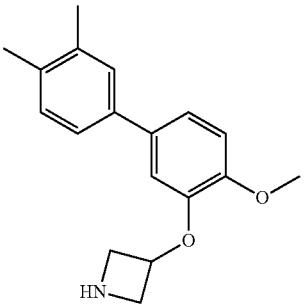

MS (ESI): mass calcd. for $C_{18}H_{21}NO_2$, 283.2. m/z found, 284.2 [M+H]$^+$. $^1$H NMR (CDCl$_3$): 7.28 (s, 1H), 7.24 (dd, J=8.0, 1.7 Hz, 1H), 7.18 (d, J=7.7 Hz, 1H), 7.14 (dd, J=8.3, 2.1 Hz, 1H), 6.94 (d, J=8.3 Hz, 1H), 6.82 (d, J=2.1 Hz, 1H), 5.13-5.04 (m, 1H), 3.99-3.87 (m, 7H), 2.32 (s, 3H), 2.29 (s, 3H).

Example 15

3-(4-Methoxy-biphenyl-3-yloxy)-azetidine

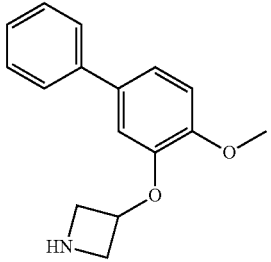 [SMILES: COc1ccc(-c2ccccc2)cc1OC1CNC1]

MS (ESI): mass calcd. for $C_{16}H_{17}NO_2$, 255.1. m/z found, 256.2 [M+H]$^+$. $^1$H NMR (CDCl$_3$): 7.53-7.47 (m, 2H), 7.44-7.37 (m, 2H), 7.34-7.27 (m, 1H), 7.16 (dd, J=8.3, 2.1 Hz, 1H), 6.95 (d, J=8.4 Hz, 1H), 6.85 (d, J=2.1 Hz, 1H), 5.11-5.05 (m, 1H), 3.96-3.90 (m, 7H).

Example 16

3-(4-Methoxy-2',5'-dimethyl-biphenyl-3-yloxy)-azetidine

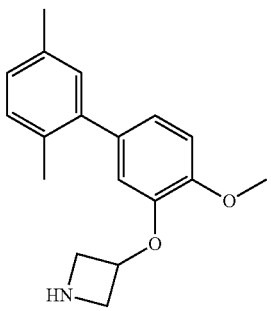 [SMILES: COc1ccc(-c2cc(C)ccc2C)cc1OC1CNC1]

MS (ESI): mass calcd. for $C_{18}H_{21}NO_2$, 283.2. m/z found, 284.1 [M+H]+. $^1$H NMR (CDCl$_3$): 7.14 (d, J=7.7 Hz, 1H), 7.06 (d, J=7.7 Hz, 1H), 7.03 (s, 1H), 6.93 (d, J=8.2 Hz, 1H), 6.88 (dd, J=8.2, 2.0 Hz, 1H), 6.57 (d, J=2.0 Hz, 1H), 5.03-4.98 (m, 1H), 3.91-3.90 (m, 7H), 2.34 (s, 3H), 2.22 (s, 3H).

Example 17

3-(2'-Chloro-4-methoxy-biphenyl-3-yloxy)-azetidine

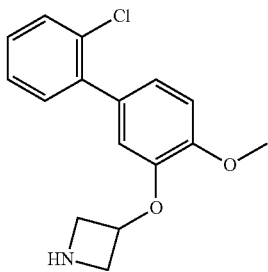 [SMILES: COc1ccc(-c2ccccc2Cl)cc1OC1CNC1]

MS (ESI): mass calcd. for $C_{16}H_{16}ClNO_2$, 289.1. m/z found, 290.2 [M+H]+. $^1$H NMR (CDCl$_3$): 7.46 (dd, J=7.6, 1.4 Hz, 1H), 7.35-7.22 (m, 3H), 7.01 (dd, J=8.3, 2.0 Hz, 1H), 6.95 (d, J=8.3 Hz, 1H), 6.74 (d, J=2.0 Hz, 1H), 5.06-5.01 (m, 1H), 3.95-3.90 (m, 7H).

Example 18

3-(2'-Chloro-4-methoxy-biphenyl-3-yloxy)-1-isopropyl-azetidine trifluoroacetate

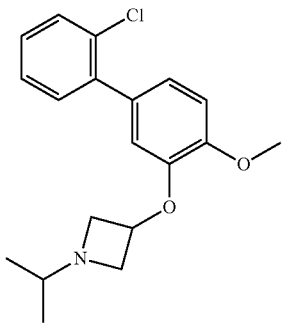 [SMILES: COc1ccc(-c2ccccc2Cl)cc1OC1CN(C(C)C)C1]

To the title compound of Example 17 (0.13 g, 0.44 mmol) in DCE was added acetone (0.5 mL) and NaBH(OAc)$_3$ (0.14 g, 0.66 mmol). After 18 h, saturated NaHCO$_3$ (aq.) was added and the mixture extracted with CH$_2$Cl$_2$ (2×). The combined organics were dried. Silica gel chromatography (10-80% 2M NH$_3$/MeOH in CH$_2$Cl$_2$) gave the title compound. MS (ESI): mass calcd. for $C_{19}H_{22}ClNO_2$, 331.13. m/z found, 332.2 [M+H]+. $^1$H NMR (CDCl$_3$): 7.45 (dd, J=8.1, 1.5 Hz, 1H), 7.33-7.24 (m, 3H), 7.12 (dd, J=8.4, 2.1 Hz, 1H), 6.98 (d, J=8.4 Hz, 1H), 6.82 (d, J=2.0 Hz, 1H), 5.09-4.97 (m, 1H), 4.77-4.73 (m, 2H), 3.95-3.81 (m, 6H), 2.35-2.23 (m, 4H), 2.05-1.91 (m, 1H), 1.89-1.81 (m, 1H).

Example 19

3-(2'-Chloro-4-methoxy-biphenyl-3-yloxy)-1-cyclobutyl-azetidine trifluoroacetate

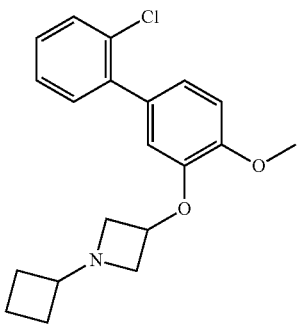 [SMILES: COc1ccc(-c2ccccc2Cl)cc1OC1CN(C2CCC2)C1]

Prepared according to Example 18 using cyclobutanone. MS (ESI): mass calcd. for $C_{20}H_{22}ClNO_2$, 343.13. m/z found, 345.2 [M+H]+. $^1$H NMR (CDCl$_3$): 7.45 (d, J=7.7 Hz, 1H), 7.34-7.24 (m, 3H), 7.12 (dd, J=8.4, 2.0 Hz, 1H), 6.98 (d, J=8.4 Hz, 1H), 6.84 (d, J=2.0 Hz, 1H), 5.09-5.04 (m, 1H), 4.84-4.68 (m, 2H), 3.95-3.86 (m, 5H), 3.34 (s, 1H), 1.34-1.33 (m, 6H).

Example 20

3-(2'-Trifluoromethyl-biphenyl-3-yloxy)-azetidine

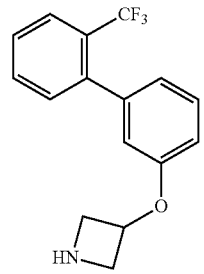 [SMILES: FC(F)(F)c1ccccc1-c1cccc(OC2CNC2)c1]

Step A: Preparation of 3-Methanesulfonyloxy-azetidine-1-carboxylic acid tert-butyl ester To 3-hydroxy-azetidine-1-carboxylic acid tert-butyl ester (1.21 g, 6.99 mmol) and Et$_3$N (0.85 g, 1.2 mL, 8.4 mmol) in CH$_2$Cl$_2$ (35 mL) at 0° C. was added methanesulfonyl chloride (0.88 g, 0.60 mL, 7.7 mmol). After 1 h, brine was added and the reaction extracted with CH$_2$Cl$_2$ (2×). The combined organics were dried to give 1.65 g (94%) of 3-methanesulfonyloxy-azetidine-1-carboxylic acid tert-butyl ester a yellow solid that was used without further purification. $^1$H NMR (CDCl$_3$): 5.20 (tt, J=6.7, 4.2 Hz, 1H), 4.28 (ddd, J=10.3, 6.7, 1.2 Hz, 2H), 4.10 (ddd, J=10.4, 4.2, 1.1 Hz, 2H), 3.07 (s, 3H), 1.44 (s, 9H).

Step B: Preparation of 3-(3-Bromo-phenoxy)-azetidine-1-carboxylic acid tert-butyl ester To 3-methanesulfonyloxy-azetidine-1-carboxylic acid tert-butyl ester (0.795 g, 3.16 mmol) and $Cs_2CO_3$ (1.13 g, 3.48 mmol) in DMF (30 mL) was added 3-bromophenol (0.547 g, 3.16 mmol). The reaction was heated to 80° C. for 18 h, then cooled to rt. Brine was added and the mixture extracted with $Et_2O$ (2×). The combined organics were washed with brine and dried. Silica gel chromatography (0-40% EtOAc in hexanes) gave 0.881 g (85%) of the title compound. MS (ESI): mass calcd. for $C_{14}H_{18}BrNO_3$, 327.05; m/z found, 272.0 [M-56]$^+$. $^1$H NMR (CDCl$_3$): 7.17-7.11 (m, 2H), 6.90-6.88 (m, 1H), 6.70-6.66 (m, 1H), 4.89-4.82 (m, 1H), 4.30 (ddd, J=9.7, 6.4, 0.9 Hz, 2H), 3.99 (dd, J=10.3, 4.1 Hz, 2H), 1.45 (s, 9H).

Step C: Preparation of 3-(2'-Trifluoromethyl-biphenyl-3-yloxy)-azetidine-1-carboxylic acid tert-butyl ester Prepared from the title compound of Step B as described in Example 1 Step E. MS (ESI): mass calcd. for $C_{21}H_{22}F_3NO_3$, 393.16. m/z found, 338.1 [M-56]$^+$. $^1$H NMR (CDCl$_3$): 7.74 (d, J=7.8 Hz, 1H), 7.55 (dd, J=7.5, 7.0 Hz, 1H), 7.46 (t, J=7.6 Hz, 1H), 7.34-7.26 (m, 1H), 6.95 (d, J=7.6 Hz, 1H), 6.78 (ddd, J=8.3, 2.5, 0.8 Hz, 1H), 6.70 (s, 1H), 4.91-4.84 (m, 1H), 4.28 (ddd, J=9.7, 6.4, 0.8 Hz, 2H), 4.02 (dd, J=10.3, 4.1 Hz, 2H), 1.45 (s, 9H).

Step D: Preparation of 3-(2'-Trifluoromethyl-biphenyl-3-yloxy)-azetidine

Prepared from the title compound of Step C as described in Example 1 Step F. MS (ESI): mass calcd. for $C_{16}H_{14}F_3NO$, 293.10. m/z found, 294.2 [M+H]$^+$. $^1$H NMR (CDCl$_3$): 7.74 (d, J=7.8 Hz, 1H), 7.55 (t, J=7.3 Hz, 1H), 7.46 (t, J=7.6 Hz, 1H), 7.32 (d, J=7.6 Hz, 1H), 7.29 (t, J=7.9 Hz, 1H), 6.92 (d, J=7.6 Hz, 1H), 6.79 (ddd, J=8.3, 2.5, 0.8 Hz, 1H), 6.71 (s, 1H), 5.04-4.99 (m, 1H), 3.92 (dd, J=9.4, 6.5 Hz, 2H), 3.82 (dd, J=9.5, 5.9 Hz, 2H).

Unless otherwise specified the compounds in Examples 21-23 were prepared similar to Example 20 using the appropriately substituted arylboronic acid.

Example 21

3-(2'-Chloro-biphenyl-3-yloxy)-azetidine

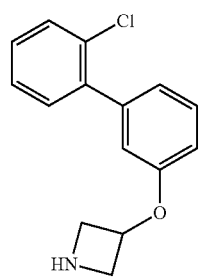 [SMILES: Clc1ccccc1-c1cccc(OC2CNC2)c1]

MS (ESI): mass calcd. for $C_{15}H_{14}ClNO$, 259.08. m/z found, 260.1 [M+H]$^+$. $^1$H NMR (CDCl$_3$): 7.52-7.42 (m, 1H), 7.34-7.26 (m, 4H), 7.03-7.01 (m, 1H), 6.86-6.82 (m, 1H), 6.80-6.77 (m, 1H), 5.05 (s, 1H), 3.95 (s, 4H).

Example 22

3-(3'-Methyl-biphenyl-3-yloxy)-azetidine

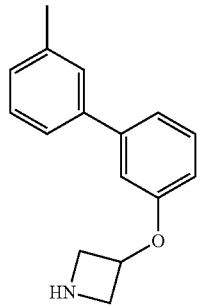 [SMILES: Cc1cccc(-c2cccc(OC3CNC3)c2)c1]

MS (ESI): mass calcd. for $C_{16}H_{17}NO$, 239.13. m/z found, 240.2 [M+H]$^+$. $^1$H NMR (CDCl$_3$): 7.36 (d, J=9.2 Hz, 1H), 7.32 (t, J=7.8 Hz, 2H), 7.18 (t, J=6.9 Hz, 2H), 6.99-6.97 (m, 1H), 6.73 (dd, J=8.1, 2.4 Hz, 1H), 5.08-5.03 (m, 1H), 3.98-3.91 (m, 2H), 3.98-3.91 (m, 2H), 2.41 (s, 3H).

Example 23

3-(2'-Methyl-biphenyl-3-yloxy)-azetidine

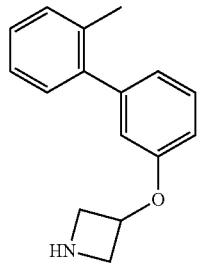 [SMILES: Cc1ccccc1-c1cccc(OC2CNC2)c1]

MS (ESI): mass calcd. for $C_{16}H_{17}NO$, 239.13. m/z found, 240.2 [M+H]$^+$. $^1$H NMR (CDCl$_3$): 7.30 (t, J=7.8 Hz, 1H), 7.27-7.18 (m, 4H), 6.93-6.90 (m, 1H), 6.77-6.67 (m, 2H), 5.04-4.99 (m, 1H), 3.95-3.91 (m, 2H), 3.84-3.81 (m, 2H), 2.27 (s, 3H).

Unless otherwise specified the compounds in Examples 24-27 were prepared similar to Example 20 Steps A-D using 3-(5-Bromo-2-chloro-phenoxy)-azetidine-1-carboxylic acid tert-butyl ester (prepared according to Example 20 Step B using 5-Bromo-2-chloro-phenol) and the appropriate boronic acid.

Example 24

3-(4,2'-Dichloro-biphenyl-3-yloxy)-azetidine trifluoroacetate

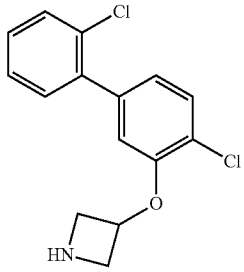 [SMILES: Clc1ccc(-c2ccccc2Cl)cc1OC1CNC1]

MS (ESI): mass calcd. for $C_{15}H_{13}Cl_2NO$, 293.04. m/z found, 294.1 [M+H]$^+$. $^1$H NMR (CDCl$_3$): 7.48-4.73 (m, 2H), 7.33-7.26 (m, 3H), 7.05 (dd, J=8.2, 1.8 Hz, 1H), 6.71 (d, J=1.8 Hz, 1H), 5.25-5.11 (m, 1H), 4.46-4.42 (m, 2H), 4.32-4.29 (m, 2H).

Example 25

3-(4-Chloro-2'-trifluoromethyl-biphenyl-3-yloxy)-azetidine trifluoroacetate

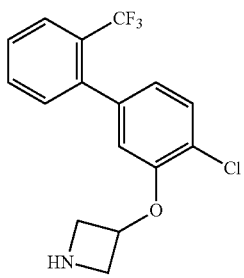

MS (ESI): mass calcd. for $C_{16}H_{13}ClF_3NO$, 327.06. m/z found, 328.1 [M+H]$^+$. $^1$H NMR (CDCl$_3$): 7.74 (d, J=7.7 Hz, 1H), 7.57 (t, J=7.5 Hz, 1H), 7.49 (t, J=7.6 Hz, 1H), 7.42 (d, J=8.1 Hz, 1H), 7.28 (d, J=7.5 Hz, 1H), 6.95 (dd, J=8.1, 1.7 Hz, 1H), 6.58 (d, J=0.9 Hz, 1H), 5.17-5.11 (m, 1H), 4.44-4.39 (m, 2H), 4.30-4.26 (m, 2H).

Example 26

3-(4-Chloro-2'-methyl-biphenyl-3-yloxy)-azetidine trifluoroacetate

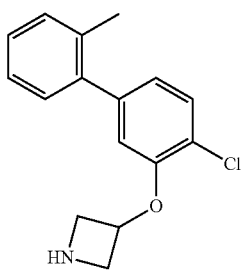 [SMILES: Cc1ccccc1-c1ccc(Cl)c(OC2CNC2)c1]

MS (ESI): mass calcd. for $C_{16}H_{16}ClNO$, 273.09. m/z found, 274.1 [M+H]$^+$. $^1$H NMR (CDCl$_3$): 7.40 (d, J=8.1 Hz, 1H), 7.30-7.19 (m, 3H), 7.13 (d, J=7.3 Hz, 1H), 6.95 (dd, J=8.1, 1.8 Hz, 1H), 6.56 (d, J=1.8 Hz, 1H), 5.23-5.03 (m, 1H), 4.45-4.41 (m, 2H), 4.32-4.31 (m, 2H), 2.22 (s, 3H).

Example 27

3-(4-Chloro-3'-methyl-biphenyl-3-yloxy)-azetidine trifluoroacetate

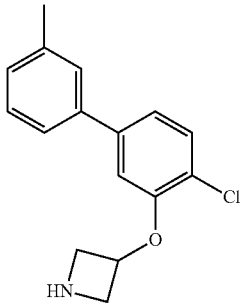 [SMILES: Cc1cccc(-c2ccc(Cl)c(OC3CNC3)c2)c1]

MS (ESI): mass calcd. for $C_{16}H_{16}ClNO$, 273.09. m/z found, 274.2 [M+H]$^+$. $^1$H NMR (CDCl$_3$): 7.39 (d, J=8.2 Hz, 1H), 7.34-7.25 (m, 3H), 7.17 (dd, J=8.2, 1.9 Hz, 2H), 6.81 (d, J=1.9 Hz, 1H), 5.24-5.18 (m, 1H), 4.44-4.39 (m, 2H), 4.30-4.26 (m, 2H), 2.40 (s, 3H).

Example 28

3-(Azetidin-3-yloxy)-2'-trifluoromethyl-biphenyl-4-carbonitrile

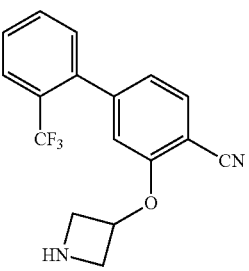 [SMILES: N#Cc1ccc(-c2ccccc2C(F)(F)F)cc1OC1CNC1]

Step A: Preparation of 3-(5-Bromo-2-cyano-phenoxy)-azetidine-1-carboxylic acid tert-butyl ester To a solution of 4-bromo-2-fluoro-benzonitrile (1.0 g, 5.0 mmol) and 3-hydroxy-azetidine-1-carboxylic acid tert-butyl ester (0.95 g, 5.5 mmol) in DMF (15 mL) at 0° C., was added NaH (60% in mineral oil, 130 mg, 5.5 mmol). After 18 h, H$_2$O and EtOAc were added and the organic portion washed with brine (3×) and dried to provide the title compound (1.4 g, 79%). MS (ESI): mass calcd. for $C_{15}H_{17}BrN_2O_3$, 352.0. m/z found, 377.1 [M+Na]$^+$. $^1$H NMR (CDCl$_3$): 7.48 (d, J=8.2 Hz, 1H), 7.25 (dd, J=8.2, 1.7 Hz, 1H), 6.79 (d, J=1.6 Hz, 1H), 5.00-4.92 (m, 1H), 4.38 (ddd, J=9.9, 6.4, 1.1 Hz, 2H), 4.11 (dd, J=10.0, 3.8 Hz, 2H), 1.48 (s, 9H).

Step B: Preparation of 3-(4-Cyano-2'-trifluoromethyl-biphenyl-3-yloxy)-azetidine-1-carboxylic acid tert-butyl ester Prepared from the title compound of Step A according to Example 1 Step E using 2-trifluoromethylphenylboronic acid.

Step C: Preparation of 3-(Azetidin-3-yloxy)-2'-trifluoromethyl-biphenyl-4-carbonitrile Prepared from the title compound of Step B according to general procedure 1. MS (ESI): mass calcd. for $C_{17}H_{13}F_3N_2O$, 318.1. m/z found, 319.2 [M+H]$^+$. $^1$H NMR (CDCl$_3$): 7.78 (d, J=7.7 Hz, 1H), 7.64-7.57 (m, 2H), 7.55 (dd, J=7.7, 7.6 Hz, 1H), 6.99 (dd, J=7.9, 1.2 Hz, 1H), 6.64 (s, 1H), 5.12-5.03 (m, 1H), 4.01-3.86 (m, 4H), 2.69-2.54 (m, 1H).

Example 29

3-(Azetidin-3-yloxy)-biphenyl-4-carbonitrile

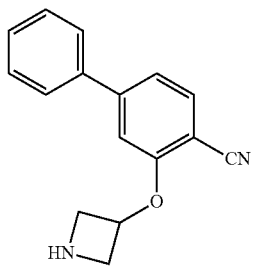 [SMILES: N#Cc1ccc(-c2ccccc2)cc1OC1CNC1]

Prepared according to Example 28 using phenylboronic acid. MS (ESI): mass calcd. for $C_{16}H_{14}N_2O$, 250.1. m/z found, 251.2 [M+H]$^+$. $^1$H NMR (CDCl$_3$): 7.65 (d, J=8.0 Hz, 1H), 7.56-7.52 (m, 2H), 7.52-7.47 (m, 2H), 7.46-7.42 (m, 1H), 7.25 (d, J=8.0 Hz, 1H), 6.85 (s, 1H), 5.21-5.13 (m, 1H), 4.03-3.91 (m, 4H), 1.97-1.90 (br m, 1H).

Example 30

3-(Azetidin-3-yloxy)-2'-methyl-biphenyl-4-carbonitrile

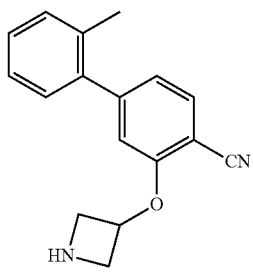 [SMILES: Cc1ccccc1-c1ccc(C#N)c(OC2CNC2)c1]

Prepared according to Example 28 using 2-methylphenylboronic acid. MS (ESI): mass calcd. for $C_{17}H_{16}N_2O$, 264.1. m/z found, 265.3 [M+H]$^+$. $^1$H NMR (CDCl$_3$): 7.62 (d, J=7.9 Hz, 1H), 7.38-7.24 (m, 3H), 7.18 (d, J=7.4 Hz, 1H), 7.00 (d, J=9.1 Hz, 1H), 6.62 (s, 1H), 5.20-5.01 (m, 1H), 4.04-3.83 (m, 4H), 2.26 (s, 3H).

Example 31

5-(Azetidin-3-yloxy)-2-methyl-biphenyl-4-carbonitrile

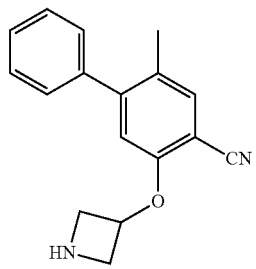 [SMILES: Cc1cc(C#N)c(OC2CNC2)cc1-c1ccccc1]

Step A: Preparation of 3-(5-Bromo-2-cyano-4-methyl-phenoxy)-azetidine-1-carboxylic acid tert-butyl ester Prepared according to Example 28 using 4-bromo-2-fluoro-5-methyl-benzonitrile (1.0 g, 4.7 mmol), 3-hydroxy-azetidine-1-carboxylic acid tert-butyl ester (1.1 g, 6.5 mmol), DMF (20 mL) and NaH (60% in mineral oil, 156 mg, 6.5 mmol) to provide the title compound (1.3 g, 74%). MS (ESI): mass calcd. for $C_{16}H_{19}BrN_2O_3$, 366.1. m/z found, 389.1 [M+Na]$^+$. $^1$H NMR (CDCl$_3$): 7.45 (s, 1H), 6.83 (s, 1H), 4.97-4.88 (m, 1H), 4.35 (ddd, J=9.8, 6.4, 0.9 Hz, 1H), 4.09 (dd, J=10.0, 3.9 Hz, 1H), 2.36 (s, 3H), 1.47 (s, 9H).

Step B: Preparation of 3-(4-Cyano-6-methyl-biphenyl-3-yloxy)-azetidine-1-carboxylic acid tert-butyl ester Prepared from the title compound of Step A as described in Example 1 Step E using phenylboronic acid.

Step C: Preparation of 5-(Azetidin-3-yloxy)-2-methyl-biphenyl-4-carbonitrile

Prepared from the title compound of Step B according to general procedure 1. $^1$H NMR (CDCl$_3$): 7.48-7.36 (m, 4H), 7.31-7.22 (m, 2H), 6.53 (s, 1H), 5.11-4.99 (m, 1H), 4.02-3.83 (m, 4H), 2.19 (s, 3H).

Example 32

3-(4-Ethoxy-2'-methyl-biphenyl-3-yloxy)-azetidine hydrochloride

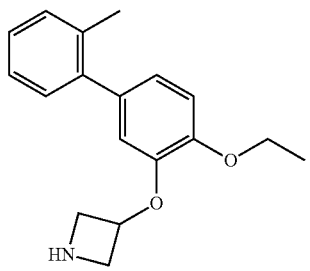 [SMILES: CCOc1ccc(-c2ccccc2C)cc1OC1CNC1]

Step A: Preparation of 3-(4-Formyl-2'-methyl-biphenyl-3-yloxy)-azetidine-1-carboxylic acid tert-butyl ester To 3-(5-Bromo-2-formyl-phenoxy)-azetidine-1-carboxylic acid tert-butyl ester (1.4 g, 3.9 mmol), 2-methylphenylboronic acid (0.55 g, 4.1 mmol), $K_3PO_4$ (2.5 g, 11.7 mmol), Pd(dba)$_2$ (0.046 g, 0.080 mmol) and QPhos (0.114 g, 0.160 mmol) was added $PhCH_3$ (16 mL). After 18 h at rt the reaction was diluted with EtOAc and filtered through a small silica pad. Silica gel chromatography (10-40% EtOAc in hexanes) gave 1.42 g (98% yield) of the title compound. $^1$H NMR (CDCl$_3$): 7.26-7.18 (m, 4H), 6.94 (d, J=8.3 Hz, 1H), 6.90 (dd, J=8.2, 2.0 Hz, 1H), 6.55 (d, J=1.9 Hz, 1H), 4.90-4.86 (m, 1H), 4.26 (dd, J=10.1, 6.3 Hz, 2H), 4.12 (m, 4H), 2.26 (s, 3H), 1.49 (t, J=7.0 Hz, 3H), 1.44 (s, 9H).

Step B: Preparation of 3-(4-Hydroxy-2'-methyl-biphenyl-3-yloxy)-azetidine-1-carboxylic acid tert-butyl ester To a $CH_2Cl_2$ (6 mL) solution of the title compound of Step A (1.40 g, 3.81 mmol) was added m-CPBA (77 wt %, 1.30 g, 5.70 mmol). After 15 h, 10 wt % $Na_2S_2O_5$ (aq.) was added and the solution allowed to stir until the aqueous was KI paper negative and extracted with $CH_2Cl_2$ (2×). The combined organic layers were washed with saturated $NaHCO_3$ (aq.), concentrated and treated with MeOH (30 mL) and 1N NaOH (15 mL). After 15 h, the reaction was partially concentrated to remove the MeOH and acidified with 1M $KHSO_4$ then extracted with EtOAc (2×). The combined organic layers were dried and concentrated to give the 1.1 g of the title compound that was used in the next step without further purification.

Step C: Preparation of 3-(4-Ethoxy-2'-methyl-biphenyl-3-yloxy)-azetidine hydrochloride Prepared according to Example 1 Steps D and F using iodoethane. MS (ESI): mass calcd. for $C_{18}H_{21}NO_2$, 283.16. m/z found, 284.3 [M+H]$^+$. $^1$H NMR (DMSO-D$_6$): 9.26 (s, 2H), 7.28-7.17 (m, 4H), 7.08 (d, J=8.3 Hz, 1H), 6.93 (dd, J=8.3, 2.1 Hz, 1H), 6.74 (d, J=2.1 Hz, 1H), 5.06-5.01 (m, 1H), 4.40 (dd, J=12.4, 6.7 Hz, 2H), 4.10 (q, J=7.0 Hz, 2H), 4.05-4.01 (m, 2H), 2.23 (s, 3H), 1.37 (t, J=7.0 Hz, 3H).

Unless otherwise specified the compounds in Examples 33-36 were prepared similar to Example 32 using the appropriate alkyl halide.

Example 33

3-[2'-Methyl-4-(2,2,2-trifluoro-ethoxy)-biphenyl-3-yloxy]-azetidine

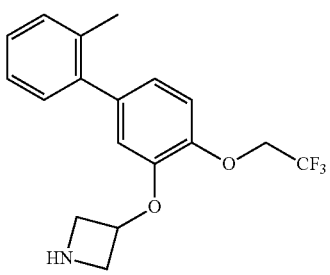 [SMILES: Cc1ccccc1-c1ccc(OCC(F)(F)F)c(OC2CNC2)c1]

MS (ESI): mass calcd. for $C_{18}H_{18}F_3NO_2$, 337.13. m/z found, 338.3 [M+H]$^+$. $^1$H NMR (500 MHz, CDCl$_3$): 7.27-7.18 (m, 4H), 7.04 (d, J=8.2 Hz, 1H), 6.87 (dd, J=8.2, 2.0 Hz, 1H), 6.60 (d, J=2.0 Hz, 1H), 5.03-4.98 (m, 1H), 4.40 (d, J=8.4 Hz, 2H), 3.93-3.85 (m, 4H), 2.25 (s, 3H).

Example 34

3-(4-Cyclobutoxy-2'-methyl-biphenyl-3-yloxy)-azetidine

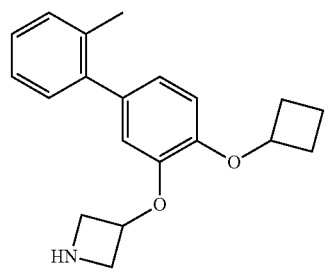 [SMILES: Cc1ccccc1-c1ccc(OC2CCC2)c(OC2CNC2)c1]

MS (ESI): mass calcd. for $C_{20}H_{23}NO_2$, 309.17. m/z found, 311.3 [M+H]$^+$. $^1$H NMR (500 MHz, DMSO-D$_6$): 9.26 (s, 2H), 7.28-7.17 (m, 4H), 6.93-6.89 (m, 2H), 6.73 (d, J=1.6 Hz, 1H), 5.06-5.01 (m, 1H), 4.74-4.69 (m, 1H), 4.38 (dd, J=11.7, 6.7 Hz, 2H), 4.02 (dd, J=11.7, 4.7 Hz, 2H), 2.49-2.43 (m, 2H), 2.23 (s, 3H), 2.14-2.06 (m, 2H), 1.84-1.77 (m, 1H), 1.70-1.61 (m, 1H).

Example 35

3-(4-Cyclopropylmethoxy-2'-methyl-biphenyl-3-yloxy)-azetidine

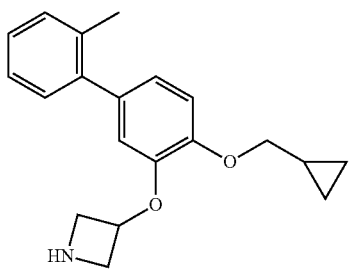 [SMILES: Cc1ccccc1-c1ccc(OCC2CC2)c(OC2CNC2)c1]

MS (ESI): mass calcd. for $C_{20}H_{23}NO_2$, 309.17. m/z found, 311.3 [M+H]$^+$. $^1$H NMR (500 MHz, CDCl$_3$): 7.25-7.19 (m, 4H), 6.93 (d, J=8.2 Hz, 1H), 6.85 (dd, J=8.2, 2.1 Hz, 1H), 6.60 (d, J=2.0 Hz, 1H), 5.03-4.98 (m, 1H), 3.91-3.88 (m, 6H), 2.27 (s, 3H), 1.39-1.31 (m, 1H), 0.67-0.64 (m, 2H), 0.39-0.36 (m, 2H).

Example 36

3-(4-Isopropoxy-2'-methyl-biphenyl-3-yloxy)-azetidine

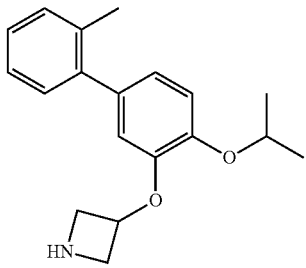 [SMILES: Cc1ccccc1-c1ccc(OC(C)C)c(OC2CNC2)c1]

MS (ESI): mass calcd. for $C_{19}H_{23}NO_2$, 297.17. m/z found, 298.3 [M+H]$^+$. $^1$H NMR (500 MHz, DMSO-D$_6$): 9.18 (s, 2H), 7.28-7.18 (m, 4H), 7.09 (d, J=8.5 Hz, 1H), 6.93 (dd, J=8.3, 2.1 Hz, 1H), 6.75 (d, J=2.1 Hz, 1H), 5.04-4.99 (m, 1H), 4.65-4.60 (m, 1H), 4.38 (dd, J=12.4, 6.7 Hz, 2H), 4.02 (dd, J=12.4, 5.0 Hz, 1H), 2.24 (s, 3H), 1.31 (d, J=6.0 Hz, 6H).

Example 37

3-(Azetidin-3-yloxy)-2'-trifluoromethyl-biphenyl-4-carboxylic acid diethylamide

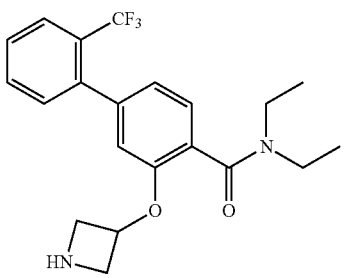 [SMILES: CCN(CC)C(=O)c1ccc(-c2ccccc2C(F)(F)F)cc1OC1CNC1]

Step A: Preparation of 3-(4-Formyl-2'-trifluoromethyl-biphenyl-3-yloxy)-azetidine-1-carboxylic acid tert-butyl ester To the title compound of Example 1 Step B (0.20 g, 0.56 mmol), 2-trifluoromethylphenylboronic acid (0.16 g, 0.84 mmol), K$_3$PO$_4$ (0.357 g, 1.68 mmol) Pd(dba)$_2$ (0.013 g, 0.022 mmol) and Q-Phos (0.008 g, 0.011 mmol) was added PhCH$_3$. After 48 h at rt the reaction was diluted with EtOAc and filtered through a small silica pad. Silica gel chromatography (0-30% EtOAc in hexanes) gave 0.24 g (99% yield) of the title compound. MS (ESI): mass calcd. for $C_{22}H_{22}F_3NO_4$, 421.15. m/z found, 336.1 [M-56]$^+$, 444.1 [M+Na]$^+$. $^1$H NMR (CDCl$_3$): 10.53 (d, J=0.7 Hz, 1H), 7.91 (d, J=7.9 Hz, 1H), 7.78 (d, J=7.8 Hz, 1H), 7.61 (t, J=7.3 Hz, 1H), 7.54 (t, J=7.6 Hz, 1H), 7.33 (d, J=7.5 Hz, 1H), 7.05 (d, J=7.9 Hz, 1H), 6.59 (s, 1H), 4.99 (tt, J=6.4, 4.0 Hz, 1H), 4.37-4.29 (m, 2H), 4.11-4.08 (m, 2H), 1.45 (s, 9H).

Step B: Preparation of 3-(4-Carboxy-2'-trifluoromethyl-biphenyl-3-yloxy)-azetidine-1-carboxylic acid tert-butyl ester To a CH$_2$Cl$_2$ (6 mL) solution of the title compound of Step A (0.236 g, 0.560 mmol) was added m-CPBA (77 wt %, 0.189 g, 0.840 mmol). After 15 h, 10% Na$_2$S$_2$O$_5$ was added and the solution allowed to stir until the aqueous was KI paper negative and extracted with CH$_2$Cl$_2$ (2×). The combined organic layers were dried and treated with MeOH (10 mL) and 1N NaOH (10 mL). After 15 h, the reaction was partially concentrated to remove the MeOH and acidified with 1M HCl (220 mL) then extracted with EtOAc (2×). The combined organic layers were dried and concentrated. Silica gel chromatography (0-30% EtOAc in hexanes) gave 0.091 g (37% yield) of the title compound. (MS (ESI): mass calcd. for $C_{22}H_{22}F_3NO_5$, 437.15. m/z found, 382.1 [M-56]$^+$, 460.1 [M+Na]$^+$. $^1$H NMR (CDCl$_3$): 7.73 (d, J=7.8 Hz, 1H), 7.55 (t, J=7.5 Hz, 1H), 7.45 (t, J=7.7 Hz, 1H), 7.32 (d, J=7.6 Hz, 1H), 6.99 (d, J=8.2 Hz, 1H), 6.87 (dd, J=8.2, 1.9 Hz, 1H), 6.52 (d, J=1.0 Hz, 1H), 4.97-4.88 (m, 1H), 4.30 (dd, J=9.8, 6.4 Hz, 2H), 4.05 (dd, J=9.9, 3.7 Hz, 2H), 1.45 (s, 9H)) and 0.091 g (39% yield) of 3-(4-Hydroxy-2'-trifluoromethyl-biphenyl-3-yloxy)-azetidine-1-carboxylic acid tert-butyl ester (MS (ESI): mass calcd. for $C_{21}H_{22}F_3NO_4$, 409.15. m/z found, 354.1 [M-56]$^+$, 432.1 [M+Na]$^+$. $^1$H NMR (CDCl$_3$): 8.19 (d, J=8.0 Hz, 1H), 7.78 (d, J=8.2 Hz, 1H), 7.61 (t, J=7.2 Hz, 1H), 7.54 (t, J=7.5 Hz, 1H), 7.32 (d, J=7.5 Hz, 1H), 7.12 (dd, J=8.0, 1.3 Hz, 1H), 6.63 (s, 1H), 5.11-5.00 (m, 1H), 4.36 (dd, J=10.1, 6.4 Hz, 2H), 4.12 (dd, J=10.6, 3.6 Hz, 2H), 1.45 (s, 9H).

Step C: Preparation of 3-(4-Diethylcarbamoyl-2'-trifluoromethyl-biphenyl-3-yloxy)-azetidine-1-carboxylic acid tert-butyl ester To the title compound of Step B (0.09 g, 0.21 mmol) in CH$_2$Cl$_2$ (2 mL) was added HOBt (0.003 g, 0.02 mmol), Et$_3$N (0.03 mL, 0.02 g, 0.23 mmol), Et$_2$NH (0.02 mL, 0.02 mL, 0.23 mmol) and EDC.HCl (0.04 g, 0.23 mmol). After 18 h, saturated NaHCO$_3$ (aq.) was added and the reaction extracted with CH$_2$Cl$_2$ (2×). The combined organics were dried. Silica gel chromatography (0-60% EtOAc in hexanes) gave 0.082 g (80% yield) of the title compound. MS (ESI): mass calcd. for $C_{26}H_{31}F_3N_2O_4$, 492.22. m/z found, 437.2 [M-56]$^+$, 493.2 [M+H]$^+$. $^1$H NMR (CDCl$_3$): 7.75 (d, J=7.7 Hz, 1H), 7.58 (t, J=7.4 Hz, 1H), 7.50 (t, J=7.7 Hz, 1H), 7.32 (d, J=7.5 Hz, 1H), 7.28 (d, J=7.6 Hz, 1H), 6.99 (dd, J=7.6, 1.2 Hz, 1H), 6.51 (s, 1H), 4.93-4.83 (m, 1H), 4.25 (dd, J=9.6, 6.5 Hz, 2H), 4.01 (s, 1H), 3.94 (s, 1H), 3.79 (s, 1H), 3.41 (s, 1H), 3.21 (q, J=7.1 Hz, 2H), 1.44 (s, 9H), 1.28 (t, J=7.1 Hz, 3H), 1.10 (t, J=7.1 Hz, 3H).

Step D: Preparation of 3-(Azetidin-3-yloxy)-2'-trifluoromethyl-biphenyl-4-carboxylic acid diethylamide Prepared from the title compound of Step C according to general procedure 1. MS (ESI): mass calcd. for $C_{21}H_{23}F_3N_2O_2$, 392.17. m/z found, 393.2 [M+H]$^+$. $^1$H NMR (CDCl$_3$): 7.74 (d, J=7.3 Hz, 1H), 7.57 (t, J=7.2 Hz, 1H), 7.48 (t, J=7.5 Hz, 1H), 7.33 (t, J=8.9 Hz, 1H), 7.25 (d, J=7.7 Hz, 1H), 6.95 (dd, J=7.7, 1.3 Hz, 1H), 6.56 (s, 1H), 5.03-4.97 (m, 1H), 3.90-3.78 (m, 2H), 3.22 (q, J=7.1 Hz, 2H), 1.96 (s, 2H), 1.27 (t, J=7.1 Hz, 3H), 1.10 (t, J=7.1 Hz, 3H).

Example 38

3-(4-Chloro-3'-methyl-biphenyl-2-yloxy)-azetidine

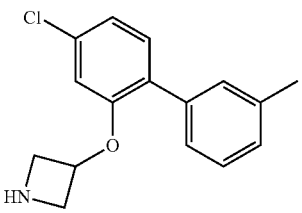 [SMILES: Cc1cccc(-c2ccc(Cl)cc2OC2CNC2)c1]

Step A: Preparation of 3-(5-Chloro-2-trifluoromethanesulfonyloxy-phenoxy)-azetidine-1-carboxylic acid tert-butyl ester To 3-(5-chloro-2-hydroxy-phenoxy)-azetidine-1-carboxylic acid tert-butyl ester (2.0 g, 6.7 mmol) in CH$_2$Cl$_2$ (34 mL) at 0° C. was added Et$_3$N (0.74 g, 1.0 mL, 7.3 mmol) and Tf$_2$O (2.0 g, 7.0 mmol). After warming to rt, H$_2$O was added and the mixture extracted with CH$_2$Cl$_2$ (2×). The combined organics were dried. Silica gel chromatography (5-25%) gave 1.12 g (39%) of the title compound as a white solid. $^1$H NMR (CDCl$_3$): 7.20 (d, J=8.7 Hz, 1H), 7.03 (dd, J=8.7, 2.3 Hz, 1H), 6.67 (d, J=2.3 Hz, 1H), 4.95-4.91 (m, 1H), 4.34 (ddd, J=10.0, 6.4, 1.0 Hz, 2H), 4.08-4.04 (m, 2H), 1.46 (s, 9H).

Step B: Preparation of 3-(4-Chloro-3'-methyl-biphenyl-2-yloxy)-azetidine-1-carboxylic acid tert-butyl ester To the title compound of Step A (0.12 g, 0.27 mmol), 3-methylphenylboronic acid (0.08 g, 0.60 mmol), K$_3$PO$_4$ (0.128 g, 0.54 mmol), Pd(dppf)Cl$_2$.CH$_2$Cl$_2$ (0.013 g, 0.017 mmol) and dppf (0.006 g, 0.010 mmol) was added dioxane (3 mL). The flask was heated at 100° C. for 18 h, cooled to rt, diluted with EtOAc and filtered through a small silica pad. Silica gel chromatography (10-40% EtOAc in hexanes) gave 0.073 g (72% yield) of the title compound. $^1$H NMR (CDCl$_3$): 7.31-7.26 (m, 4H), 7.18-7.15 (m, 1H), 7.05 (dd, J=8.2, 2.0 Hz, 1H), 6.57 (d, J=1.9 Hz, 1H), 4.86-4.81 (m, 1H), 4.30-4.26 (m, 2H), 3.96 (dd, J=10.2, 4.2 Hz, 2H), 2.40 (s, 3H), 1.44 (s, 9H).

Step C: Preparation of 3-(4-Chloro-3'-methyl-biphenyl-2-yloxy)-azetidine

Prepared according to Example 1 Step F. MS (ESI): mass calcd. for C$_{16}$H$_{16}$ClNO, 273.09. m/z found, 274.1 [M+H]$^+$. $^1$H NMR (CDCl$_3$): 7.34-7.24 (m, 4H), 7.16-7.14 (m, 1H), 7.01 (dd, J=8.2, 2.0 Hz, 1H), 6.62 (d, J=2.0 Hz, 1H), 4.99-4.92 (m, 1H), 3.92-3.88 (m, 2H), 3.76-3.74 (m, 2H), 2.40 (s, 3H).

Unless otherwise specified the compounds in Examples 39-42 were prepared similar to Example 38 using the appropriate arylboronic acid.

Example 39

3-(4-Chloro-2'-methyl-biphenyl-2-yloxy)-azetidine

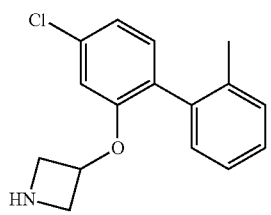 [SMILES: Cc1ccccc1-c1ccc(Cl)cc1OC1CNC1]

Prepared according to Example 38 using 2-methylphenylboronic acid. MS (ESI): mass calcd. for C$_{16}$H$_{16}$ClNO, 273.1. m/z found, 274.0 [M+H]$^+$. $^1$H NMR (CDCl$_3$): 7.29-7.20 (m, 3H), 7.14-7.07 (m, 2H), 7.01 (dd, J=8.1, 1.9 Hz, 1H), 6.62 (d, J=1.9 Hz, 1H), 4.95-4.89 (m, 1H), 3.84-3.66 (m, 4H), 2.16 (s, 3H).

Example 40

3-(4-Chloro-3'-trifluoromethyl-biphenyl-2-yloxy)-azetidine

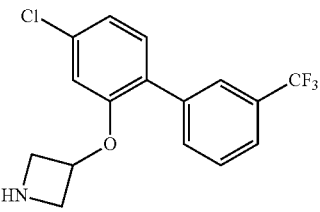 [SMILES: FC(F)(F)c1cccc(-c2ccc(Cl)cc2OC2CNC2)c1]

MS (ESI): mass calcd. for C$_{16}$H$_{13}$ClF$_3$NO, 327.06. m/z found, 328.0 [M+H]$^+$. $^1$H NMR (CDCl$_3$): 7.80 (s, 1H), 7.70-7.68 (m, 1H), 7.60-7.58 (m, 1H), 7.54-7.50 (m, 1H), 7.28 (d, J=8.2 Hz, 1H), 7.05 (dd, J=8.2, 2.0 Hz, 1H), 6.65 (d, J=2.0 Hz, 1H), 5.02-4.96 (m, 1H), 3.95-3.90 (m, 2H), 3.76-3.73 (m, 2H).

Example 41

3-(4-Chloro-4'-fluoro-3'-methyl-biphenyl-2-yloxy)-azetidine

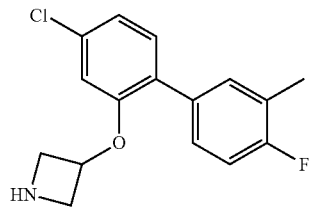 [SMILES: Cc1cc(-c2ccc(Cl)cc2OC2CNC2)ccc1F]

MS (ESI): mass calcd. for C$_{16}$H$_{15}$ClFNO, 291.1. m/z found, 292.2 [M+H]$^+$. $^1$H NMR (CDCl$_3$): 7.35-7.29 (m, 2H), 7.24 (d, J=8.2 Hz, 1H), 7.09-7.00 (m, 2H), 6.63 (d, J=2.0 Hz, 1H), 5.07-4.90 (m, 1H), 4.03-3.86 (m, 2H), 3.84-3.67 (m, 2H), 2.33 (s, 3H).

Example 42

3-(4-Chloro-3',4'-dimethyl-biphenyl-2-yloxy)-azetidine

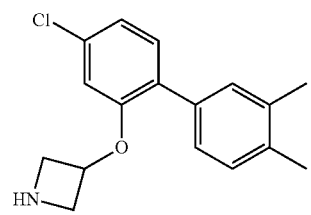 [SMILES: Cc1ccc(-c2ccc(Cl)cc2OC2CNC2)cc1C]

MS (ESI): mass calcd. for C$_{17}$H$_{18}$ClNO, 287.1. m/z found, 288.2 [M+H]$^+$. $^1$H NMR (CDCl$_3$): 7.38-7.34 (m, 1H), 7.32-

7.25 (m, 2H), 7.22-7.17 (m, 1H), 7.03 (dd, J=8.2, 2.0 Hz, 1H), 6.63 (d, J=2.0 Hz, 1H), 4.10-3.62 (m, 1H), 4.08-3.62 (m, 4H), 2.33 (s, 3H), 2.32 (s, 3H).

Example 43

(±)-3-(4-Methoxy-2'-methyl-biphenyl-3-yl)-pyrrolidine

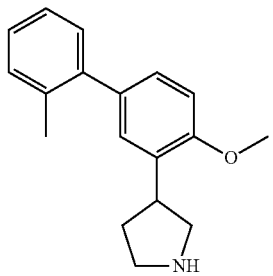 [SMILES: COc1ccc(-c2ccccc2C)cc1C1CCNC1]

Step A: Preparation of 2,2,2-Trifluoro-1-[3-(2-methoxy-phenyl)-pyrrolidin-1-yl]-ethanone To 3-(2-Methoxy-phenyl)-pyrrolidine hydrochloride (5.4 g, 25.3 mmol) in $CH_2Cl_2$ (125 mL) at 0° C. was added $Et_3N$ (7.4 mL, 53.1 mmol) and TFAA (5.8 g, 3.9 mL, 27.8 mmol). After 15 h, $H_2O$ was added and the mixture extracted with $CH_2Cl_2$ (2×). The combined organics were dried. Silica gel chromatography (5-30% EtOAc in hexanes) gave 7.56 of the title compound.

Step B: Preparation of 1-[3-(5-Bromo-2-methoxyphenyl)-pyrrolidin-1-yl]-2,2,2-trifluoro-ethanone To the title compound of Step A (2.75 g, 10.1 mmol) and NaBr (4.2 g, 41 mmol) in acetone (50 mL)/$H_2O$ (50 mL) at 0° C. was added Oxone (6.2 g, 10.1 mmol) portionwise over 1 h. After 3 h, the ice bath was removed and the reaction allowed to warm to rt. Then 5 wt % $Na_2S_2O_5$ (aq.) was added and the mixture extracted with EtOAc (2×). The combined organics were washed with brine and dried to give 3.95 g (>98%) of the title compound. $^1H$ NMR ($CDCl_3$): 7.35 (dd, J=8.7, 3.8, 2.5 Hz, 1H), 7.25 (dd, J=5.5, 2.7 Hz, 1H), 6.77 (dd, J=8.7, 4.5 Hz, 1H), 4.13-4.06 (m, 1H), 3.94-3.82 (m, 4H), 3.75-3.57 (m, 2H), 3.51-3.41 (m, 1H), 2.37-2.05 (m, 2H).

Step C: Preparation of 2,2,2-Trifluoro-1-[3-(4-methoxy-2'-methyl-biphenyl-3-yl)-pyrrolidin-1-yl]-ethanone Prepared according to Example 38 Step B using 2-methylphenylboronic acid.

Step D: Preparation of (±)-3-(4-Methoxy-2'-methyl-biphenyl-3-yl)-pyrrolidine

Prepared according to general procedure 2 from the title compound of Step C. MS (ESI): mass calcd. for $C_{18}H_{21}NO$, 267.2. m/z found, 268.3 $[M+H]^+$. $^1H$ NMR ($CDCl_3$): 7.33-7.12 (m, 6H), 6.96-6.85 (m, 1H), 5.26-4.84 (br m, 1H), 3.79-3.56 (m, 1H), 3.57-3.38 (m, 1H), 3.38-3.18 (m, 1H), 3.05-2.88 (m, 1H), 2.30 (s, 3H), 2.25-2.11 (m, 1H), 2.07-1.85 (m, 1H).

Unless otherwise specified the compounds in Examples 44-49 were prepared similar to Example 43 using the appropriate arylboronic acid.

Example 44

(±)-3-(3'-Fluoro-4-methoxy-2'-methyl-biphenyl-3-yl)-pyrrolidine

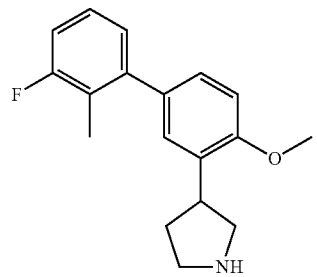 [SMILES: COc1ccc(-c2cccc(F)c2C)cc1C1CCNC1]

MS (ESI): mass calcd. for $C_{18}H_{20}FNO$, 285.2. m/z found, 286.3 $[M+H]^+$. $^1H$ NMR ($CDCl_3$): 7.45-7.38 (m, 0.5H), 7.35-7.26 (m, 1.5H), 7.21-7.08 (m, 2.5H), 7.04-6.95 (m, 1.5H), 6.93-6.86 (m, 1H), 3.87 (s, 3H), 3.65-3.48 (m, 1H), 3.39-3.26 (m, 1H), 3.22-3.10 (m, 1H), 3.10-2.97 (m, 1H), 2.93-2.80 (m, 1H), 2.23-2.09 (m, 3H), 1.96-1.77 (m, 1H).

Example 45

(±)-3-(2',3'-Difluoro-4-methoxy-biphenyl-3-yl)-pyrrolidine

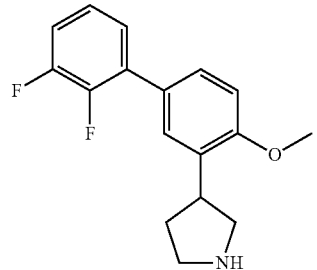 [SMILES: COc1ccc(-c2cccc(F)c2F)cc1C1CCNC1]

MS (ESI): mass calcd. for $C_{17}H_{17}F_2NO$, 289.1. m/z found, 290.3 $[M+H]^+$. $^1H$ NMR ($CDCl_3$): 7.43-7.33 (m, 2H), 7.19-7.02 (m, 3H), 6.93 (d, J=9.1 Hz, 1H), 3.87 (s, 3H), 3.65-3.51 (m, 1H), 3.42-3.30 (m, 1H), 3.27-3.13 (m, 2H), 3.13-3.00 (m, 1H), 2.98-2.87 (m, 1H), 2.27-2.12 (m, 1H), 2.02-1.84 (m, 1H).

Example 46

(±)-3-(4-Methoxy-3'-trifluoromethyl-biphenyl-3-yl)-pyrrolidine

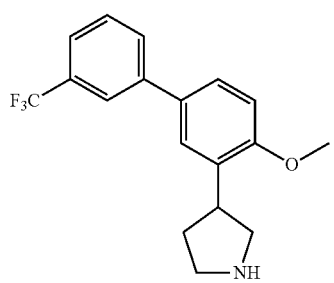 [SMILES: COc1ccc(-c2cccc(C(F)(F)F)c2)cc1C1CCNC1]

MS (ESI): mass calcd. for $C_{18}H_{18}F_3NO$, 321.1. m/z found, 322.3 [M+H]$^+$. $^1$H NMR (CDCl$_3$): 7.74 (d, J=7.9 Hz, 1H), 7.55 (dd, J=7.5, 7.0 Hz, 1H), 7.45 (dd, J=7.7, 7.5 Hz, 1H), 7.35 (d, J=7.6 Hz, 1H), 7.27-7.22 (m, 1H), 7.20-7.14 (m, 2H), 6.95-6.87 (m, 1H), 3.89 (s, 3H), 3.65-3.51 (m, 1H), 3.40-3.26 (m, 1H), 3.22-3.10 (m, 1H), 3.09-2.99 (m, 1H), 2.93-2.80 (m, 1H), 2.25-2.11 (m, 1H), 1.98-1.78 (m, 1H).

Example 47

(±)-3-(4-Methoxy-2'-trifluoromethyl-biphenyl-3-yl)-pyrrolidine

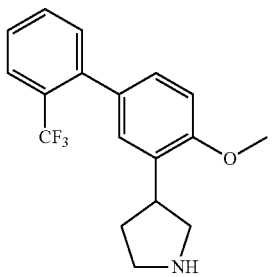 [SMILES: COc1ccc(-c2ccccc2C(F)(F)F)cc1C1CCNC1]

MS (ESI): mass calcd. for $C_{18}H_{18}F_3NO$, 321.1. m/z found, 322.3 [M+H]$^+$. $^1$H NMR (CDCl$_3$): 7.74 (d, J=7.9 Hz, 1H), 7.56 (dd, J=8.0, 7.5 Hz, 1H), 7.45 (dd, J=7.7, 7.5 Hz, 1H), 7.35 (d, J=7.6 Hz, 1H), 7.29-7.22 (m, 1H), 7.19-7.13 (m, 2h), 6.94-6.87 (m, 1H), 3.89 (5, 3H), 3.63-3.53 (m, 1H), 3.37-3.27 (m, 1H), 3.21-3.10 (m, 1H), 3.09-2.98 (m, 1H), 2.92-2.82 (m, 1H), 2.24-2.11 (m, 1H), 1.94-1.80 (m, 1H).

Example 48

(±)-3-(4-Methoxy-2'-trifluoromethoxy-biphenyl-3-yl)-pyrrolidine

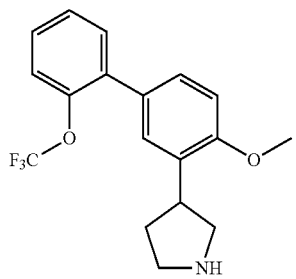 [SMILES: COc1ccc(-c2ccccc2OC(F)(F)F)cc1C1CCNC1]

MS (ESI): mass calcd. for $C_{18}H_{18}F_3NO_2$, 337.1. m/z found, 338.3 [M+H]$^+$. $^1$H NMR (CDCl$_3$): 7.45-7.35 (m, 1.5H), 7.34-7.25 (m, 3.5H), 7.18-7.05 (m, 1H), 6.97-6.89 (m, 1H), 3.87 (s, 3H), 3.65-3.51 (m, 1H), 3.38-3.25 (m, 1H), 3.23-3.11 (m, 1H), 3.09-2.97 (m, 1H), 2.93-2.81 (m, 1H), 2.26-2.09 (m, 1H), 1.98-1.77 (m, 1H).

Example 49

(±)-3-(4-Methoxy-biphenyl-3-yl)-pyrrolidine

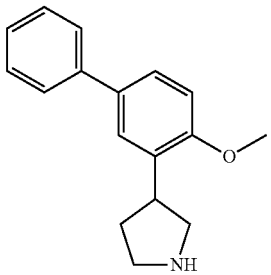 [SMILES: COc1ccc(-c2ccccc2)cc1C1CCNC1]

MS (ESI): mass calcd. for $C_{17}H_{19}NO$, 253.2. m/z found, 254.2 [M+H]$^+$. $^1$H NMR (CDCl$_3$): 7.62-7.52 (m, 2H), 7.48-7.39 (m, 4H), 7.36-7.27 (m, 1H), 6.95 (d, J=8.7 Hz, 1H), 3.89 (s, 3H), 3.68-3.51 (m, 1H), 3.49-3.31 (m, 1H), 3.30-3.17 (m, 1H), 3.16-3.06 (m, 1H), 3.05-2.91 (m, 1H), 2.71-2.39 (br m, 1H), 2.31-2.10 (m, 1H), 2.05-1.83 (m, 1H).

Example 50

(±)-3-(4-Methoxy-biphenyl-3-yl)-1-methyl-pyrrolidine

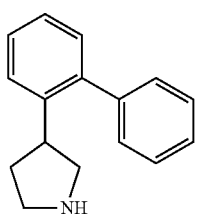 [SMILES: c1ccc(-c2ccccc2C2CCNC2)cc1]

Prepared from the title compound of Example 49 using general procedure 3. MS (ESI): mass calcd. for $C_{18}H_{21}NO$, 267.2. m/z found, 268.3 [M+H]$^+$. $^1$H NMR (CDCl$_3$): 7.59-7.50 (m, 3H), 7.45-7.36 (m, 3H), 7.33-7.26 (m, 1H), 6.91 (d, J=8.4 Hz, 1H), 3.86 (s, 3H), 3.84-3.73 (m, 1H), 3.01 (dd, J=8.6, 8.5 Hz, 1H), 2.87-2.76 (m, 1H), 2.69-2.59 (m, 1H), 2.54 (dd, J=8.8, 8.4 Hz, 1H), 2.41 (s, 3H), 2.38-2.25 (m, 1H), 2.00-1.87 (m, 1H).

Example 51

(±)-3-Biphenyl-2-yl-pyrrolidine

Step A: Preparation of 2,2,2-Trifluoro-1-[3-(2-hydroxy-phenyl)-pyrrolidin-1-yl]-ethanone To the title compound of Example 43 Step A (1.2 g, 4.4 mmol) in CH$_2$Cl$_2$ (15 mL) at 0° C. was added BBr$_3$ (1M in CH$_2$Cl$_2$, 9.8 mL, 9.8 mmol). After warming to rt and allowing to stir for 18 h, sat'd NaHCO$_3$ (aq.) was added slowly. The reaction was then extracted with CH$_2$Cl$_2$. The combined organic layers were dried and used in the next step without further purification. MS (ESI): mass calcd. for C$_{12}$H$_{12}$F$_3$NO$_2$, 259.2. m/z found, 260.1 [M+H]$^+$. $^1$H NMR (CDCl$_3$): 7.22-7.11 (m, 2H), 6.97-6.88 (m, 1H), 6.87-6.77 (m, 1H), 4.26-4.14 (m, 1H), 4.04-3.94 (m, 0.5H), 3.93-3.84 (m, 0.5H), 3.82-3.71 (m, 1H), 3.70-3.53 (m, 2H), 2.44-2.26 (m, 1.5H), 2.25-2.13 (m, 0.5H).

Step B: Preparation of Trifluoro-methanesulfonic acid 2-[1-(2,2,2-trifluoro-acetyl)-pyrrolidin-3-yl]-phenyl ester Prepared according to Example 38 Step A using the title compound from Step A. MS (ESI): mass calcd. for C$_{13}$H$_{11}$F$_6$NO$_4$S, 391.2. m/z found, 392.1 [M+H]$^+$. $^1$H NMR (CDCl$_3$): 7.50-7.37 (m, 3H), 7.36-7.30 (m, 1H), 4.18 (dd, J=10.6, 7.9 Hz, 0.5H), 4.10 (dd, J=12.5, 7.8 Hz, 0.5H), 3.97 (dd, J=10.9, 10.8 Hz, 0.5H), 3.94-3.87 (m, 0.5H), 3.86-3.66 (m, 2H), 3.65-3.56 (m, 1H), 2.55-2.46 (m, 0.5H), 2.45-2.37 (m, 0.5H), 2.23-2.13 (m, 0.5H), 2.12-2.02 (m, 0.5H).

Step C: Preparation of (±)-1-(3-Biphenyl-2-yl-pyrrolidin-1-yl)-2,2,2-trifluoro-ethanone To a nitrogen flushed flask containing the title compound of Step C (75 mg, 0.19 mmol), phenylboronic acid (35 mg, 0.29 mmol), Pd(dppf)Cl$_2$.CH$_2$Cl$_2$ (7 mg, 5 mol %), dppf (5 mg, 5 mol %) and K$_3$PO$_4$ (60 mg, 0.3 mmol) was added dioxane (5 mL). The reaction was heated at reflux for 18 h. After cooling to rt, the crude reaction mixture was filtered through a 1"×½" silica gel plug and the plug was rinsed with DCM. The filtrate was concentrated and purified by RP HPLC to provide the title compound (34 mg, 56%). MS (ESI): mass calcd. for C$_{18}$H$_{16}$F$_3$NO, 319.1. m/z found, 320.3 [M+H]$^+$. $^1$H NMR (CDCl$_3$): 7.52-7.37 (m, 4H), 7.37-7.22 (m, 5H), 3.98-3.81 (m, 2H), 3.62-3.41 (m, 3H), 2.28-1.98 (m, 2H).

Step E: Preparation of (±)-3-Biphenyl-2-yl-pyrrolidine

Prepared according to general procedure 2 from the title compound of Step C. $^1$H NMR (CDCl$_3$): 7.47-7.39 (m, 3H), 7.39-7.36 (m, 2H), 7.33-7.29 (m, 2H), 7.27-7.20 (m, 2H), 3.38-3.10 (m, 3H), 3.08-2.77 (m, 2H), 2.75-2.36 (m, 1H), 2.21-1.99 (m, 1H), 1.95-1.75 (m, 1H).

Unless otherwise specified the compounds in Examples 52-67 were prepared similar to Example 51 using the appropriate arylboronic acid.

Example 52

(±)-3-(3'-Methyl-biphenyl-2-yl)-pyrrolidine

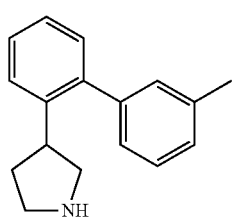 [SMILES: Cc1cccc(-c2ccccc2C2CCNC2)c1]

MS (ESI): mass calcd. for C$_{17}$H$_{19}$N, 237.2. m/z found, 238.3 [M+H]$^+$. $^1$H NMR (CDCl$_3$): 7.44-7.38 (m, 1H), 7.37-7.33 (m, 1H), 7.33-7.27 (m, 1H), 7.26-7.16 (m, 3H), 7.14-7.06 (m, 2H), 3.44-3.10 (m, 2H), 3.09-2.73 (m, 2H), 2.42 (s, 3H), 2.33-1.99 (m, 3H), 1.94-1.73 (m, 1H).

Example 53

(±)-1-Methyl-3-(3'-methyl-biphenyl-2-yl)-pyrrolidine

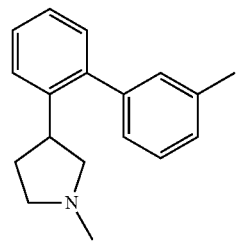 [SMILES: Cc1cccc(-c2ccccc2C2CCN(C)C2)c1]

Prepared according to general procedure 3 using Example 52. MS (ESI): mass calcd. for C$_{18}$H$_{21}$N, 251.2. m/z found, 252.3 [M+H]$^+$. $^1$H NMR (CDCl$_3$): 7.56 (d, J=7.9 Hz, 1H), 7.37 (dt, J=1.6, 7.6 Hz, 1H), 7.32-7.27 (m, 1H), 7.25-7.14 (m, 3H), 7.12-7.05 (m, 2H), 3.55-3.43 (m, 1H), 2.81 (dd, J=9.0, 8.6 Hz, 1H), 2.77-2.63 (m, 2H), 2.58 (dd, J=7.4, 7.3 Hz, 1H), 2.41 (s, 3H), 2.39 (s, 3H), 2.42-2.14 (m, 1H), 1.95-1.84 (m, 1H).

Example 54

(±)-3-(4'-Methyl-biphenyl-2-yl)-pyrrolidine

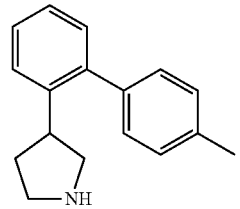 [SMILES: Cc1ccc(-c2ccccc2C2CCNC2)cc1]

MS (ESI): mass calcd. for C$_{17}$H$_{19}$N, 237.2. m/z found, 238.3 [M+H]$^+$. $^1$H NMR (CDCl$_3$): 7.44-7.39 (m, 1H), 7.38-7.32 (m, 1H), 7.27-7.15 (m, 6H), 3.41-3.13 (m, 2H), 3.09-2.82 (m, 2H), 2.81-2.55 (m, 2H), 2.42 (s, 3H), 2.21-2.02 (m, 1H), 1.97-1.82 (m, 1H).

Example 55

(±)-1-Methyl-3-(4'-methyl-biphenyl-2-yl)-pyrrolidine

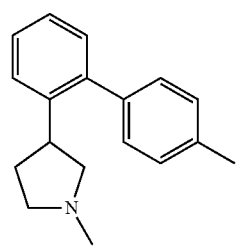 [SMILES: Cc1ccc(-c2ccccc2C2CCN(C)C2)cc1]

Prepared according to general procedure 3 using the title compound of Example 54. MS (ESI): mass calcd. for $C_{18}H_{21}N$, 251.2. m/z found, 252.3 [M+H]$^+$. $^1$H NMR (CDCl$_3$): 7.56 (d, J=8.7 Hz, 1H), 7.37 (dt, J=1.7, 7.2 Hz, 1H), 7.25-7.16 (m, 6H), 3.55-3.44 (m, 1H), 2.80 (dd, J=9.0, 8.5 Hz, 1H), 2.75-2.68 (m, 1H), 2.68-2.61 (m, 1H), 2.61-2.55 (m, 1H), 2.42 (s, 3H), 2.38 (s, 3H), 2.25-2.13 (m, 1H), 1.95-1.85 (m, 1H).

Example 56

3-(4'-Chloro-biphenyl-2-yl)-pyrrolidine

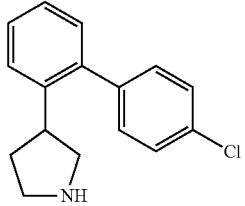 [SMILES: Clc1ccc(-c2ccccc2C2CCNC2)cc1]

MS (ESI): mass calcd. for $C_{16}H_{16}ClN$, 257.10. m/z found, 258.2 [M+H]$^+$. $^1$H NMR (CDCl$_3$): 7.44-7.30 (m, 4H), 7.25-7.19 (m, 3H), 7.16 (dd, J=7.6, 1.2 Hz, 1H), 3.28-3.10 (m, 3H), 3.01-2.96 (m, 1H), 2.90-2.77 (m, 1H), 2.50 (s, 1H), 1.87-1.80 (m, 1H).

Example 57

(±)-3-(3',4'-Dimethyl-biphenyl-2-yl)-pyrrolidine

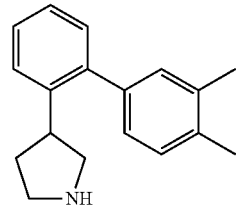 [SMILES: Cc1ccc(-c2ccccc2C2CCNC2)cc1C]

MS (ESI): mass calcd. for $C_{18}H_{21}N$, 251.2. m/z found, 252.3 [M+H]$^+$. $^1$H NMR (CDCl$_3$): 7.45-7.38 (m, 1H), 7.37-7.30 (m, 1H), 7.26-7.15 (m, 3H), 7.12-7.07 (m, 1H), 7.06-6.91 (m, 1H), 3.40-3.11 (m, 3H), 3.09-2.76 (m, 2H), 2.34 (s, 3H), 2.33 (s, 3H), 2.27-2.05 (m, 2H), 1.93-1.80 (m, 1H).

Example 58

(±)-3-(3',4'-Dimethyl-biphenyl-2-yl)-1-methyl-pyrrolidine

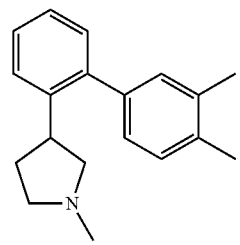 [SMILES: Cc1ccc(-c2ccccc2C2CCN(C)C2)cc1C]

Prepared from general procedure 3 using the title compound of Example 57. MS (ESI): mass calcd. for $C_{19}H_{23}N$, 265.2. m/z found, 266.3 [M+H]$^+$. $^1$H NMR (CDCl$_3$): 7.55 (d, J=8.0 Hz, 1H), 7.35 (dt, J=1.8, 7.1 Hz, 1H), 7.22 (dd, J=7.6, 1.3 Hz, 1H), 7.20 (dd, J=3.6, 1.2 Hz, 1H), 7.17 (d, J=8.0 Hz, 1H), 7.06 (s, 1H), 3.55-3.45 (m, 1H), 2.80 (dd, J=9.0, 8.5 Hz, 1H), 2.75-2.68 (m, 1H), 2.58 (dd, J=9.2, 7.3 Hz, 1H), 2.39 (s, 3H), 2.32 (s, 3H), 2.31 (s, 3H), 2.25-2.14 (m, 1H), 1.95-1.84 (m, 1H).

Example 59

(±)-3-(2'-Methyl-biphenyl-2-yl)-pyrrolidine

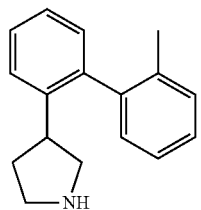 [SMILES: Cc1ccccc1-c1ccccc1C1CCNC1]

MS (ESI): mass calcd. for $C_{17}H_{21}N$, 237.2. m/z found, 238.3 [M+H]$^+$. $^1$H NMR (CDCl$_3$): 7.46-7.32 (m, 1.5H), 7.29-7.18 (m, 5H), 7.15-7.05 (m, 1.5H), 3.22-3.07 (m, 1.5H), 3.05-2.87 (m, 2H), 2.84-2.69 (m, 0.5H), 2.62-2.32 (m, 1.5H), 2.08 (s, 1.5H), 2.06 (s, 1.5H), 2.05-2.01 (m, 1H), 1.95-1.82 (m, 0.5H), 1.83-1.65 (m, 0.5H).

Example 60

(±)-1-Methyl-3-(2'-methyl-biphenyl-2-yl)-pyrrolidine

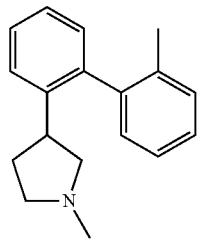 [SMILES: Cc1ccccc1-c1ccccc1C1CCN(C)C1]

Prepared according to general procedure 3 using Example 59. MS (ESI): mass calcd. for $C_{18}H_{21}N$, 251.2. m/z found, 252.3 [M+H]$^+$. $^1$H NMR (CDCl$_3$): 7.56 (d, J=7.9 Hz, 0.5H), 7.53 (d, J=7.9 Hz, 0.5H), 7.37 (dd, J=7.9, 7.2 Hz, 1H), 7.27-7.18 (m, 4H), 7.11-7.06 (m, 2H), 3.26-3.08 (m, 1H), 2.83-2.51 (m, 3.5H), 2.46-2.38 (m, 0.5H), 2.37 (s, 3H), 2.34 (s, 3H), 2.18-2.06 (m, 1H), 2.06 (s, 1.5H), 2.05 (s, 1.5H), 1.96-1.85 (m, 0.5H), 1.84-1.74 (m, 0.5H).

Example 61

(±)-3-(2'-Methoxy-biphenyl-2-yl)-pyrrolidine

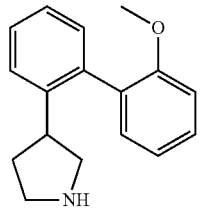 [SMILES: COc1ccccc1-c1ccccc1C1CCNC1]

MS (ESI): mass calcd. for C$_{17}$H$_{19}$NO, 253.2. m/z found, 254.2 [M+H]$^+$. $^1$H NMR (CDCl$_3$): 7.45-7.32 (m, 3H), 7.27-7.21 (m, 1H), 7.21-7.11 (m, 2H), 7.05-6.99 (m, 1H), 6.99-6.92 (m, 1H), 3.75 (s, 1.5H), 3.74 (s, 1.5H), 3.36-3.04 (m, 3H), 3.04-2.87 (m, 2H), 2.87-2.63 (m, 1H), 2.21-2.08 (m, 0.5H), 2.08-1.86 (m, 1H), 1.83-1.67 (m, 0.5H).

Example 62

(±)-3-(2'-Methoxy-biphenyl-2-yl)-1-methyl-pyrrolidine

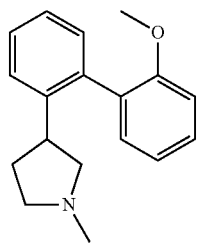 [SMILES: COc1ccccc1-c1ccccc1C1CCN(C)C1]

Prepared according to general procedure 3 using the title compound of Example 61. MS (ESI): mass calcd. for C$_{18}$H$_{21}$NO, 267.2. m/z found, 268.3 [M+H]$^+$. $^1$H NMR (CD$_3$OD/CDCl$_3$): 7.42-7.35 (m, 1H), 7.32-7.21 (m, 2H), 7.20-7.11 (m, 1H), 7.08-7.00 (m, 2H), 6.96-6.89 (m, 1H), 6.89 (d, J=8.3 Hz, 1H), 3.65 (s, 3H), 3.30-3.13 (m, 1.5H), 2.88-2.77 (m, 0.5H), 2.78-2.64 (m, 1H), 2.61-2.47 (m, 2H), 2.28 (s, 1.5H), 2.24 (s, 1.5H), 2.19-2.05 (m, 0.5H), 2.01-1.82 (m, 1H), 1.79-1.64 (m, 0.5H).

Example 63

(±)-3-(2'-Methoxy-5'-methyl-biphenyl-2-yl)-pyrrolidine

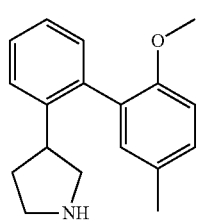 [SMILES: COc1ccc(C)cc1-c1ccccc1C1CCNC1]

MS (ESI): mass calcd. for C$_{18}$H$_{21}$NO, 267.2. m/z found, 268.2 [M+H]$^+$. $^1$H NMR (CDCl$_3$): 7.39-7.29 (m, 2H), 7.24-7.18 (m, 1H), 7.16-7.10 (m, 2H), 7.00-6.93 (m, 1H), 6.88-6.83 (m, 1H), 3.75-3.68 (m, 3H), 3.37-3.05 (m, 3H), 3.04-2.65 (m, 2H), 2.37-2.31 (m, 3H), 2.22-1.69 (m, 2H).

Example 64

(±)-3-(2'-Methoxy-5'-methyl-biphenyl-2-yl)-1-methyl-pyrrolidine

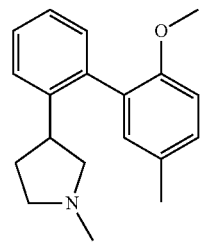 [SMILES: COc1ccc(C)cc1-c1ccccc1C1CCN(C)C1]

Prepared according to general procedure 3 using the title compound of Example 63. MS (ESI): mass calcd. for C$_{19}$H$_{23}$NO, 281.2. m/z found, 282.3 [M+H]$^+$. $^1$H NMR (CDCl$_3$): 7.24-7.17 (m, 1H), 7.15-7.08 (m, 2H), 6.92 (dd, J=7.3, 2.2 Hz, 1H), 6.82 (dd, J=8.3, 2.3 Hz, 1H), 3.69 (s, 3H), 3.36-3.17 (m, 1H), 2.88-2.49 (m, 3H), 2.37 (s, 3H), 2.34 (s, 3H), 2.30 (s, 3H), 2.27-2.13 (m, 1H), 2.12-2.00 (m, 1H), 2.00-1.84 (m, 1H), 1.84-1.68 (m, 1H).

Example 65

(±)-3-(4,3'-Dichloro-biphenyl-2-yl)-pyrrolidine

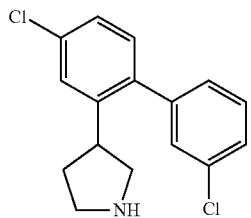 [SMILES: Clc1cccc(-c2ccc(Cl)cc2C2CCNC2)c1]

Step A: Preparation of 1-[3-(5-Chloro-2-methoxy-phenyl)-pyrrolidin-1-yl]-2,2,2-trifluoro-ethanone To the title compound of Example 43 Step A (1.61 g, 5.9 mmol) in MeCN (60 mL) at 0° C. was added oxone (3.6 g, 5.9 mmol) slowly such that the internal temperature of the reaction did not exceed 5° C. over 2 h. The reaction was then placed in a 4° C. freezer for 18 h, then allowed to warm to rt. After an additional 8 h at rt, 10% sodium bisulfite (aq.) was added and the mixture extracted with CH$_2$Cl$_2$ (2×). The combined organic layers were dried and purified. MS (ESI): mass calcd. for C$_{13}$H$_{13}$ClF$_3$NO$_2$, 307.1. m/z found, 308.2 [M+H]$^+$. $^1$H NMR (CDCl$_3$): 7.26-7.19 (m, 1H), 7.15-7.10 (m, 1H), 6.83 (dd, J=8.7, 4.7 Hz, 1H), 4.18-4.06 (m, 1H), 3.98-3.88 (m, 1H), 3.86 (s, 1.5H), 3.84 (s, 1.5H), 3.78-3.68 (m, 1H), 3.67-3.57 (m, 1H), 3.56-3.41 (m, 1H).

Step B: Preparation of 1-[3-(5-Chloro-2-hydroxy-phenyl)-pyrrolidin-1-yl]-2,2,2-trifluoro-ethanone Prepared according to Example 51 Step A from the title compound of Step A. MS (ESI): mass calcd. for C$_{12}$H$_{11}$ClF$_3$NO$_2$, 293.7; m/z found, 294.2 [M+H]$^+$. $^1$H NMR (CDCl$_3$): 7.38-7.17 (m, 2H), 7.10-6.84 (m, 1H), 4.22-4.00 (m, 1H), 3.99-3.34 (m, 4H), 2.68-2.25 (m, 2H).

Step C: Preparation of Trifluoro-methanesulfonic acid 4-chloro-2-[1-(2,2,2-trifluoro-acetyl)-pyrrolidin-3-yl]-phenyl ester Prepared according to Example 38 Step A using the title compound of Step B. MS (ESI): mass calcd. for C$_{13}$H$_{10}$ClF$_6$NO$_4$S, 425.7. m/z found, 426.1 [M+H]$^+$. $^1$H NMR (CDCl$_3$): 7.41-7.35 (m, 2H), 7.30-7.24 (m, 1H), 4.19 (dd, J=10.4, 7.9 Hz, 0.5H), 4.12 (dd, J=12.5, 7.9 Hz, 0.5H), 4.00 (dd, J=9.6, 8.3 Hz, 0.5H), 3.94 (ddd, J=12.1, 8.5, 2.8 Hz, 0.5H), 3.82-3.73 (m, 1H), 3.72-3.64 (m, 1H), 3.61-3.51 (m, 1H), 2.55-2.38 (m, 0.5H), 2.22-2.01 (m, 1H).

Step D: Preparation of 1-[3-(4,3'-Dichloro-biphenyl-2-yl)-pyrrolidin-1-yl]-2,2,2-trifluoro-ethanone Prepared according to Example 51 Step C using the title compound of Step C. MS (ESI): mass calcd. for C$_{18}$H$_{14}$Cl$_2$F$_3$NO, 387.0; m/z found, 388.1 [M+H]$^+$. $^1$H NMR (CDCl$_3$): 7.47-7.34 (m, 3H), 7.33-7.23 (m, 2H), 7.20-7.08 (m, 2H), 4.01-3.92 (m, 0.5H), 3.91-3.80 (m, 1.5H), 3.63-3.54 (m, 0.5H), 3.53-3.43 (m, 2H), 3.42-3.31 (m, 0.5H), 2.32-2.11 (m, 1.5H), 2.10-1.97 (m, 0.5H).

Step E. Preparation of 3-(4,3'-Dichloro-biphenyl-2-yl)-pyrrolidine

Prepared according to general procedure 3 using the title compound from Step D. MS (ESI): mass calcd. for C$_{16}$H$_{15}$O$_2$N, 291.1. m/z found, 292.1 [M+H]$^+$. $^1$H NMR (CDCl$_3$): 7.44-7.41 (m, 1H), 7.37-7.32 (m, 2H), 7.27-7.19 (m, 2H), 7.17-7.07 (m, 2H), 4.65-3.95 (br m, 1H), 3.70-3.45 (m, 1H), 3.42-3.14 (m, 3H), 2.22-2.04 (m, 1.5H), 2.00-1.82 (m, 1.5H).

Example 66

(±)-3-(4-Chloro-4'-fluoro-3'-methyl-biphenyl-2-yl)-pyrrolidine

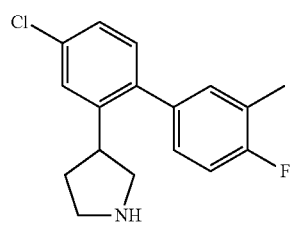 [SMILES: Cc1cc(-c2ccc(Cl)cc2C2CCNC2)ccc1F]

Prepared according to Example 65 using 3-methyl-4-fluorophenylboronic acid. MS (ESI): mass calcd. for C$_{17}$H$_{17}$ClFN, 289.1. m/z found, 290.2 [M+H]$^+$. $^1$H NMR (CDCl$_3$): 7.38 (d, J=2.1 Hz, 1H), 7.19 (dd, J=8.2, 2.2 Hz, 1H), 7.10 (d, J=8.2 Hz, 1H), 7.08-6.98 (m, 3H), 3.32-3.12 (m, 3H), 3.09-2.73 (m, 3H), 2.32 (s, 3H), 2.17-2.03 (m, 1H), 1.89-1.74 (m, 1H).

Example 67

(±)-3-(4-Chloro-3',4'-dimethyl-biphenyl-2-yl)-pyrrolidine

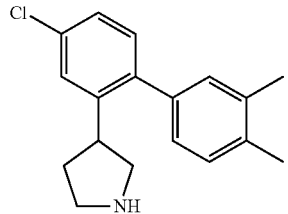 [SMILES: Cc1ccc(-c2ccc(Cl)cc2C2CCNC2)cc1C]

Prepared according to Example 65 using 3,4-dimethylphenylboronic acid. MS (ESI): mass calcd. for C$_{18}$H$_{20}$ClN, 285.1. m/z found, 286.3 [M+H]$^+$. $^1$H NMR (CDCl$_3$): 7.38 (d, J=2.2 Hz, 1H), 7.20 (dd, J=8.3, 2.1 Hz, 1H), 7.18 (d, J=8.2 Hz, 1H), 7.13 (d, J=8.2 Hz, 1H), 7.04 (s, 1H), 7.00 (dd, J=7.6, 1.5 Hz, 1H), 3.38-3.10 (m, 3H), 3.07-2.72 (m, 3H), 2.33 (s, 3H), 2.32 (s, 3H), 2.21-2.02 (m, 1H), 1.89-1.74 (m, 1H).

The compounds in Examples 68-69 were prepared similar to Example 1 using 4-(5-bromo-2-methoxy-phenoxy)-piperidine-1-carboxylic acid tert-butyl ester and the appropriately substituted phenylboronic acid.

Example 68

4-(4-Methoxy-biphenyl-3-yloxy)-piperidine

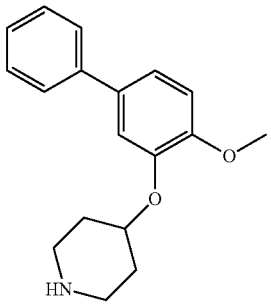 [SMILES: COc1ccc(-c2ccccc2)cc1OC1CCNCC1]

MS (ESI): mass calcd. for C$_{18}$H$_{21}$NO$_2$, 283.2. m/z found, 284.3 [M+H]$^+$. $^1$H NMR (CD$_3$OD/CDCl$_3$): 7.53 (d, J=7.9 Hz, 1H), 7.46-7.37 (m, 2H), 7.31 (dd, J=7.4, 7.3 Hz, 2H), 7.24-7.13 (m, 2H), 6.99 (d, J=8.3 Hz, 1H), 4.46-3.34 (m, 1H), 3.90 (s, 3H), 3.24-3.08 (m, 2H), 2.79-2.63 (m, 2H), 2.14-1.97 (m, 2H), 1.83-1.68 (m, 2H).

Example 69

4-(4-Methoxy-2'-trifluoromethyl-biphenyl-3-yloxy)-piperidine

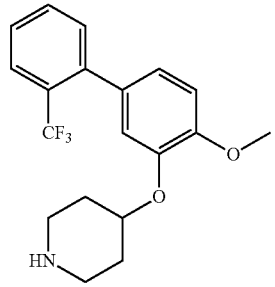 [SMILES: COc1ccc(-c2ccccc2C(F)(F)F)cc1OC1CCNCC1]

MS (ESI): mass calcd. for $C_{19}H_{20}F_3NO_2$, 351.1. m/z found, 352.3 [M+H]$^+$. $^1$H NMR (CDCl$_3$): 7.73 (d, J=7.8 Hz, 1H), 7.53 (dd, J=7.6, 7.5 Hz, 1H), 7.43 (dd, J=7.6, 7.6 Hz, 1H), 7.33 (d, J=7.6 Hz, 1H), 6.94-6.86 (m, 3H), 4.37-4.23 (m, 1H), 3.92 (s, 3H), 3.24-3.10 (m, 2H), 2.74-2.61 (m, 2H), 2.11-1.95 (m, 2H), 1.76-1.61 (m, 2H).

Biological Assays r5-HT$_7$ binding assay

Receptor binding was performed using membrane fractions prepared from the HEK-293 cell line recombinantly expressing rat 5-HT$_7$ receptors (NCBI accession NM_022938). Compound affinity for the rat 5-HT$_7$ receptor subtype was evaluated by competitive radioligand binding assays using 5-carboxamido[$^3$H]tryptamine ([$^3$H]5-CT) (Amersham Biosciences, cat. 90000403) detection. HitHunter™ cAMP assays are in-vitro based competitive immunoassays. The assay was performed on the HEK-293 cell line stably transfected with r5-HT$_7$ receptor. Cells were pre-incubated with test compounds for 10 minutes. For agonistic testing, the concentration of test compound that produced a half-maximal response is represented by the EC$_{50}$ value. Compounds were assayed in their free form or as salts, as indicated in the Examples section above.

TABLE 1

Binding Affinities and Functional Activity

| Ex | 5HT$_7$ Ki (nM) | pEC50 |
|---|---|---|
| 1 | 3.79 | 6.7 |
| 2 | 21.00 | ND |
| 3 | 33.88 | ND |
| 4 | 11.00 | 6.2 |
| 5 | 19.00 | 5.8 |
| 6 | 8.20 | ND |
| 7 | 10.00 | ND |
| 8 | 13.49 | 6.1 |
| 9 | 50.00 | ND |
| 10 | 112.00 | ND |
| 11 | 759.98 | ND |
| 12 | 770.02 | ND |
| 13 | 1000.00 | ND |
| 14 | 249.98 | ND |
| 15 | 120.01 | ND |
| 16 | 114.00 | ND |
| 17 | 4.42 | 6.1 |
| 18 | 532.97 | ND |
| 19 | 299.99 | ND |
| 20 | 25.50 | ND |
| 21 | 34.64 | ND |
| 22 | 751.97 | ND |
| 23 | 67.00 | ND |
| 24 | 8.89 | ND |
| 25 | 10.49 | ND |
| 26 | 15.49 | ND |
| 27 | 410.02 | ND |
| 28 | 127.00 | ND |
| 29 | 10000.00 | ND |
| 30 | 508.04 | ND |
| 31 | 10000.00 | ND |
| 32 | 454.05 | ND |
| 33 | 525.05 | ND |
| 34 | 666.96 | ND |
| 35 | 754.92 | ND |
| 36 | 10000.00 | ND |
| 37 | 2267.25 | ND |
| 38 | 189.02 | ND |
| 39 | ND | ND |
| 40 | ND | ND |
| 41 | 470.00 | ND |
| 42 | 209.99 | ND |
| 43 | 5.46 | ND |
| 44 | 19.00 | ND |
| 45 | 52.00 | ND |
| 46 | 117.00 | ND |

TABLE 1-continued

Binding Affinities and Functional Activity

| Ex | 5HT$_7$ Ki (nM) | pEC50 |
|---|---|---|
| 47 | 7.98 | ND |
| 48 | 19.77 | ND |
| 49 | 129.99 | ND |
| 50 | 150.00 | ND |
| 51 | 120.01 | ND |
| 52 | 80.24 | ND |
| 53 | 310.03 | ND |
| 54 | 120.01 | ND |
| 55 | 430.03 | ND |
| 56 | 180.01 | ND |
| 57 | 55.94 | ND |
| 58 | 155.02 | ND |
| 59 | 209.99 | ND |
| 60 | 329.99 | ND |
| 61 | 299.99 | ND |
| 62 | 729.96 | ND |
| 63 | 1699.81 | ND |
| 64 | ND | ND |
| 65 | 129.99 | ND |
| 66 | 380.01 | ND |
| 67 | 120.01 | ND |
| 68 | 1482.86 | ND |
| 69 | 59.01 | ND |

*ND symbolizes not determined.

While the invention has been illustrated by reference to exemplary and preferred embodiments, it will be understood that the invention is intended not to be limited by the foregoing detailed description, but to be defined by the appended claims as properly construed under principles of patent law.

What is claimed is:

1. A method of treating a subject suffering from or diagnosed with a disease, disorder, or condition selected from the group consisting of: sleep disorders, depression/anxiety, generalized anxiety disorder, schizophrenia, bipolar disorders, cognitive disorders, mild cognitive impairment, Alzheimer's disease, Parkinson's disease, psychotic disorders, phobic disorders, obsessive-compulsive disorder, mood disorders, post-traumatic stress disorder, migraine, pain, eating disorders, obesity, sexual dysfunction, metabolic disturbances, hormonal imbalance, hot flushes associated with menopause, alcohol abuse, drug abuse, drug addiction, alcohol addiction, nausea, inflammation, centrally mediated hypertension, sleep/wake disturbances, jetlag, and circadian rhythm abnormalities, comprising administering to the subject an effective amount of at least one compound of Formulae (I) or (II):

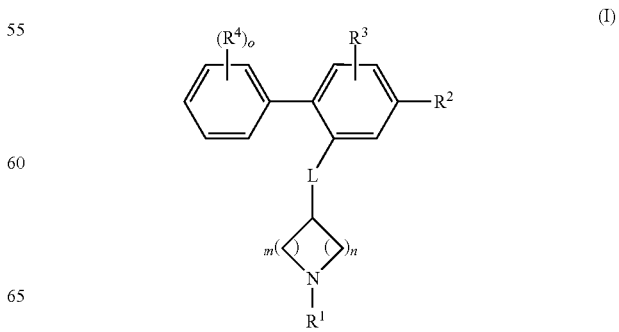

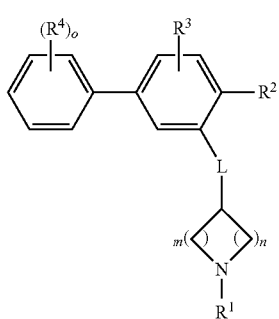

wherein
R¹ is —H, —C$_{1-4}$alkyl, or C$_{3-6}$cycloalkyl;
m is 1,
n is 1 or 2;
L is absent or O;
R² is —H, halo, —CN, —CF$_3$, —OC$_{0-4}$alkylCF$_3$, —OC$_{1-4}$alkyl, —C$_{3-6}$cycloalkoxy, —OCH$_2$C$_{3-6}$cycloalkyl, or —C(O)N(R$_a$)$_2$;
each R$_a$ is individually —H or —C$_{1-4}$alkyl;
R³ is —H or —C$_{1-4}$alkyl;
o is 0, 1, or 2; and
each R⁴ substituent is independently —H, halo, —OCF$_3$, —CF$_3$, —CN, —C$_{1-4}$alkyl, or —OC$_{1-4}$alkyl;
or a pharmaceutically acceptable salt of a compound of Formulae (I) or (II), a pharmaceutically acceptable prodrug of a compound of Formulae (I) or (II), or a pharmaceutically active metabolite of a compound of Formulae (I) or (II).

2. A method according to claim 1, wherein the disease, disorder, or condition is selected from the group consisting of: sleep disorders, depression/anxiety, generalized anxiety disorder, schizophrenia, bipolar disorders, cognitive disorders, mild cognitive impairment, Alzheimer's disease, Parkinson's disease, psychotic disorders, phobic disorders, obsessive-compulsive disorder, mood disorders, post-traumatic stress disorder, pain, alcohol abuse, drug abuse, drug addiction, and alcohol addiction.

3. A method according to claim 1, wherein the disease, disorder, or condition is selected from the group consisting of: depression/anxiety, generalized anxiety disorder, schizophrenia, bipolar disorders, psychotic disorders, phobic disorders, obsessive-compulsive disorder, and mood disorders.

4. A method according to claim 1, wherein the disease, disorder, or condition is selected from the group consisting of: alcohol abuse, drug abuse, drug addiction, and alcohol addiction.

5. A method according to claim 1, wherein the disease, disorder, or condition is Alzheimer's disease.

6. A method according to claim 1, wherein the disease, disorder, or condition is post-traumatic stress disorder.

7. A method according to claim 1, wherein the disease, disorder, or condition is drug addiction.

8. A method according to claim 1, wherein the disease, disorder, or condition is alcohol addiction.

9. A method according to claim 1, wherein the disease, disorder, or condition is pain.

10. A method according to claim 1, wherein the disease, disorder, or condition is depression/anxiety.

\* \* \* \* \*